United States Patent
Bowden et al.

(10) Patent No.: US 12,369,595 B2
(45) Date of Patent: Jul. 29, 2025

(54) MODULAR MOBILE TREATMENT AND PRECOOLING APPARATUS AND SYSTEMS

(71) Applicant: RLMB GROUP, LLC, Honolulu, HI (US)

(72) Inventors: Randall Craig Bowden, Honolulu, HI (US); Robert W. Herdeman, Loveland, OH (US)

(73) Assignee: RLMB GROUP, LLC, Honolulu, HI (US)

( * ) Notice: Subject to any disclaimer, the term of this patent is extended or adjusted under 35 U.S.C. 154(b) by 117 days.

(21) Appl. No.: 17/610,402

(22) PCT Filed: Apr. 30, 2021

(86) PCT No.: PCT/US2021/030178
§ 371 (c)(1),
(2) Date: Nov. 10, 2021

(87) PCT Pub. No.: WO2021/222753
PCT Pub. Date: Nov. 4, 2021

(65) Prior Publication Data

US 2023/0040785 A1 Feb. 9, 2023

Related U.S. Application Data

(60) Provisional application No. 63/068,551, filed on Aug. 21, 2020, provisional application No. 63/019,001, filed on May 1, 2020.

(51) Int. Cl.
*A23B 4/06* (2006.01)
*A23B 2/725* (2025.01)
(Continued)

(52) U.S. Cl.
CPC .......... *A23B 2/80* (2025.01); *A23B 2/725* (2025.01); *A23B 4/06* (2013.01); *A23B 4/066* (2013.01);
(Continued)

(58) Field of Classification Search
CPC . A23L 3/36; A23L 3/3454; A23B 7/04; A23B 7/0425; A23B 7/152; A23B 7/153;
(Continued)

(56) References Cited

U.S. PATENT DOCUMENTS 2,751,882 A * 6/1956 Coyner .................... B60P 3/04
62/304
3,733,849 A * 5/1973 Cantagallo ............ F25D 17/005
99/468

(Continued)

FOREIGN PATENT DOCUMENTS

| CN | 215993616 U | 3/2022 |
|---|---|---|
| RU | 2144164 C1 | 1/2000 |
| WO | 2021/222753 A1 | 11/2021 |

OTHER PUBLICATIONS

International Search Report and Written Opinion mailed Oct. 5, 2022, directed to International Patent Application No. PCT/US2022/031364; 17 pages.

(Continued)

*Primary Examiner* — Anthony J Weier
(74) *Attorney, Agent, or Firm* — Michele V. Frank; Venable LLP

(57) ABSTRACT

An improved system for treating, precooling, and handling perishable products uses a mobile container enhanced with increased capacity refrigeration and air flow to recirculate functional substances including sanitizers, and ripening management and conditioning agents across the surface of palletized perishable products during the precooling step.

(Continued)

Sanitizing substances are dispensed into the recirculating air to significantly reduce micro-organisms on the surface coming from the field and avoid recontamination from the cooling warehouse. Conditioning and ripening management substances are recirculated to enable managing the ripeness of a perishable to a target. The mobile container is able to operate independently outside of a refrigerated warehouse used for storage and distribution of the cooled perishable product. The mobile container can be located near harvest or facilities with no colling assets. A combined system using conveyors and operational controls provides automated handling of the perishables from receiving, precooling and treatment and then distribution.

16 Claims, 45 Drawing Sheets

(51) Int. Cl.

| | |
|---|---|
| A23B 2/80 | (2025.01) |
| A23B 4/16 | (2006.01) |
| A23B 4/18 | (2006.01) |
| A23B 4/20 | (2006.01) |
| A23B 4/24 | (2006.01) |
| A23B 4/30 | (2006.01) |
| A23B 7/04 | (2006.01) |
| A23B 7/152 | (2006.01) |
| A23B 7/153 | (2006.01) |
| A23B 7/154 | (2006.01) |
| A23B 7/157 | (2006.01) |
| A23B 7/158 | (2006.01) |
| A61L 2/16 | (2006.01) |
| B65G 67/02 | (2006.01) |
| B65G 67/04 | (2006.01) |
| F25D 11/00 | (2006.01) |
| F25D 17/04 | (2006.01) |

(52) U.S. Cl.
CPC .............. *A23B 4/16* (2013.01); *A23B 4/18* (2013.01); *A23B 4/20* (2013.01); *A23B 4/24* (2013.01); *A23B 4/30* (2013.01); *A23B 7/04* (2013.01); *A23B 7/0425* (2013.01); *A23B 7/152* (2013.01); *A23B 7/153* (2013.01); *A23B 7/154* (2013.01); *A23B 7/157* (2013.01); *A23B 7/158* (2013.01); *A61L 2/16* (2013.01); *B65G 67/02* (2013.01); *B65G 67/04* (2013.01); *F25D 11/003* (2013.01); *A23V 2002/00* (2013.01); *B65G 2201/0202* (2013.01); *F25D 17/042* (2013.01); *F25D 2317/041* (2013.01)

(58) Field of Classification Search
CPC ......... A23B 7/154; A23B 7/157; A23B 7/158; A61L 2/16; B65G 67/02; B65G 67/04; F25D 11/003; F25D 17/042; F25D 2317/041; B65B 2201/0202; A23V 2002/00
See application file for complete search history.

(56) References Cited

U.S. PATENT DOCUMENTS

| | | | | |
|---|---|---|---|---|
| 4,168,597 | A | | 9/1979 | Cayton |
| 4,467,612 | A | * | 8/1984 | Weasel, Jr. ............... F25D 3/105 108/52.1 |
| 4,598,555 | A | * | 7/1986 | Windecker .............. F25D 15/00 62/239 |
| 4,615,178 | A | * | 10/1986 | Badenhop .............. A23L 3/0155 62/169 |
| 5,101,643 | A | * | 4/1992 | Hicke ...................... B60P 3/20 108/51.11 |
| 5,226,972 | A | * | 7/1993 | Bell ........................ A23B 7/148 134/32 |
| 5,516,539 | A | * | 5/1996 | Walsh .................... A23B 7/148 426/327 |
| 5,658,607 | A | * | 8/1997 | Herdeman ............. A23B 7/148 426/419 |
| 6,269,652 | B1 | * | 8/2001 | Grosskopf ................ B60P 3/20 62/239 |
| 7,247,330 | B2 | | 7/2007 | Kuethe et al. |
| 2003/0159595 | A1 | | 8/2003 | Kiefer et al. |
| 2004/0040832 | A1 | * | 3/2004 | Kartheuser ............. B01D 53/86 422/186.3 |
| 2004/0154322 | A1 | | 8/2004 | Felder et al. |
| 2005/0180998 | A1 | | 8/2005 | Brown et al. |
| 2005/0217282 | A1 | * | 10/2005 | Strohm .................. A23B 7/152 62/78 |
| 2007/0196549 | A1 | * | 8/2007 | Brown ..................... A23B 7/04 426/320 |
| 2008/0121548 | A1 | * | 5/2008 | Yousefiani ................ F02K 9/34 206/524.5 |
| 2008/0166694 | A1 | * | 7/2008 | Weber ................. B65D 81/2069 435/1.1 |
| 2009/0058593 | A1 | * | 3/2009 | Breed ............... B60R 21/01546 340/5.2 |
| 2009/0273265 | A1 | | 11/2009 | Aragon |
| 2010/0047414 | A1 | * | 2/2010 | Terranova .............. A23N 12/02 426/333 |
| 2011/0014330 | A1 | | 1/2011 | Meyers et al. |
| 2013/0013099 | A1 | * | 1/2013 | Delele .................... A23B 7/148 700/214 |
| 2013/0156907 | A1 | * | 6/2013 | Larose ..................... A23B 9/18 426/248 |
| 2013/0287626 | A1 | * | 10/2013 | Benedek ................. A61L 2/202 422/2 |
| 2014/0301894 | A1 | * | 10/2014 | Grant ........................ A61L 2/20 422/28 |
| 2017/0102178 | A1 | * | 4/2017 | Azzopardi .............. F25D 15/00 |
| 2018/0273224 | A1 | | 9/2018 | Hung |
| 2018/0356384 | A1 | * | 12/2018 | Faubion ................ G01N 33/004 |
| 2019/0277868 | A1 | | 9/2019 | Privat De Fortune et al. |
| 2020/0041193 | A1 | * | 2/2020 | Sigety ..................... F25D 17/06 |
| 2020/0046266 | A1 | * | 2/2020 | King ..................... C01B 21/086 |
| 2020/0240691 | A1 | | 7/2020 | Richard et al. |
| 2020/0281233 | A1 | * | 9/2020 | Bowden .................. A23B 4/10 |
| 2021/0018248 | A1 | * | 1/2021 | Ditzler .................. A23L 3/3445 |
| 2021/0082022 | A1 | * | 3/2021 | Whitman ......... G06Q 10/06395 |
| 2021/0353794 | A1 | * | 11/2021 | Popa-Simil ............. F24H 3/002 |
| 2021/0393833 | A1 | * | 12/2021 | Cunningham ........... B05B 7/08 |
| 2022/0279821 | A1 | * | 9/2022 | Bowden ................ F25D 11/003 |
| 2023/0025818 | A1 | | 1/2023 | Santora, Jr. |

OTHER PUBLICATIONS

International Search Report and Written Opinion mailed Jul. 28, 2021, in corresponding International Application No. PCT/US2021/030178 (11 pages).

Non-Final Rejection mailed Sep. 23, 2024, directed to U.S. Appl. No. 17/826,048; 23 pages.

\* cited by examiner

|  | Length | | | Width | Height | |
|---|---|---|---|---|---|---|
|  | mm ft | mm ft | mm ft | mm ft | mm ft | mm ft |
| Dimensions | 20' 6,058 | 40' 12,192 | 45' 13,716 | 8' 2,438 | 8' 6" 2,591 | 9' 6" 2,896 |
| Minimum Internal Dimensions | 5,898 19' 4 1/8" | 12,029 39' 5 1/2" | 13,556 44' 5 5/8" | 2,350 7' 8 1/2" | 2,350 7' 8 1/2" | 2,667 8' 9" |
| Minimum Door Opening Dimensions |  |  |  | 2,337 7' 8" | 2,261 7' 5" | 2,565 8' 5" |

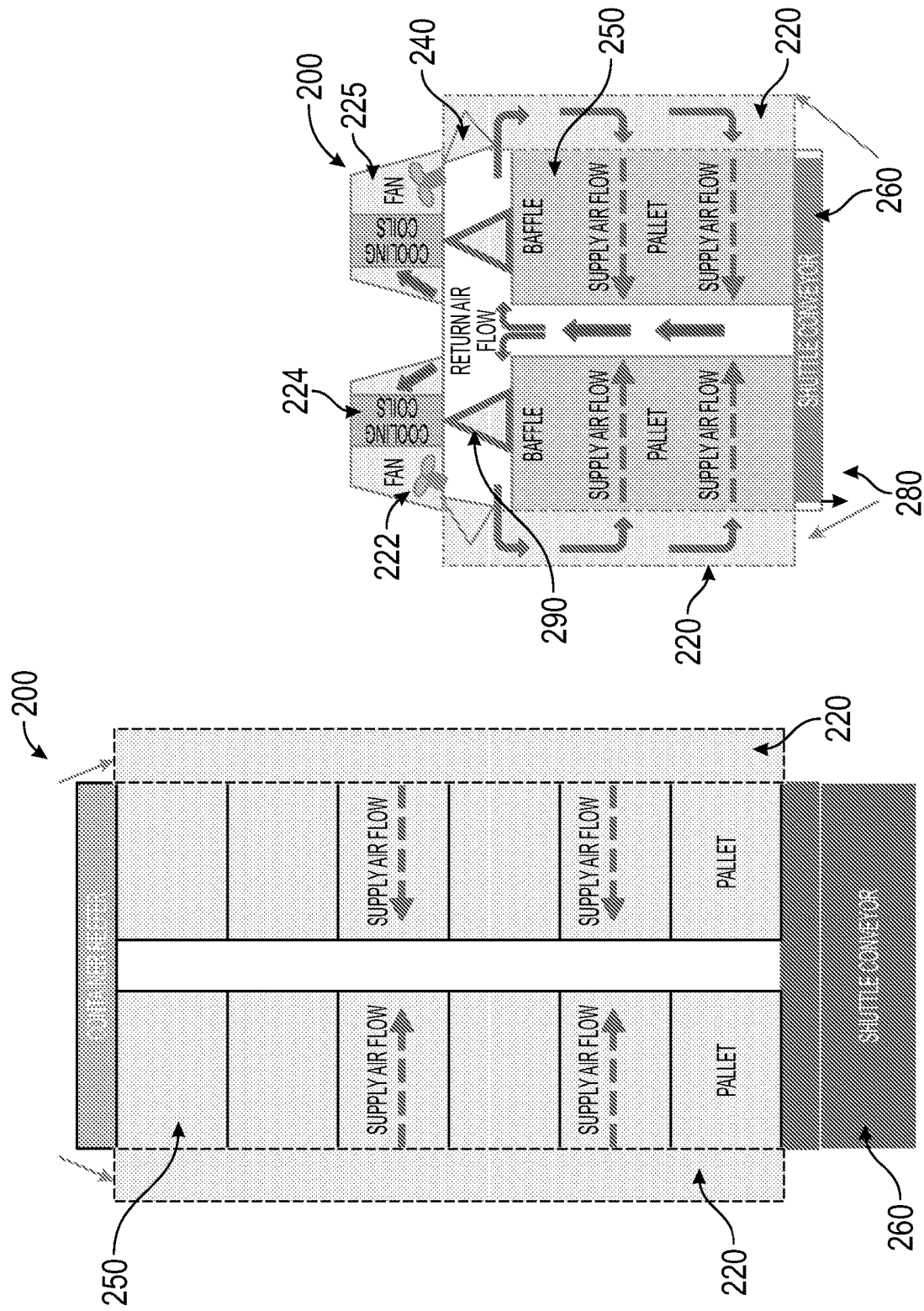

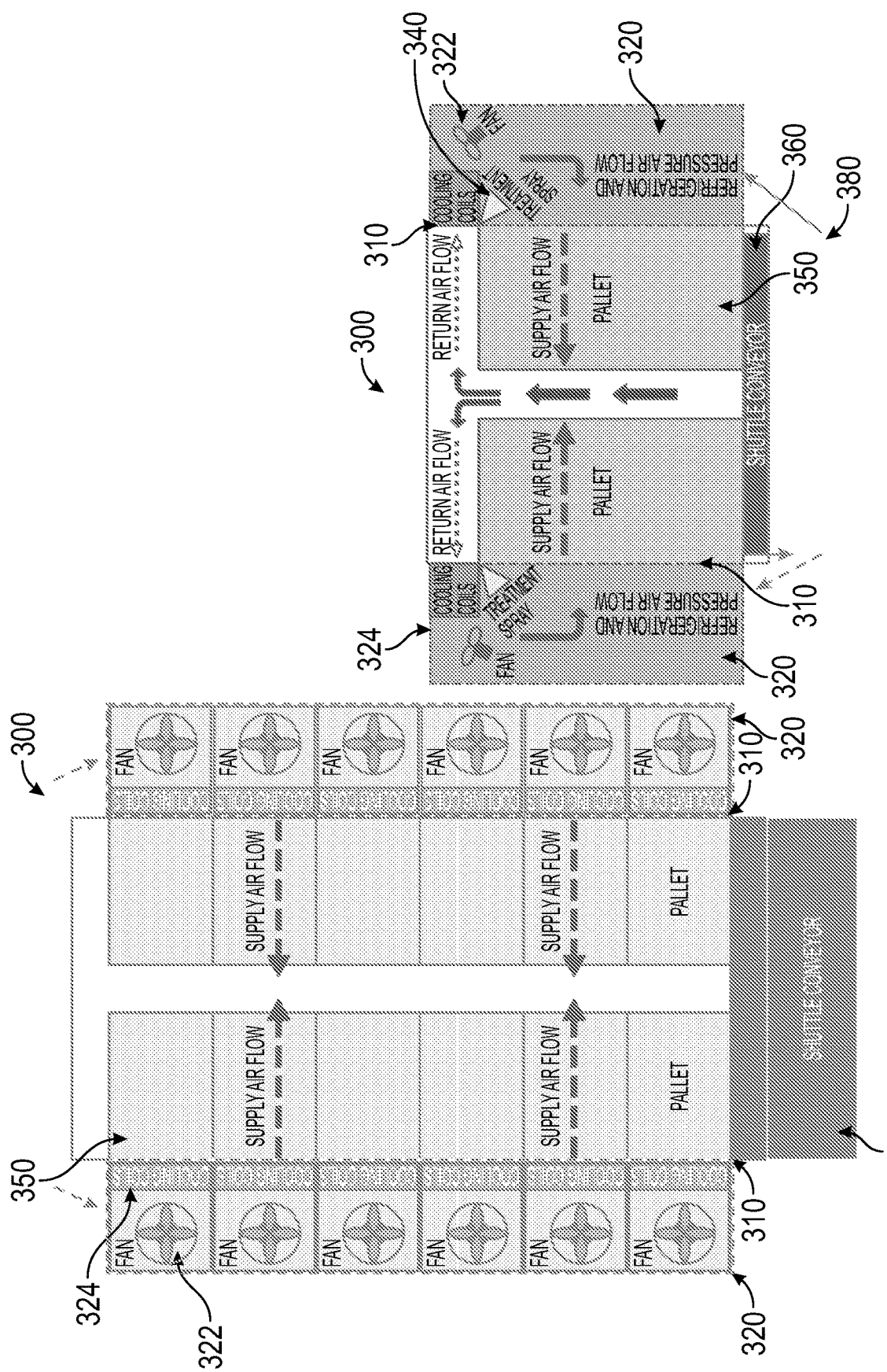

| Rates of Respiration - Strawberries | | | |
|---|---|---|---|
| Temperature | 0°C (32°F) | 10°C (50°F) | 20°C (68°F) |
| ml CO2/kg.hr | 6 - 10 | 25 - 50 | 50 - 100 |

| Rates of Respiration - Berries | | | | |
|---|---|---|---|---|
| Temperature | | ml CO2/kg.hr | | |
| °C | °F | Blackberry | Blueberry | Raspberry |
| 0 | 32 | 11 | 3 | 12 |
| 10 | 50 | 31 | 9 | 49 |
| 20 | 68 | 78 | 34 | 100 |

Source: UCDavis Post Harvest Produce Fact Sheets

| Commodity | Approximate lowest safe temperature[1] | |
| --- | --- | --- |
| | °F | °C |
| Avocados: | | |
|   Cold-tolerant varieties | 40 | 4.4 |
|   Cold-intolerant varieties (West Indies) | 55 | 12.8 |
| Bananas | 55 | 12.8 |
| Beans (snap) | 45 | 7.2 |
| Cucumbers | 45 | 7.2 |
| Eggplants | 45 | 7.2 |
| Grapefruit | 50 | 10.0 |
| Lemons | 50 | 10.0 |
| Limes | 46 | 7.5 |
| Mangoes: | | |
|   Irwin and Zill varieties | 50 | 10.0 |
|   Haden and Keitt varieties | 55 | 12.8 |
| Melons: | | |
|   Cantaloupes | 36 | 2.2 |
|   Honeydew, Casaba, Crenshaw, and Persian | 45 | 7.2 |
|   Watermelons | 40 | 4.4 |
| Okra | 45 | 7.2 |
| Oranges (California and Arizona grown) | 38 | 3.3 |
| Papayas | 45 | 7.2 |
| Peppers (sweet) | 45 | 7.2 |
| Pineapples: | | |
|   Mature-green | 50 | 10.0 |
|   Ripe | 45 | 7.2 |
| Potatoes: | | |
|   Table stock | 38 | 3.3 |
|   Chipping | 50 | 10.0 |
| Pumpkins and hardshell squashes | 50 | 10.0 |
| Sweet potatoes | 55 | 12.8 |
| Tomatoes: | | |
|   Mature-green | 55 | 12.8 |
|   Pink | 45 | 7.2 |

[1] Based on maximum transit time of 5 days; however, chilling injury may vary considerably by cultivar, harvest season, holding time, maturity of commodity, etc.

*Source: USDA, Agricultural Marketing Service, Protecting Perishable Foods During Transport by Truck*

FIG. 21

| Recommended Temperature Range (degrees Fahrenheit) and Relative Humidity (percentage) | Vegetables | Fruits |
| --- | --- | --- |
| 32-36 F<br>90-98 percent | Broccoli, cabbage, kale, leeks, lettuce, mustard greens, peas and turnip greens | Blackberries, blueberries, cantaloupes, cut fruits, figs, peaches, persimmons, quince, raspberries and strawberries |
| 45-50 F<br>85-95 percent | Basil, beans, southern peas, cucumbers, eggplants, okra, peppers, summer squash and tomatillos | Citrus, passion fruit and watermelons |
| 55-65 F<br>85-95 percent | Pumpkins, winter squash, sweet potatoes and tomatoes (ripe, partially ripe and mature green) | Honey dew melons |

FIG. 22

| | Strawberry Post Harvest Process Scenarios | | | | | |
|---|---|---|---|---|---|---|
| | Early am Harvest | | | Afternoon pm Harvest | | |
| | Centralized Regional Whse | At Whse with Mobile Precooling + Sanitation | Harvest Area Mobile Precooling + Sanitation | Centralized Regional Whse | At Whse with Mobile Precooling + Sanitation | Harvest Area Mobile Precooling + Sanitation |
| Harvest Pulp Temperature | 60F | 60F | 60F | 80F | 80F | 80F |
| Respiration Rate (ml CO2/kg.hr) | 50 | 50 | 50 | 100 | 100 | 100 |
| Mold Spores and Spoilage Organisms | Initial CFU | Initial CFU | Initial CFU | Initial CFU | Initial CFU | Initial CFU |
| Harvest to Start Cool Time (hours) | 3 | 2 | 1 | 7 | 4 | 1 |
| Precool Time | 2 | 1 | 1 | 4 | 2 | 2 |
| Precooling % RH | 65% | 90% | 90% | 65% | 90% | 90% |
| Precooling Wt. Loss | 5% | 2% | 2% | 5+% | 2% | 2% |
| 12 Hr Respiration Total (ml CO2/kg) | 226 | 169 | 123 | 973 | 507 | 219 |
| Post Harvest Days Shelf Life Lost | 1.1 | 0.8 | 0.6 | 4.9 | 2.5 | 1.1 |
| Mold Spores and Spoilage Organisms | Increased CFU | Decreased CFU | Decreased CFU | Increased CFU | Decreased CFU | Decreased CFU |

FIG. 26

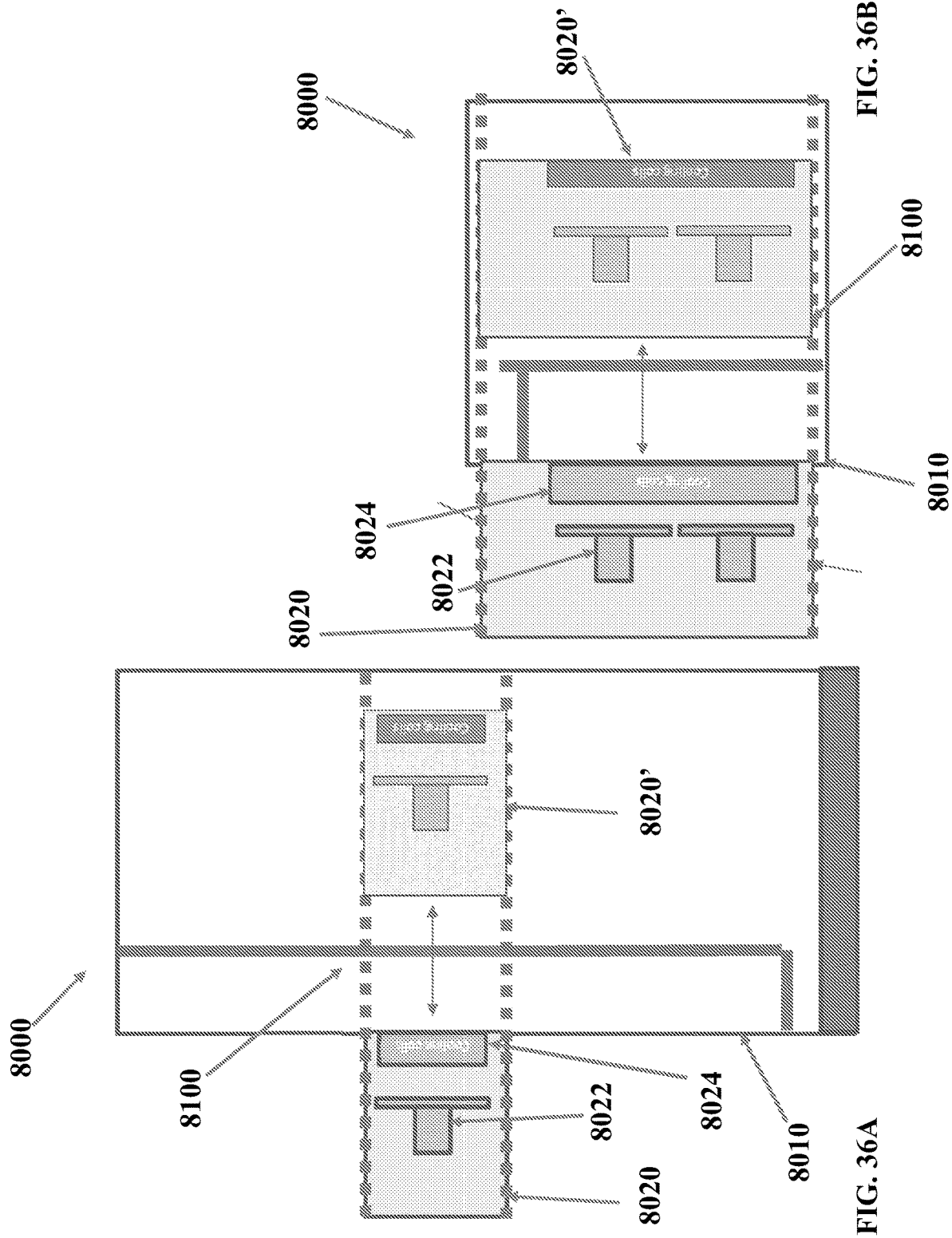

MODULAR MOBILE TREATMENT AND PRECOOLING APPARATUS AND SYSTEMS

RELATED APPLICATIONS

The present application is a National Phase of International Application Number PCT/US2021/030178, filed Apr. 30, 2021, which claims priority to U.S. Provisional Application Nos. 63/019,001, filed May 1, 2020 and 63/068,551, filed Aug. 21, 2020, the entire contents of which are hereby incorporated by reference in their entireties.

TECHNICAL FIELD

The present invention relates to an improved system and method for treating, precooling, and handling perishable products. Functional treatments, like sanitizing substances, are recirculated through pallets and across the surface of the perishable product. The treatments are applied surrounding the process involved with precooling. Combining sanitizing with cooling immediately after harvest solves major current problems by quickly reducing the level of mold and other micro-organisms on the surface of perishables and then preventing cross-contamination of perishables during the enhanced rapid cooling process. These capabilities are not possible or practical in current commercial cooling facilities. The improved system and process eliminates the continual introduction of field contaminated product into the commercial facility and prevents cross-contamination from cooling air that carry mold and other micro-organisms to the surface of perishables. The delivery of the treatments via the improved system and apparatus may be continual, intermittent, pulsed, sequential, or otherwise staged to effect maximum anti-microbial efficacy. Water, used as the substance carrier, is integrated with the humidity control system. Reducing dehydration or hydrating the perishable is accomplished by constantly replacing the moisture in the air lost as it is cooled. Substances can be added to enhance product quality, safety, value, shelf-life, and/or manage the conditioning or ripeness of the perishable product. The system and methods involve the use of a refrigerated container or semi-trailer modified to add the refrigeration and air flow capability required for effectively recirculating the substances and rapidly cooling the product, and use materials of construction compatible with the various sanitizers and substances that can be used. Using a chassis with the container or semi-trailer, the system is mobile and can be physically moved from a seasonal harvest location and/or a production or greenhouse operation and then re-installed and used when the harvest location moves during the year. As the container or trailer are isolated from the commercial facility/warehouse, a wider range of sanitizers and other functional substances can be safely used. The key components of the system for supplying refrigerations, substance treatments, humidification, and high capacity airflow are all modular and, thus, adaptable for various perishable and operational applications. The sanitizing capabilities of these systems can augment current sanitization, food, and worker safety programs prior to receiving products into facilities. These capabilities can be located at or nearer the actual harvest and production location and/or a greenhouse operation to shorten the time to begin this critical processing step. The refrigeration built-in with the modifications for cooling provides capacity benefits for the user to eliminate the need for fixed pre-cooling, reduce the need, size, and operating costs for fixed cold storage and/or convert valuable space that is generally used within a cold temperature facility for storage instead of pre-cooling. The conceived product handling system substantially improves the capability of the product handling from harvest/receiving through distribution, allowing each step to be carried out in a more timely, effective and cost efficient manner.

BACKGROUND

Generally, perishable product is routinely harvested and processed in ways that do not always yield exceptional quality, condition or ripeness, and shelf life due to multiple root causes that originate with the technology available and practiced by the grower/shipper. Perishable product that is packed in the field and/or a greenhouse in the final consumer package or market ready case is not cleaned, washed, or sanitized to reduce spoilage or pathogenic organisms that may be present on the surface. Additionally, typical produce cooling and distribution facilities operate seasonally during the climate driven growing and harvest seasons. These regional facilities are located within hours of the various harvest locations. The facilities have processing capacities according to their size, design and configuration. Seasonally, these facilities may be strained operationally as a result of the seasonal nature of growing and harvesting. Product is often transited for several hours after harvest just to get to the cooling facility. Upon arrival, it may sit on the delivery truck awaiting to be received. It may then wait again to be positioned for precooling. There is no precooling with field and/or greenhouse packing. Packing houses typically provide no precooling capability at all with a current purpose to just pack, ship, or transfer perishable products to cooling facilities. These operational strains delay getting the product to its intended shipping temperature. Harvest to cool time is one of the most critical process control points. Fruit, vegetable (produce), or cut flower respiration, which is a key indicator for the shelf life of harvested products, is greatly reduced by cooling the product to its lowest possible temperature before chill injury can occur (see, e.g., FIGS. 20 and 21). Produce demands timely and efficient processing. Delays in cooling are typically the primary root cause of quality issues that show up downstream in the market. A direct result is that frequently the perishable is harvested at a less mature stage of ripeness with organoleptic properties that do not match the products' potential eating condition quality or consumers' expectations.

The facility/warehouse operations that are performing the delayed precooling most often do not have rigorous cleaning and sanitization during the seasonal operation. As harvested products are brought into the cooling facility from the fields some of these products bring with them mold and micro-organisms contamination, and the contamination levels generally increase through the harvest season. Air is circulated throughout the cooling facility/warehouse and also forced across the perishables for precooling. Mold and other micro-organisms can accumulate in this air and on the warehouse and/or cooling equipment/process surfaces. This results in further contamination of the perishable product from airborne mold and spoilage organisms pushed through pallets during precooling.

In addition, air that is circulating throughout the warehouse and also forced across the perishables is typically low in relative humidity, as the cooling equipment condenses water from the air. This air, thus, dehydrates the perishable product(s) during precooling.

If the perishable product is sanitized before cooling, then mixed with a contaminated product in a contaminated cold room and/or contaminated cooling air, any mold and microorganisms removed during sanitizing will just be added back to the perishable product. If the perishable product is sanitized after cooling, then the sanitizing process has to reduce an even higher contamination load. In addition, separated steps of sanitizing and precooling, while possible, extend the overall process time and require additional handling and costs. Another key consideration is that when cooling air is shared within the cold storage warehouse with the precooling process, significant limitations are present that relate to operator safety and/or equipment surface corrosion. Moreover, sanitizers and conditioning or ripeness management substances would not be permissible in such a cold storage warehouse.

There, thus, remains a need for improved produce processing that can provide reduced harvest to cool time, clean and, preferably, cooling air containing sanitizer for reduced surface mold, spoilage, and pathogenic organisms, humidified air to reduce dehydration or hydrate, conditioning or ripeness management, while rapidly achieving intended produce temperature.

BRIEF SUMMARY OF THE INVENTION

According to one embodiment, the present invention provides an overall systems approach to treat and cool perishable product to achieve a higher quality product that will have extended shelf life from deterioration and decay. Shelf life issues are caused by delayed or poor precooling and mold or other surface spoilage organisms present. The system includes an overall strategy to select the proper sanitizing substances and application method. The system also includes precooling air flow, cooling, and humidity methods and controls to achieve the intended shipping temperature with minimum dehydration. Whereas most sanitizing processes within a production facility are intended to provide only seconds to a few minutes of contact time with a sanitizer, this system leverages the one hour or more of precooling time to provide an extended exposure period for sanitization. As a system, this then enables the use of sanitization stages, steps or cycles, continual, intermittent or pulsed to achieve the intended microorganism reduction safely without the sanitizer substance treatment negatively affecting the perishable product. Additionally, the application of sanitizing during precooling is unique to standard sanitizing processes that include heating the surface of the product or using a sanitizer at an elevated temperature relative the produce item. The invention further provides operators a flexible approach to shorten the number of handling steps and the time it takes to get the product to its intended state that is ready for shipment.

According to another embodiment, the present invention includes an independent apparatus for cooling a perishable product to its intended temperature using one of (i) a mobile container or (ii) a semi-trailer that is modified to add high capacity refrigeration and high capacity airflow that is forced through pallets of cartons of product and/or vented packages with product. The one of (i) a mobile container or (ii) a semi-trailer includes at least one refrigeration source that is configured to supply a cooled airflow to the one of (i) a mobile container or (ii) a semi-trailer that is directed across the pallets of cartons of product and/or vented packages of product contained within the one of (i) a mobile container or (ii) a semi-trailer. The one of (i) a mobile container or (ii) a semi-trailer is in configured to be movable so as to be relocated to a seasonal growing or production area for year-round utilization.

According to another embodiment, the present invention includes an apparatus for sanitizing a perishable product in which sanitizing substances, inserted in stages, steps, cycles, continually, intermittently, or pulsed, are recirculated within air that flows across a surface of the perishable product with the effect of reducing at least one of (i) pathogenic organisms or (ii) spoilage organisms that occur on the surface of the perishable product. The apparatus comprises one of (a) a mobile container or (b) a semi-trailer that is modified to supply the sanitizing substances to the perishable product, with the one of (i) a mobile container or (ii) a semi-trailer including at least one treatment application system that is configured to supply the sanitizing substances, which can be dispensed to an ultra-fine/fine micron size (e.g., ultra-fine is less than 0.01 microns in size (e.g., gaseous molecules), extra fine is greater than 0.1 microns in size but less than 1 micron (e.g., phages, smoke-like particulates, RNA-biologicals, etc.), super fine is greater than 1 micron in size but less than 10 microns (e.g., substances that can be easily suspended as airborne particulates and/or biologicals), very fine is greater than 10 microns in size and up to 100 microns (e.g., practically airborne suspended substance particles), fine is greater than 100 microns in size but less than 1,000 microns (e.g., substances that will not remain suspended in air), and other less fine substances, which are greater than 1,000 microns in size and are generally very difficult to suspend in air), within the recirculating air, to the surface of the perishable product contained within the one of (i) a mobile container or (ii) a semi-trailer.

According to yet another embodiment, the present invention includes an apparatus for managing the conditioning or ripeness of a perishable product in which specified amounts of ripening accelerating or reducing substances are introduced and recirculated with air that flows across a surface of the perishable product during precooling. The effect is to initiate or reduce ripening to achieve a prescribed ripeness level and organoleptic properties for delivery to the customer. The apparatus comprises one of (a) a mobile container or (b) a semi-trailer that is modified to supply the conditioning or ripening management substances to the perishable product, with the one of (i) a mobile container or (ii) a semi-trailer including at least one treatment application system that is configured to supply the conditioning or ripening management substances to the surface of the perishable product contained within the one of (i) a mobile container or (ii) a semi-trailer. Conditioning is intended to achieve the target preferred organoleptic taste, smell, texture and otherwise eating quality. Conditioning or ripening management substances can include ethylene or ethephon for accelerating ripening or 1-MCP (1-Methylcyclopropene) or similar substances to reduce or delay the impact of ethylene and slow or stop ripening.

According to an embodiment, the high capacity refrigeration provides (i) about 5,000 to about 50,000 Btu's of cooling capacity per hour per pallet of product, (ii) about 25,000 to about 45,000 Btu's of cooling capacity per hour per pallet of product, and/or (iii) about 35,000 Btu's of cooling capacity per hour per pallet of product.

According to an embodiment, the high capacity airflow provides (i) about 200 to about 3,000 cubic feet per minute (cfm) of airflow per pallet of product, (ii) about 500 to about 1,000 cfm of airflow per pallet of product, and/or (iii) about 1,000 to 3,000 cfm per pallet of product. Due to the variability of the static pressure caused by the pallet containers and produce packaging, air flow cfm flowing through the pallet is an estimate, which may be adjusted in the systems process controls to optimize the airflow.

According to an embodiment, airflow is directed horizontally through sides of one or more pallets holding the perishable product.

According to an embodiment, the sanitizing substances are mixed with a carrier that includes one of air, industrial gas, water, or alcohol. According to one embodiment, the carrier is water and the mixture is vaporized or distributed via a very small droplet size using a device consisting of at least one of ULV high pressure spray, an ultrasonic humidifier, a nebulizer, a hot fogger, or a cold fogger. The substances can then be added to the air flow stream in stages, steps, continually, intermittently, cycles or pulsed to maximize efficacy.

According to an embodiment, the high velocity air flow recirculating through the pallets aids in the creation of small droplet size and/or dispersement of the substances applied within the container. The use of various techniques for creating, releasing, and distributing substances into the airflow to treat the perishable product are contemplated as an important element of the system. Such techniques include, for example, the use of microbubbles released into the recirculated fan airflow that will more uniformly distribute the selected functional substances (using pressurized $N_2$, $CO_2$, and/or pressurized air) to the surface of the palletized products.

According to an embodiment, an environment inside the one of (i) a mobile container or (ii) a semi-trailer is controlled to add nitrogen or carbon dioxide to create an atmosphere in which alcohols, ethers or other flammable or hazardous substances can be safely used as part of the sanitizing process.

According to an embodiment, at least one of the conditioning or ripening accelerating substances is ethylene. According to an embodiment, the ripening reducing substances added are 1-MCP (1-Methylcyclopropene) to (i) stop or delay the ripening of the perishable product or (ii) reduce effects of ethylene. These substances can be applied at various levels, durations, or dwell times to impart a desired effect to condition the perishable to its intended organoleptic characteristics. The ripening accelerating substances cause the perishable, whether climacteric or non-climacteric, to improve its softness, taste, and/or smell when harvested less mature. Ripening suppression substances halt or slow the ripening process when the organoleptic properties are already at or near their mature target. Thus, an adjustment in the rate or degree of ripeness is considered "conditioning."

According to an embodiment, the present invention includes an apparatus to treat perishable products with an agent to impact the produce response to ethylene.

According to an embodiment of the apparatus, the conditioning or ripening management substances are mixed with a carrier that includes one of air, industrial gas, water, or alcohol.

According to another embodiment, the present invention includes a method for treating a perishable product and/or a method of using the various apparatus discussed herein.

According to an embodiment, the sanitizing substances include at least one of ozone, hydrogen peroxide, ionized hydrogen peroxide, ozonated water, ionized water, peracetic acid, sodium hypochlorite, ionized chlorinated water, and any other form(s) (including ionized and oxidized forms) of these substances. In particular, electrochlorinated water (in all of its forms, including AEW, BEW, NEW, and/or SAEW), ionized substances, oxidizing materials, and other sanitizing substances/treatment provides an effective sanitizer, while also being a non-hazardous chemical and safe for humans.

According to an embodiment, a functional treatment is applied. According to one embodiment, the functional treatment comprises a substance selected from the group consisting of: a sanitizer, a preservative, an antifungal, an essential oil, a reducing agent, a surfactant, a humectant, a buffering agent, a mineral salt, alkali metal salts, an aroma, a flavoring agent, a sealing or coating substance, an anti-browning substance, an ethylene scavenger, hydrocolloid, cyclodextrins, lipids, metallic compounds, ethylene reducing compound, ethylene blocking compound, ethylene scavenging compound, a ripening agent, a nutritional substance, a probiotic, de-greening or coloring substances, nanoparticles, phages, enzymes, and a sugar substance. According to another embodiment, the functional treatment comprises a substance selected from the group consisting of: chlorine dioxide, hydrogen peroxide, ionized hydrogen peroxide, peracetic acid, ozone, ionized water, ethanol, isopropyl alcohol, limonene, lemon oil, orange oil, grapefruit oil, rosemary oil, thyme oil, sunflower oil, other fruit-derived oils, tea tree oil, cinnamon oil, *eucalyptus* oil, potassium oleate, sodium dodecyl sulfate (SDS), ascorbic acid, citric acid, sodium bicarbonate, potassium carbonate, calcium phosphate, linear terpenes, cyclic terpenes, alcohols, aldehydes, esters, ketones, lactones, thiols, lipase, rose oil, rose essence, and fruit essence, vitamins, minerals, flavonoids, flavor compounds, color compounds, essence, essential oil, sugar, THC or THC compounds, CBD or CBD compounds, oxidizing materials, probiotics, phages, enzymes, pharmaceutical compounds, or biological compounds.

According to an embodiment, at least one protective coating is applied to at least one of (i) one or more sidewalls of the container or semi-trailer, (ii) refrigeration and/or air flow equipment, and (iii) any other materials that come in contact with sanitizing ingredients.

According to an embodiment, materials of construction used for the refrigeration and/or air flow equipment comprise stainless steel, coatings, or other materials compatible with highly active sanitizer substances.

According to an embodiment, a shuttle conveyor is also provided to move pallets into and out of the modified container or semi-trailer. According to one embodiment, the shuttle conveyor is an in-and-out design. According to another embodiment, the shuttle conveyor is a pass-through design in which pallets are passed-through from one end to the other end of the modified container or semi-trailer. According to one embodiment, the shuttle conveyor is integrated with a second shuttle conveyor that moves pallets to an MAP application system.

According to an embodiment, a shuttle conveyor is provided to automatically transport at least one of cooled pallets and sanitize treated pallets from the modified container or semi-trailer to an enclosure system and/or an MAP application system.

According to an embodiment, a mobile container or a semi-trailer, which is modified according to the invention, is located outside of a cold storage facility, and the refrigeration is independent of the cold storage facility.

According to an embodiment, a mobile container or a semi-trailer, which is modified according to the invention, is located outside of a cold storage facility, and a system for providing the refrigeration is able to connect and utilize a central refrigeration capacity of the cold storage facility.

According to an embodiment, a mobile container that is modified according to the invention, is positioned at a cold storage facility in a way in which the mobile container comprises a pass-through process into a cold storage area of the facility. According to one embodiment, pallets that contain the perishable product (a) enter the mobile container or semi-trailer from outside, (b) are cooled and/or sanitized within the mobile container or semi-trailer, and (c) are removed from the mobile container or semi-trailer from inside the cold storage facility.

According to an embodiment, pallets can be re-ordered or mixed to provide multiple perishable products within one pallet.

According to an embodiment, pallets coming from the pass-thru system can move to a pallet conveyor system that automatically transports them to a modified atmosphere pallet (MAP) application system. Integration of sanitizing, precooling, and then MAP provides the ultimate system for preparation of the product, while offering improvements in overall process operation and reduction or elimination of the need for costly central warehouse operations. Further operational systems improvements can include automated conveyors, robot pallet movers, automated staging and pick areas for mixed shipments of produce commodities.

According to an embodiment, the modified mobile container or semi-trailer can be set up in close proximity to the harvest location to eliminate the transit time and handling steps and thus, substantially shorten the time from harvest to cool to shipment.

According to an embodiment, a modified mobile container or semi-trailer can be located outside of a cold storage facility and another modified mobile container or semi-trailer can be located as a pass-thru system. These systems can be used together or in sequence or in tandem. According to one embodiment, a sanitizing treatment can occur in one modified mobile container or semi-trailer and cooling can occur in the other modified mobile container or semi-trailer. According to another embodiment, a sanitizing treatment and cooling could occur in both modified mobile containers or semi-trailers. That is, the first modified mobile container or semi-trailer could provide a sanitizing treatment and then the second modified mobile container or semi-trailer could cool the product, or vice versa. According to an embodiment, the first modified mobile container or semi-trailer could partially cool the product and the second modified mobile container or semi-trailer could complete the cooling to the intended temperature (e.g., around 32 to 34° F. or as may be appropriate for that commodity).

According to an embodiment, within each modified container or semi-trailer, the sanitizing and cooling processes can be separated into stages or steps, where a periodic amount of sanitizing ingredients is added and then cooling is conducted, or different sanitizing ingredients are added at different times within the treatment and/or cooling process. As some of the sanitizing substances may be in a solution with water, it can be advantageous to apply some treatments prior to cooling, when the air temperature is able to support a higher moisture level. As such, the use of water to carry the substance can be integrated with the control systems to maintain maximum humidity to reduce dehydration or hydrate the perishable. In other cases, applying a water based substance to cooled product enables the sanitizer to condense on the surface of the perishable product and enable its active properties to impact the pathogenic or spoilage organisms present on the surface. Continued cooling would then cause the surface moisture to evaporate to produce a clean, dry perishable surface.

According to an embodiment, at least one treatment application system is provided that is configured to supply at least one of (a) sanitizing substances to a surface of the perishable product contained within the one of (i) a mobile container or (ii) a semi-trailer, and (b) ripening substances to a surface of the perishable product contained within the one of (i) a mobile container or (ii) a semi-trailer.

According to an embodiment, at least one refrigeration unit is provided that is configured to supply and to direct a cooled airflow across pallets of cartons of product and/or vented packages of product contained within the one of (i) a mobile container or (ii) a semi-trailer.

According to an embodiment, modifications to the mobile container include adding refrigeration and air flow components along a wall on an inside of the mobile container for the cooling and/or treatment of at least 9 pallets of perishable product.

According to another embodiment, modifications to the semi-trailer include adding refrigeration and air flow components along a wall on an inside of the semi-trailer for the cooling and/or treatment of at least 12 pallets of perishable product.

According to an embodiment, modifications to the mobile container include adding a refrigeration and air flow unit within the mobile container to enable cooling and treatment air for a container filled with at least 9 pallets of perishable product.

According to another embodiment, modifications to the semi-trailer include adding a refrigeration and air flow unit within the semi-trailer to enable cooling and treatment air for a semi-trailer filled with at least 12 pallets of perishable product.

According to an embodiment, modifications to the mobile container include creating pop-out sidewalls and a roof mounted refrigeration unit to enable horizontal cooling and treatment air for a container filled with at least 18 pallets of perishable product. According to another embodiment, modifications to the semi-trailer include creating pop-out sidewalls and a roof mounted refrigeration unit to enable horizontal cooling and treatment air for a semi-trailer filled with at least 24 pallets of perishable product.

According to an embodiment, modifications to the mobile container include attaching refrigeration units to sidewalls of the mobile containers on the outside, the sidewalls having openings to enable horizontal air to cool and to treat at least 18 pallets of perishable product and to return the air to the refrigeration units. According to another embodiment, modifications to the semi-trailer include attaching refrigeration units to sidewalls of the semi-trailer on the outside, the sidewalls having openings to enable horizontal air to cool and to treat at least 24 pallets of perishable product and to return the air to the refrigeration units. According to one embodiment, the openings in the sidewalls have a vent design that enables them to be opened and closed, and to adjust and direct the air flow to the pallets.

According to an embodiment, slot or expanded floor drains are included that are configured to be (i) sealed during cooling and/or sanitizing treatments and (ii) opened to enable removal of any physical debris, water and/or cleaning solutions from daily cleaning and sanitation of the mobile container or semi-trailer.

According to an embodiment, a sanitizing treatment occurs before cooling in the mobile container or semi-trailer. According to another embodiment, a sanitizing treatment occurs after cooling in the mobile container or semi-trailer. According to yet another embodiment, a sanitizing treatment occurs during cooling in the mobile container or semi-trailer.

According to an embodiment, multiple sanitizing treatments occur before, during, and/or after cooling. According to one embodiment, one sanitizing treatment occurs before, during, or after cooling, and then a second sanitizing treatment occurs within a MAP (modified atmosphere pallet)

process, providing a unique and more effective dual sanitizing treatment. The different treatments may be designed to have effects on the different type of spoilage and/or pathogenic organisms that may be present on the surface of the perishable. The initial treatment cycles may weaken the microorganisms and then enable subsequent sanitizer cycles to more completely deactivate or destroy them. The treatments may have a synergistic effect by the order or sequence of application. Treatments may be synchronized with the temperature of the perishable product during its cooling process.

According to an embodiment, a mechanism is further provided to move pallet closure-sealing pads to meet the pallets that have been loaded into the one of (i) a mobile container or (ii) a semi-trailer, to create a seal to create a positive air flow plenum and thus force air through the pallets instead of around. According to one embodiment, the mechanism to move the pallet closure-sealing pads may be operated by at least one of hydraulic means (cylinders), at least one mechanical device or drive (such as a pulley or servo motor), or air pressure (inflatable pads or cushions). When loading or unloading the container, the mechanism releases the pads and backs away from the pallets.

According to an embodiment, the present invention provides a method of treating a perishable product using a plurality of independent modified containers or semi-trailers, with each independent modified container or semi-trailer of the plurality of independent modified containers or semi-trailers being (a) modified to provide (i) high capacity refrigeration and high capacity airflow, (ii) one or more sanitizing treatments, (iii) a conditioning or ripening management process, (iv) a humidification or hydration process, or (v) a combination of one or more of (i), (ii), (iii), and (iv) and (b) used for (i) cooling, (ii) sanitizing, (iii) controlling or managing a conditioning or ripening process of the perishable product, or (iv) a combination of one or more of (i), (ii), and (iii).

According to an embodiment, a method of using one of the above-described apparatus is provided, in which at least one sensor is included with the one of (i) a mobile container or (ii) a semi-trailer, wherein the at least one sensor performs the following step (a) measuring the concentration of the sanitizing substances in the air to achieve a prescribed treatment, (b) measuring a presence of at least one airborne microorganism to determine when to conclude a sanitizing treatment cycle, (c) measuring a pulp temperature of the perishable product to determine when to conclude a precooling cycle, (d) measuring the environment to determine when to conclude a venting and scrubbing of container gasses to enable removal of the product, and (e) measuring liquid condensate to determine treatment for wastewater removal.

According to one embodiment, the present invention includes a system adaptable for specific perishable products, packaging designs, and operational flexibility, the system comprising at least one sanitization apparatus and at least one cooling apparatus, wherein air flow and cooling capacity is established to achieve a selected sanitizer recirculation and cooling rate, and wherein the sanitizer and cooling processes are controlled for designed purposes and cycles.

According to an embodiment, humidity control to achieve minimum dehydration or hydration of the perishable is provided. According to another embodiment, venting of gases and discharge of liquid condensate and substances is controlled for environmental concerns.

According to an embodiment, an enclosure and a modified atmosphere pallet (MAP) application system is included with the system. According to another embodiment, the system further includes at least one conveyor system to transport the perishable products between one or more of (i) the at least one sanitization apparatus, (ii) the at least one cooling apparatus, and (iii) the modified atmosphere pallet (MAP) application system.

According to one embodiment, the at least one sanitization apparatus and the at least one cooling apparatus are combined into a single container.

According to an embodiment, at least one of (i) the at least one sanitization apparatus and (ii) the at least one cooling apparatus comprises a modified mobile container or semi-trailer that is configured to be setup in close proximity to a harvest or production location, such that a time from harvest to cool and shipment is substantially reduced by one or more hours up to 2 days.

According to an embodiment, a process for treating and cooling the specific perishable products is prescribed by regulating air flow from low to medium to high to achieve a desired dwell time for sanitizing and an intended cooling time.

According to an embodiment, an environment inside the one of (i) a mobile container or (ii) a semi-trailer is controlled to add nitrogen or carbon dioxide to create an atmosphere in which alcohols, ethers or other flammable or hazardous substances can be safely used as part of a sanitizing process.

According to an embodiment, at least one sensor is configured to supply data to a control program of a controller in which a prescribed recipe is saved and the controller will adjust one or more parameters of the process to achieve at least one of a target cooling rate, relative humidity, atmosphere level, substance treatment level, and microorganism count reduction.

According to another embodiment, the present invention provides an overall system for automated postharvest handling, treatment, precooling and preparation for distribution of palletized products supporting production facilities, including field, greenhouse, or indoor growing operations, the system comprising: at least one (a) one or more mobile, portable modified containers or trailers, (b) one or more apparatus for substance treatments, and (c) one or more enhanced capacity refrigeration sources; and one or more conveyors or pallet shuttle apparatus interconnecting the at least one of (a) one or more mobile, portable modified containers or trailers, (b) one or more apparatus for substance treatments, and (c) one or more enhanced refrigeration sources, wherein the system uses prescribed methods and programmed apparatus to provide palletized product sanitizing, precooling, treating, and handling of the palletized products from receiving to loading and shipping.

According to yet another embodiment, the present invention provides an overall system for automated postharvest handling, treatment, precooling and preparation for distribution of palletized products supporting production facilities, including meat harvesting and processing, the system comprising: at least one (a) one or more mobile, portable modified containers or trailers, (b) one or more apparatus for substance treatments, and (c) one or more enhanced refrigeration sources; and one or more conveyors or pallet shuttle apparatus interconnecting the at least one of (a) one or more mobile, portable modified containers or trailers, (b) one or more apparatus for substance treatments, and (c) one or more enhanced refrigeration sources, wherein the system uses prescribed methods and programmed apparatus to provide palletized product sanitizing, precooling, treating, and handling of the palletized products from receiving to loading and shipping.

According to an embodiment, at least one of (a) one or more mobile, portable modified containers and (b) one or more refrigerated trailers includes at least one pallet shuttle apparatus and comprises a pass-thru design to receive product directly from a processing or packing line and to deliver the product from a discharge end directly to one of (i) an MAP system or (ii) loading and shipping.

According to an embodiment, the system(s) described herein provides a more efficient, timely, and cost-effective method for simultaneously cooling and sanitizing perishable product (as the timely cooling step and the timely sanitizing step both individually and together have a significant impact on respiration and shelf-life).

According to an embodiment, an overall system(s) is provided for receiving, sanitizing, treating, cooling, conditioning, handling, picking/packaging, and final preparation for shipping palletized products. According to an embodiment, a modular mobile system includes multiple improvements over the prior art with respect to, e.g., the integrated handling of palletized products, more effective treatments and cooling, and efficiency improvements with respect to required resources including labor, time, energy, costs, and capital.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

FIG. 10A is a diagram illustrating a top view of the precooling system of FIG.

FIG. 10B is a diagram illustrating a side or end view of the precooling system of FIG. 10A.

FIG. 11A is a diagram illustrating a top view of an alternative embodiment of a precooling system of the invention that allows for clipping on the refrigeration and pressure air equipment onto the sides of the container.

FIG. 11B is a diagram illustrating a side or end view of the precooling system of FIG. 11A.

FIG. 21 is a table from the USDA, Agricultural Marketing Service, illustrating safe minimal shipping temperatures for various fruits and vegetables.

FIG. 22 is a table illustrating recommended Temperature Range for various fruits and vegetables.

FIG. 26 is a table comparing the various properties of a harvested perishable product (e.g., strawberry) with respect to current cooling processes (i.e., "Centralized Regional Whse") and the inventive process according to embodiments of the invention.

FIG. 36A is a diagram illustrating a top view of an embodiment of a combined precooling and treatment unit or container of the invention in which a track system for moving the refrigeration equipment into and out of the unit or container is included with the system.

FIG. 36B is a diagram illustrating a side or end view of the container of FIG. 36A.

DETAILED DESCRIPTION OF THE INVENTION

The present disclosure relates to an improved system and method using a modified container or refrigerated semi-trailer for application of sanitizing substances to the surface of a perishable product and also for efficiently precooling perishable product.

Typical produce cooling and distribution facilities operate seasonally during the climate driven growing and harvest seasons. These expensive facilities are typically designed for produce volumes that anticipate a normal rate of product arriving for processing. The time from harvest to being cooled to the intended storage temperature is perhaps the most important postharvest process factor for quality and shelf life. In reality, produce arrives in surges during the day and the season in a way that cooling and distribution facilities are generally not able to maintain the intended cooling standards. Under actual commercial cooling conditions, it is extremely difficult to maintain a completely constant air temperature. Warm fruit is constantly being brought into the cooler during operation, and forklifts must pass in and out of the cooler. This can result in the cooling facility temperature increasing or warming during the day, which slows the cooling process and even prevents the cooling systems from delivering the produce to its intended temperature. Because of the capacity challenges, regular cleaning and sanitation of the refrigeration and air flow systems is neglected, resulting in air that may contain mold spores and other spoilage organisms. Once airborne, these mold spores and/or organisms can cross-contaminate the produce coming through the facility, resulting in a product with mold and decay during the supply chain to the consumer. Thereafter, the entire impacted facility is left to remain underutilized or idle until the growing season returns.

Additionally, greenhouse facilities and/or packing house facilities that are designed to pack perishable product typically provide no precooling capability. The perishable product is then not cooled until transportation and delivery to a cold storage facility which could be miles, hours or days away. Such locations could take advantage of effective precooling where the equipment required can be easily placed and put into operation to support harvest operations.

Figure 13:
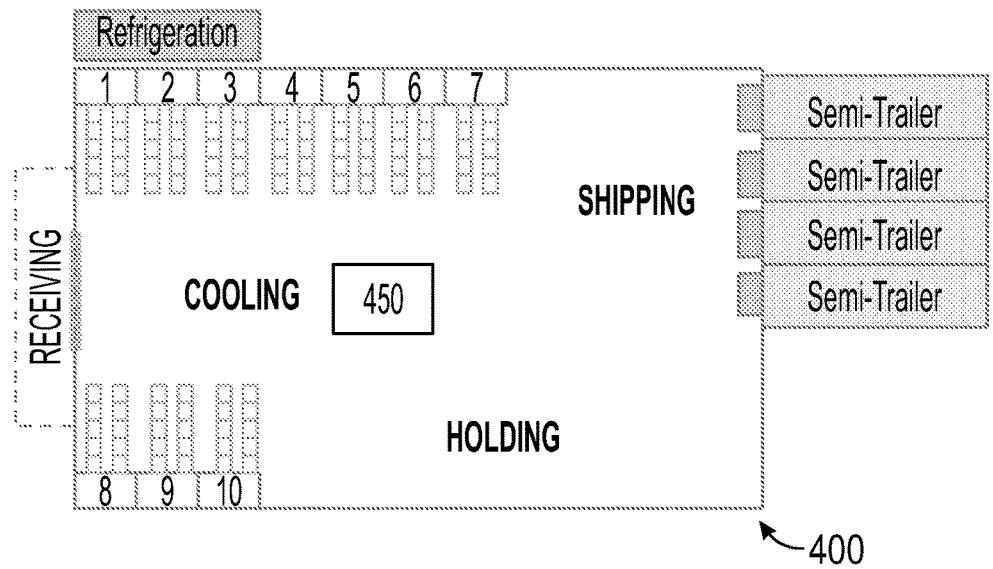
FIG. 13 is a diagram illustrating a typical or conventional cooling, storage, and shipping facility for perishable produce.

For example, current precooling systems for perishable produce are all "fixed in place" installations within cold-room warehouses (see, e.g., FIG. 13). Air within these warehouses that is cooled via a central cooling system is forced through pallets of product that have been transported from a field to cool the product. The central cooling system of these warehouses is thus tasked to remove the field heat that comes out of the pallets of warm product and mixes with the warehouse air. The cold-room warehouses are not frequently sanitized to maintain low micro-organism presence as would be likely present in a perishable processing facility. Accordingly, spores of mold and other spoilage organisms brought in from the fields on some of the product are distributed in the cold warehouse air, thereby exposing and spreading these organisms to other products during the cooling of the product by the central cooling system.

As described above, current precooling systems in warehouses do not provide any type of sanitization to product that has been packed in the field. Their purpose is to cool the product to the target temperature for shipment. So sanitization is a missing step in the process to produce and market perishable product with exceptional quality, shelf life and safety. It is a specific intention of this invention to provide a system, method and apparatus where the product is isolated from the warehouse and operating personnel, and the product can receive a treatment of substances that will reduce or eliminate mold and pathogenic or spoilage organisms. These substances typically have restrictions based upon personnel safety or equipment based on material of construction issues. This dedicated space for providing treatment to the product, in which the product is isolated from the warehouse and operating personnel, can be designed to remedy those limitations or restrictions.

Depending on the physical configuration and weight packed onto a pallet for shipping and the starting temperature of the product or produce after being harvested directly from the field, which can range from about 55° F. to about +95° F. (i.e., an average starting temperature of about 75° F.), about 25,000-45,000 Btu's of cooling is required to cool an individual pallet of product to the intended temperature for storage and shipment, which is generally around 34° F. for commodities, like, e.g., berries. For example, produce or fruit products such as berries have a specific heat ($C_p$) of about 0.95 Btu/lbF. If an average pallet weights 1,000 lbs., then the cooling process ($Q=mC_p dT$) must remove about 34,200 Btu's [0.95 (Btu/lbF)×1,000 (lbs)×31 (F)=34,200 Btu] from the pallet of product. Some additional cooling (Btu's) is typically included in the facility capacity to account for (i) heat of any cooling fans and (ii) condensation of water from the air on the refrigeration surface. Assuming that the additional cooling requirements are about 1,100 Btu's, a total "Q" for a cooling requirement equals to about 35,300 Btu's, for one pallet. It is, thus, intended that the modified container or refrigerated semi-trailer of the invention will provide about 25,000-45,000 Btu's per pallet of cooling capacity, dependent on the physical weight present. The intended cooling time then determines how many Btu's per pallet per hour are required.

Moreover, for cold air to remove the amount of heat discussed above (i.e., about 35,300 Btu's), a similar calculation can be used to determine the amount of air required. In particular, cold air has a specific heat ($C_p$) of about 0.2403 Btu/lbF and a density of about 0.075 lb/cu·ft., with a temperature of about 32° F. Using the total "Q" for a cooling requirement of 35,300 Btu's, the variable of "m" (i.e., the amount of air in cu·ft.) can be determined in the above-discussed equation ($Q=mC_p dT$). This results in an "m" of about 54,400 cu·ft. of 32° F. air that is required to remove the heat. If applied over 60 minutes, this would translate to about 907 cubic feet per minute (cfm) per pallet (or about 450 cfm of airflow per pallet cooled over a two-hour time frame). Currently, intermodal containers and semi-trailers only produce a total of about 20-35,000 Btu's per hour, distributed to all of the pallets present. This is because their primary purpose is to maintain product temperature during transportation. Air flow must, therefore, also be proportionally increased with the modifications to the container or refrigerated semi-trailer of the invention to achieve the cooling in a rapid fashion. It is, thus, intended that air flow with the modifications to the container or refrigerated semi-trailer of the invention will provide about 500 to 3,000 cfm per pallet depending on the weight of the product and amount of static pressure or resistance to air flow caused by the boxes, containers, size and density of the product or produce. This will enable effective recirculation of the sanitizing substances across the pallets of perishable product. The refrigeration to cool the product would be sized and controlled depending on the desired cooling time.

It should be noted that fruits and vegetables all have unique commercial cooling requirements and specifications (see, e.g., FIG. 22). For that matter, the amount of Btu's/hr and cfm per pallet required could be different. Banana pallets, for example, are twice the weight of berries at over 2,000 lbs. In addition, bananas would be cooled from a tropical temperature of about 90° F. to about 58° F. This process to reduce the temperature by 32° F. with twice the fruit amount would require twice the cooling Btu's and air flow for an intended cooling time. Fruit and vegetable items have a preferred cooled temperature where they have a reduced rate of respiration for shipping but don't incur chill damage (see, e.g., FIGS. 20 and 21). Along with different pack weights, packaging, and as-harvested starting product temperature, it should be expected that the cooling and air flow capacity requirements would be appropriately designed to achieve the target cooling time through the modifications of the mobile containers. It is important to note that during this cooling time, the sanitization treatment can be applied to provide a substantial exposure, contact, or dwell time. Longer exposure and dwell times enable use of lower active levels of the sanitizer substances, which can be advantageous to avoiding damage to the perishable product, packaging, as well as the materials of construction.

Additionally, climacteric fruit that is ripening, such as bananas, avocadoes, and tomatoes, produce heat during the ripening process (i.e., heat of reaction during ripening process of converting starch to sugar). The cooling and air flow that is needed to prevent fruit from heating up during ripening is substantially more than that required for maintaining the temperature of a green (or un-ripened) fruit at normal respiration. Accordingly, the cooling (Btu capacity) and air flow required for preventing fruit from heating up during ripening is analogous to the precooling situation described above. Thus, the expanded cooling and air flow capability described above (i.e., a cooling capacity of about 25,000-45,000 Btu's per hour per pallet, and an air flow of about 500 to 1,000 cfm per pallet) reasonably matches with the requirements to remove the heat of ripening from climacteric perishables, such as bananas, avocadoes and tomatoes. Moreover, in use, the modified container or semi-trailer is a closed system, which allows for the modified container or semi-trailer to (i) contain substances for a sanitizing treatment, as well as ethylene, which is generally used to initiate or accelerate ripening and/or (ii) control the humidity and/or moisture vapor pressure differential between the environment and the product. These conditioning and/or ripening features can be important for other items such as melons, kiwi, and stone fruit which are often harvested less than fully ripe and whose quality, condition, and organoleptic properties can be significantly improved by the system and methods including, e.g., exposure to controlled amounts of ethylene.

In view of the foregoing, the modified container or refrigerated semi-trailer of the invention is intended to provide about 25,000-45,000 Btu's per hour per pallet of cooling capacity. Additionally, the modified container or refrigerated semi-trailer of the invention is intended to provide an air flow of about 500 to 3,000 cfm per pallet. Moreover, the mobile container or semi-trailer described herein provides independent and incremental cooling to the operation. The mobile container can augment or replace the air flow plenums or precooling systems currently located within the cold storage facility, freeing up space for produce storage during production peaks. As an independent system, the mobile container is not impacted by volume surges that can occur. By utilizing the additional cooling systems, the user is able to have excess cooling capacity to properly manage all surges. Thereafter, the user is able to get greater utilization of these assets by moving them for use at the next seasonal location. The use of the mobile container enables the user to consider facilities for cooling, storage and distribution that before could not have been considered due to their lack of sufficient size and capacity. Often the construction of large cold storage warehouse involves substantial expense and time due to local regulations and the permitting process. The mobile container is flexible to be able to operate while on the chassis, placed on a frame to match the desired operational height, or also placed on the ground or concrete floor. Such facilities might be called packing houses where there is typically no precooling. The mobile container is also equipped with a sanitizing addition system to reduce the mold and spoilage organism counts on the surface of the produce. Important elements of the container design enable the system to be cleaned of the debris inherent with a field packed product. The mobile container is able to be cleaned and sanitized daily or as needed after use, so as to eliminate the current cross-contamination of mold spores and/or spoilage organisms that occurs with the current cooling process within the warehouse.

Most important of all is that the improved system is able to provide a currently missed step of sanitization to reduce, control, or eliminate mold, pathogenic, or spoilage organisms. Combining this with precooling and the prescribed product handling methods insures the perishable product is not cross-contaminated or re-contaminated within the warehouse.

The overall net result is improved quality from harvest to cool time, intended produce temperature, and reduced surface mold and/or spoilage organisms. The cooling operation has cooling assets that operate more cost efficiently (i.e., asset cost/carton processed), as well as increased storage space to manage surges in production.

In addition, a mobile container that is capable of providing pre-cooling and/or sanitization treatments is an ideal apparatus, method, and system to support, for example, the urban or global smart greenhouse industry. This industry is growing throughout the world due to the need to bring food production closer to the urban population centers, to enable throughout the year growing independent of seasonal weather, and to reduce the costs and lost freshness of extended transportation and logistics. Commercial greenhouses are high-tech structures, which provide stable, highly controlled environments for the cultivation of plants, such as, e.g., flowers, vegetables, and fruits to commercial growers. Environmental factors such as, e.g., temperature, light exposure, irrigation, fertilization, humidity, and ventilation can be precisely controlled by growers in smart greenhouses for the optimal growth of crops. Commercial smart greenhouses enable the cultivation of plants in large volumes for commercial growers. These greenhouses maintain mid-to-high temperatures (often between 45° F. and 100° F., depending on plants being cultivated or the season of the year) using glass or plastic materials to enable the transmission of visible and near-visible ultraviolet (UV) and/or infrared radiation (IR). Another approach to indoor plant growing involves indoor and vertical farms using repurposed buildings, warehouses, or vacant properties. In all cases, a solution is needed for proper post-harvest processing of the perishables. Thus, by providing a mobile container with supporting refrigeration, which can be located at the receiving and shipping dock of these types of facilities, minimal facility modifications would be needed. Importantly, as a programmable system, the necessary precooling conditions and sanitization materials used can be prescribed for the operation. The system can be simply connected to the operation and will function to provide state of the art cooling, sanitization and functional treatments for the perishables to enhance their quality, safety, and provide extended shelf life for consumers.

In a similar fashion, meat and other proteins are being produced at smaller, more local facilities instead of conventional large, regional packing houses. Accordingly, the above-discussed mobile containers with cooling and/or non-thermal or cold treatment capabilities can be utilized for these products. In particular, because the mobile container apparatus can be located outside of the facility and not inside where personnel are present, there is a broader list of materials that can be used to treat the surface of the protein products. Carriers such as, e.g., liquid nitrogen and carbon dioxide can also be used to deliver functional treatments and/or sanitizers to the surfaces of the products.

Accordingly, one embodiment includes an independent apparatus for cooling a perishable product to its intended temperature using one of (i) a mobile container or (ii) a semi-trailer that is modified to add high capacity refrigeration and high capacity airflow that is forced through pallets of cartons with perishable produce. During a period of cooling, sanitizing substances are recirculated with the airflow across a surface of the perishable product with the effect of reducing at least one of (i) pathogenic organisms or (ii) spoilage organisms that occur on the surface of the perishable product. The one of (i) a mobile container or (ii) a semi-trailer is configured to be relocated to a seasonal growing area or production area for year-round utilization.

Another embodiment includes an apparatus for sanitizing a perishable product in which sanitizing substances are recirculated within air that flows across a surface of the perishable product with the effect of reducing at least one of (i) pathogenic organisms or (ii) spoilage organisms that occur on the surface of the perishable product.

Another embodiment includes one or more methods for treating a perishable product and/or using the various apparatus described herein.

Figure 1:
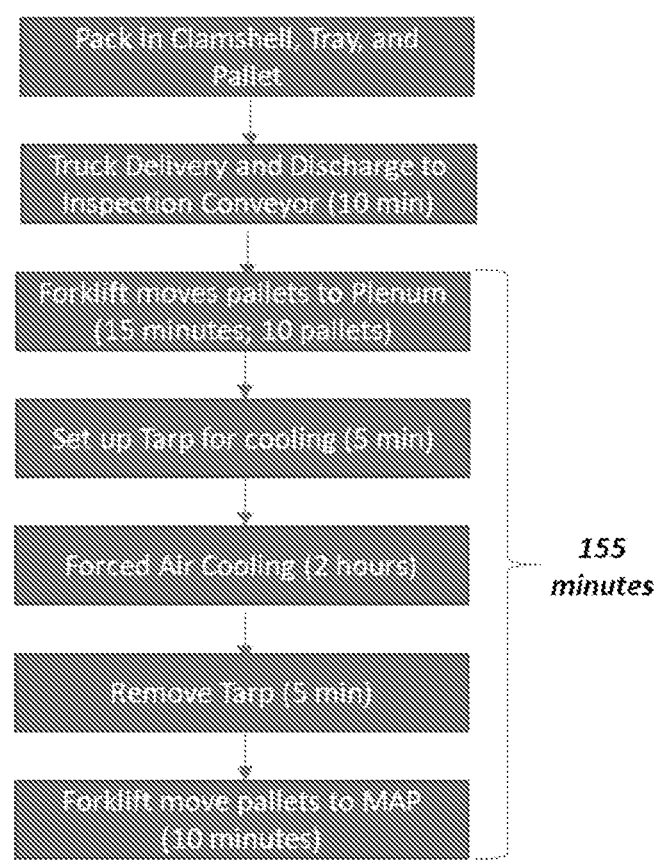
FIG. 1 is a flowchart of the current process to receive palletized containers of perishable produce at a warehouse, cool the product to an intended temperature, and then moving the pallets to storage or a process to enclose the pallet and add a modified atmosphere.
Figure 2:
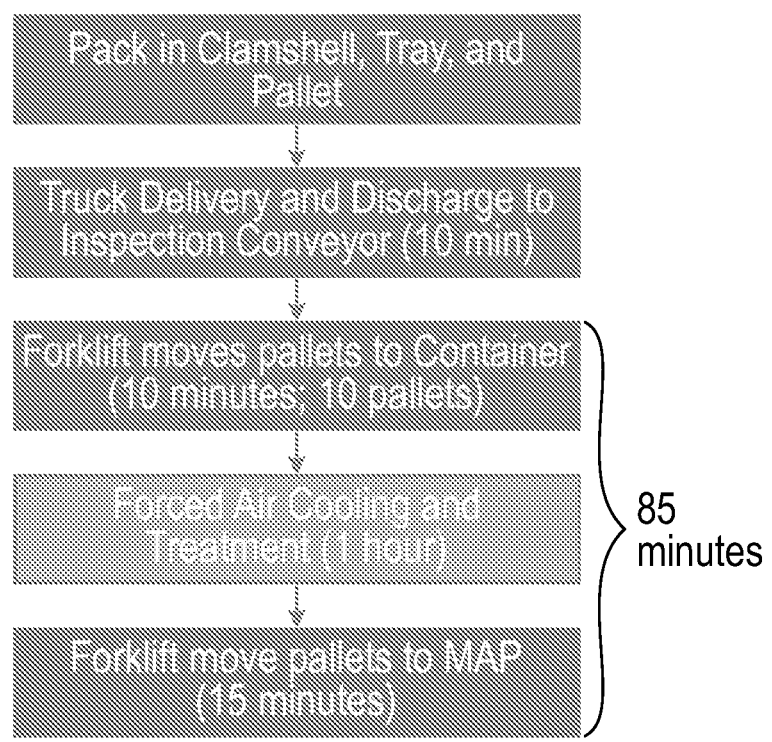
FIG. 2 is a flowchart of an embodiment of the inventive process using a mobile container designed to cool the berries to an intended temperature in one (1) hour and also able to provide a sanitizing treatment during that time period.

FIG. 1 is a flowchart of a typical or conventional berry cooling process. This process uses tarps for vacuum plenums within a cold storage facility. A 10 pallet plenum requires 200 square feet of refrigerated floor space that is adjacent to a wall with a plenum fan (for setting up tarps for cooling), plus access for pallet movement. The facility creates and recirculates 32° F. air throughout. The plenum fan sucks this air through cartons of berries staged at the plenums. Cooling continues until the berries reach the intended temperature of 32-34° F. Berries closest to the suction fans cool faster. The cold air being recirculated in the facility may contain mold spores or other spoilage organisms. Heat from the suction fans and removed from the fruit is mixed in the facility air. If that heat exceeds the capacity of the facility's cooling units, the air will warm and then this warmer air will result in slower cooling and higher finished berry temperature. The greater than two (2) hours to cool ten (10) pallets ("forced air cooling"), along with the pallet movements and tarp plenum setup, results in a total time until delivery to and staging for a MAP (modified atmosphere pallet) of greater than 155 minutes. At this rate, about 40 pallets can be processed within a 10-hour day per plenum. Limited storage space in the cold storage facility often requires the use of racks to store product vertically. This design, which may be necessary for production storage during surges, may be less efficient for pallet movements during peak operating times of the day. For example, when pallets are all placed on the floor of the facility, they can be moved by forklifts one or two at a time and quickly. However, when loading pallets into vertical racks, they must be handled one at a time and very carefully to position the pallets correctly on the rack. This is the same for removing the pallets and placing them in the shipping area. Racks, however, may be necessary when additional cold storage space is needed in the facility, but they have an impact on operations. Additionally, forklift drivers also require more skill for placement of the pallets onto the vertical racks. FIG. 2 is a flowchart of an embodiment of the inventive process using a mobile container designed to cool the berries to an intended temperature in one (1) hour and also able to provide a sanitizing treatment during that time period. Following the cooling and treatment process, the pallets of produce or perishable products are moved into a cold storage facility to a MAP station for final processing. With sufficient cooling capacity applied, this inventive process for a 9-12 pallet container design occurs with 60 minutes of cooling ("forced air cooling and treatment") and translates to 80 pallets processed within a 10-hour operation. At a 2× capacity, along with mobility to cool produce or perishable products at other seasonal harvest or production locations, this system provides a cost effective cooling capability. With this, the process frees up about 400 square feet of space for storage within the cold storage facility. If a lesser amount of cooling capacity is applied, a longer cooling and treatment time will occur, but this will still augment or replace some of the capacity within the cooling facility.

Figure 3:
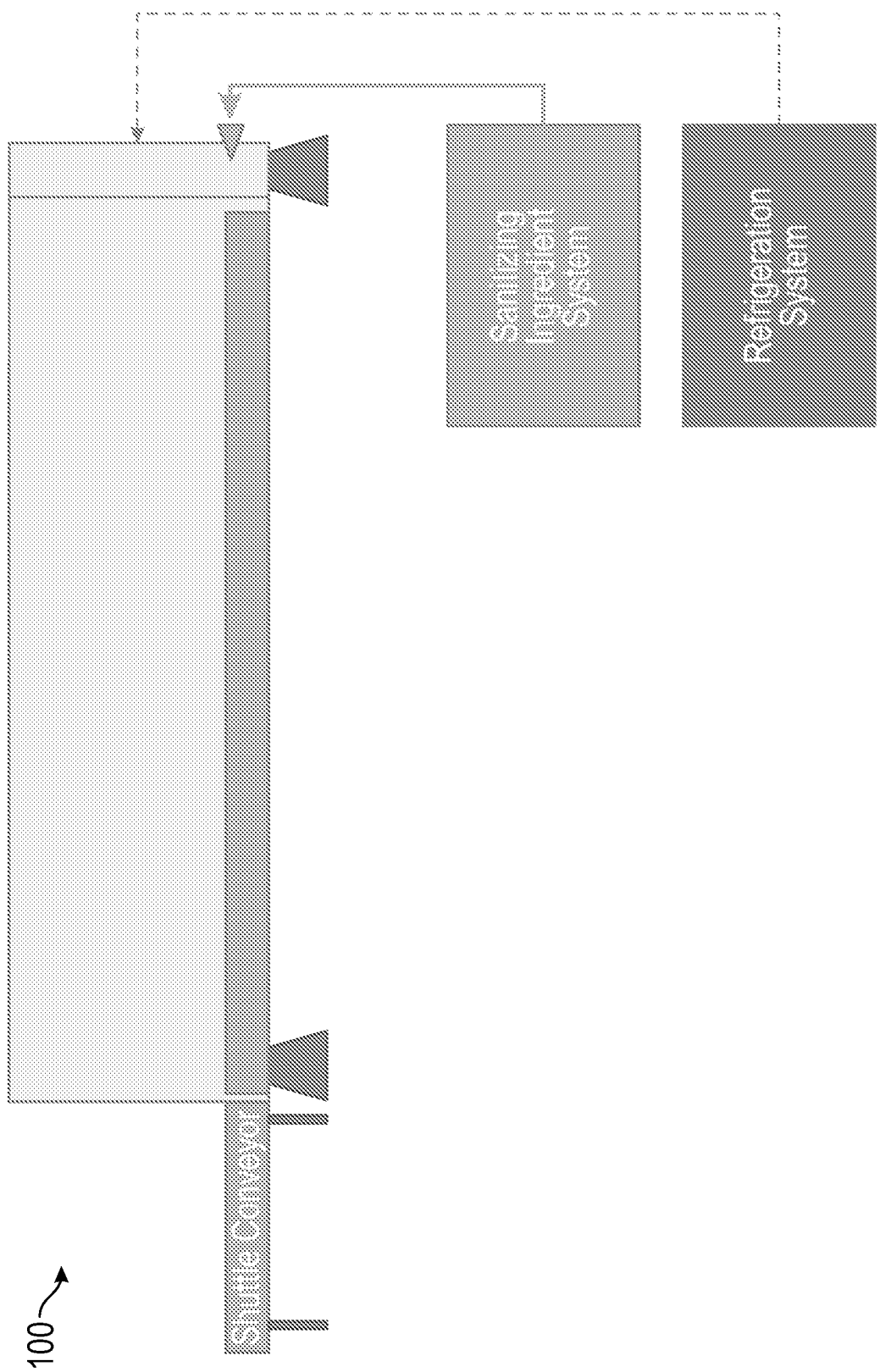
FIG. 3 is a diagram illustrating an embodiment of a precooling system of the invention that is described by the flowchart in FIG. 2, using a 40-foot-high cube reefer container, which could alternatively be a 53-foot-high semi-trailer.
Figure 4:
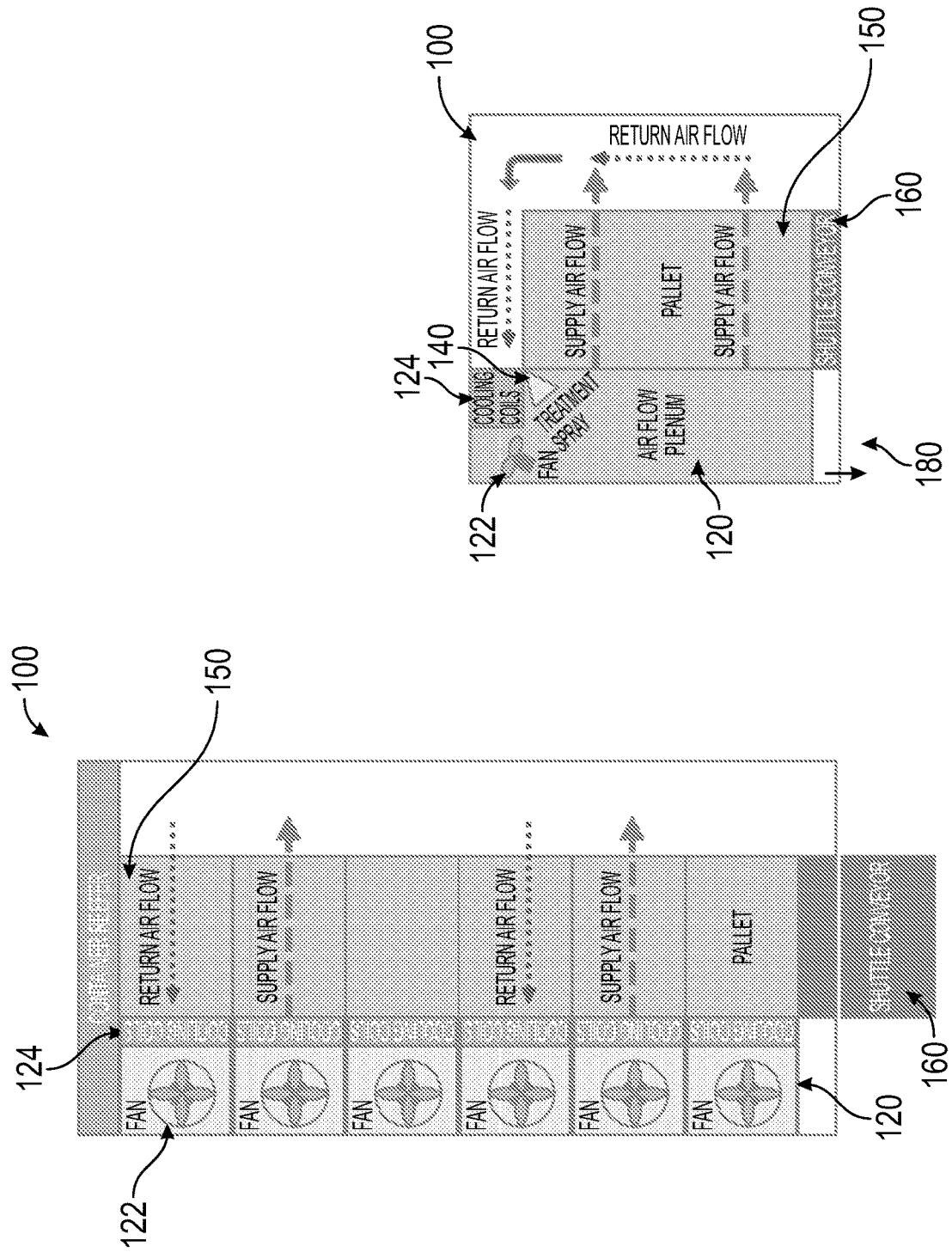
FIG. 4A is a diagram illustrating a top view of the precooling system of FIG. 3.
FIG. 4B is a diagram illustrating a side or end view of the precooling system of FIG. 4A.
Figures 5, 6:
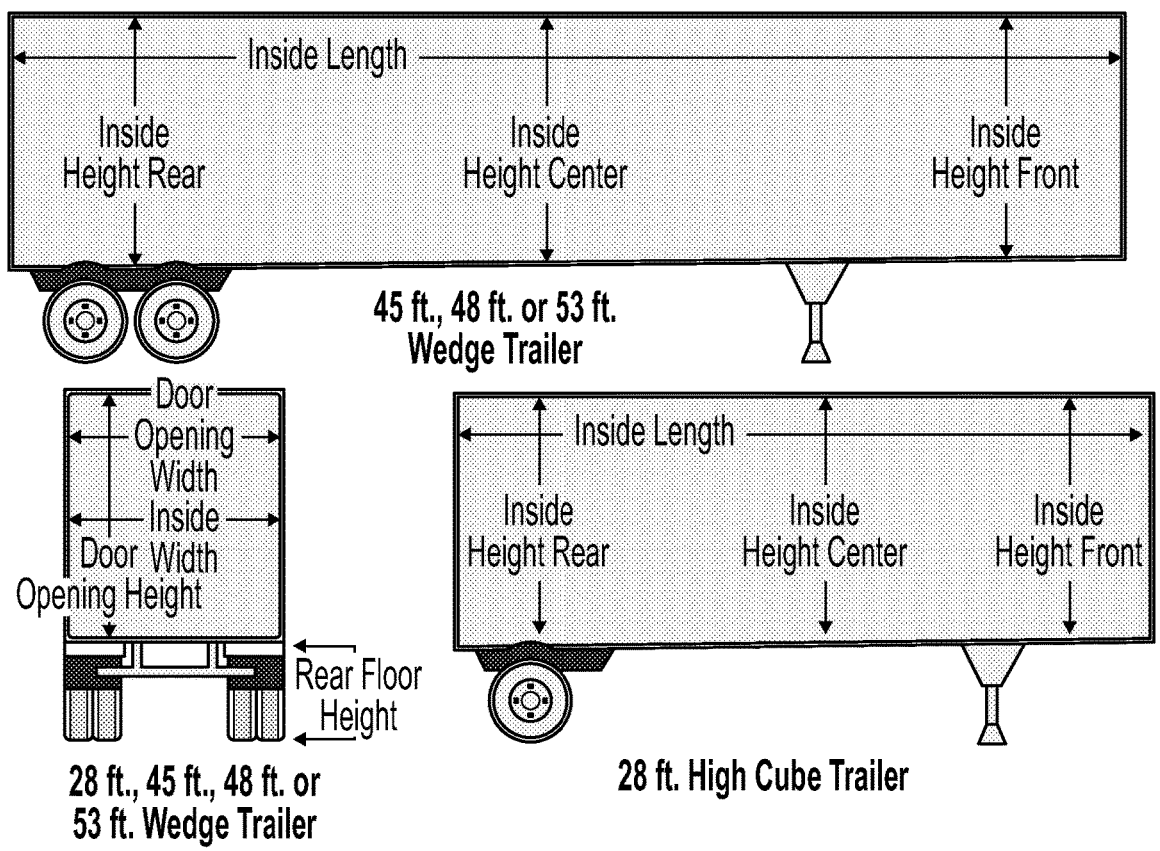
FIG. 5 illustrates refrigerated intermodal container sizes that are available for use with embodiments of the invention, including their internal and external dimensions.
FIG. 6 illustrates refrigerated semi-trailer sizes and dimensions that are available for use with embodiments of this invention.
Figure 7:
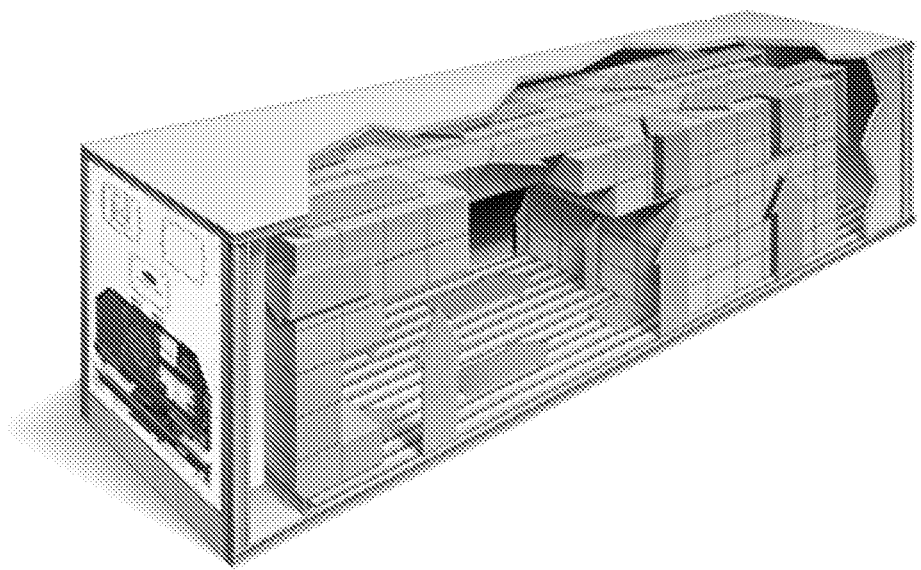
FIG. 7 illustrates the air flow patterns in a conventional refrigerated container.
Figure 8:
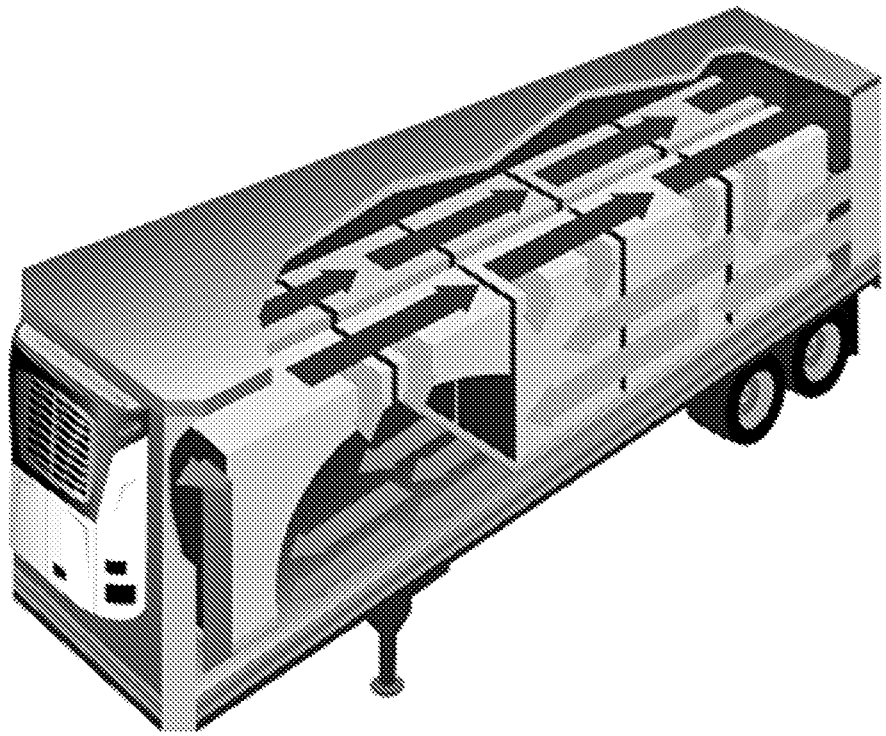
FIG. 8 illustrates the air flow patterns in a conventional refrigerated semi-trailer.

FIGS. 3, 4A, and 4B are diagrams illustrating an embodiment of a precooling system described by the flowchart in FIG. 2. This example reflects using a 40' high cube reefer container (100), but could alternatively be a 53' semi-trailer. This is a modification to a conventional refrigerated container and/or semi-trailers, which are able to be moved to the various seasonal locations where needed. (For example, FIGS. 5 and 6 illustrate information about conventional intermodal refrigerated containers and/or semi-trailers that can be modified according to the embodiments described herein.) In the modification, fans (122) and cooling coils (124) are placed along the side of one wall to create an air flow plenum (120) to force air (horizontal and/or vertical arrows in FIGS. 4A and 4B) through the adjacent pallets (150). By contrast, standard containers or semi-trailers that include cooling capacity often use air delivery equipment located in the front of the unit. Thus, the air must travel to extreme distances through a small channel or plenum to reach and cool each pallet. Accordingly, pallets farthest away from the air delivery equipment receive less air flow and will be slower to cool and, thus, delay the conclusion of the cooling process. (See, e.g., FIGS. 7 and 8, which illustrate the air flow patterns for this conventional type of equipment.) However, the modified container or semi-trailer of the invention is modified to add supplemental air flow and cooling capacity that is adjacent to each pallet. Accordingly, the air flow is directed horizontally through each of the pallets (see, e.g., FIGS. 4A and 4B). This enhanced, direct air delivery approach ensures that each pallet receives the same increased capacity of air flow and then cools faster and more uniformly. In this manner, cooling can occur, and a gaseous, very small micron substance or vaporized sanitizer can be recirculated through the pallet and across the fruit to provide a "dry washing" step. For example, as shown in FIG. 4B, a treatment sprayer (140) can be included to provide this gaseous, very small micron substance, or vaporized sanitizer to the air flow plenum (120) to be recirculated through the pallets (150). Given the 60-minute or longer time duration for cooling, this exposure time enables use of lower concentrations of active sanitizer material to achieve the beneficial effect of reducing and/or neutralizing any spoilage organisms, while not damaging the fruit, vegetable, or other perishable. In particular, sanitizer efficacy is a function of concentration/strength of action and exposure time. Moreover, certain high concentrations of sanitizers and/or strong sanitizers could damage the product. Certain amounts or types of sanitizers could also damage the materials of construction of the container and/or the refrigeration equipment. Accordingly, the system allows for (i) using a lower or a milder level of sanitizer for a longer period of time during cooling, which enables an effective treatment, without the damage that is generally associated with short time/high concentration exposure, (ii) a controlled higher level of sanitizer with a carefully managed shorter period of contact time of sanitizer, and/or (iii) a short controlled exposure prior to deactivation during cooling as may be required to enable an effective treatment, without the damage that is generally associated with short time/high concentration exposure. This could not occur in conjunction with any other commercial cooling process that uses high concentrations of sanitizing materials even in short time bursts. For example, current cooling systems using tarp plenums within an open atmosphere environment with operating personnel are not capable of this process. According to another embodiment of the invention, special coatings can be applied to the surface of the interior of the container or semi-trailer and/or construction materials such as, e.g., stainless steel are used that are resistant to damage from strong sanitizers can be used to allow for these types of sanitizing treatments for certain types of products.

While not required for the process, a shuttle conveyor system (160) that moves pallets (150) in and then back out of the container (100) offers site flexibility to eliminate forklifts driving into the container (100). In addition, drop off and pickup on the exterior conveyor (160) enables faster loading and discharge.

Figure 9:
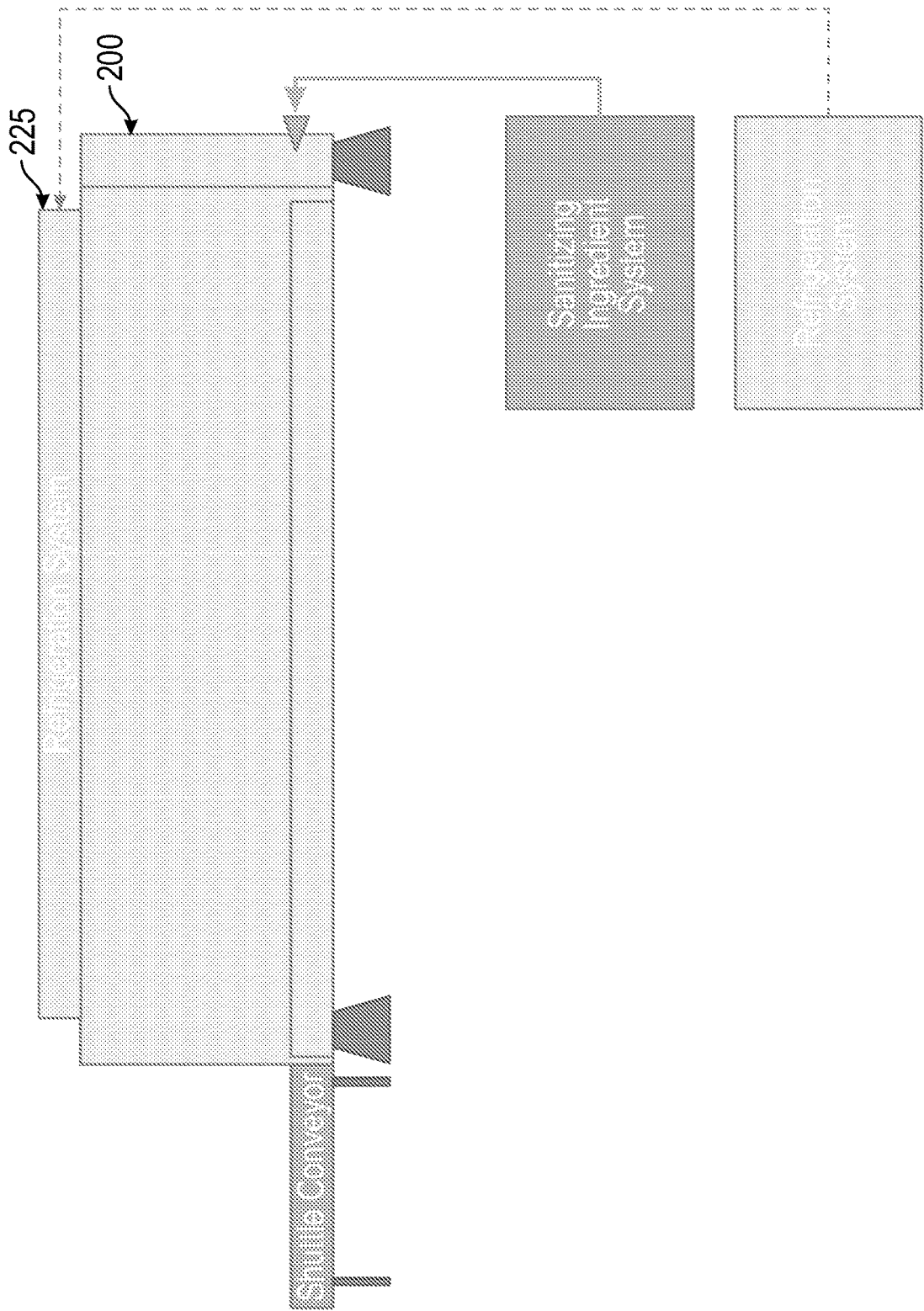
FIG. 9 is a diagram illustrating an alternative embodiment of a precooling system of the invention using a 40-foot-high cube reefer container (or a 53-foot-high semi-trailer) to create pop-out sides that can provide sufficiently wide air supply plenum to increase the capacity of the unit.

FIGS. 9, 10A, and 10B illustrate an alternative embodiment of a precooling system of the invention in which the 40' container (200) (or, alternatively, a 53' semi-trailer) are modified to create "pop out" sides (220) that can provide sufficiently wide air supply plenum to increase the capacity of the unit to at least 18 to 24 pallets (250). One or more cooling systems (225) would be mounted above the container (200), and the ceiling would be modified (see, e.g., baffles (290)) to enable the air recirculation (horizontal and/or vertical arrows) depicted in FIGS. 10A and 10B. The one or more cooling systems (225) include fans (222) and cooling coils (224) to provide the necessary cooling capacity to the container (200). Under certain conditions, a standard width container (200) or a semi-trailer does not provide enough space in the plenums, nor return air column to effectively distribute the necessary air flow to cool the fruit in the time needed. Accordingly, the "pop-out" sides (220) provide this necessary air flow for cooling the fruit in the time needed. According to one embodiment, the "pop-out" sides (220) can "slide in" and lock for transport and "slide out" and lock during operation. According to this embodiment, greater capacity and uniformity for cooling, sanitizing, and/or ripening is possible, as well as a higher volume of more efficient air flow. Additionally, according to this embodiment, a treatment sprayer (240) can be included to provide a gaseous or vaporized sanitizer to the "pop-out" sides (220) or air flow plenum to be recirculated through the pallets (250).

Again, while not required for the process, a shuttle conveyor system (260) that moves pallets (250) in and then back out of the container (200) offers site flexibility to eliminate forklifts driving into the container (200). In addition, drop off and pickup on the exterior conveyor (260) enables faster loading and discharge.

Figure 11C:
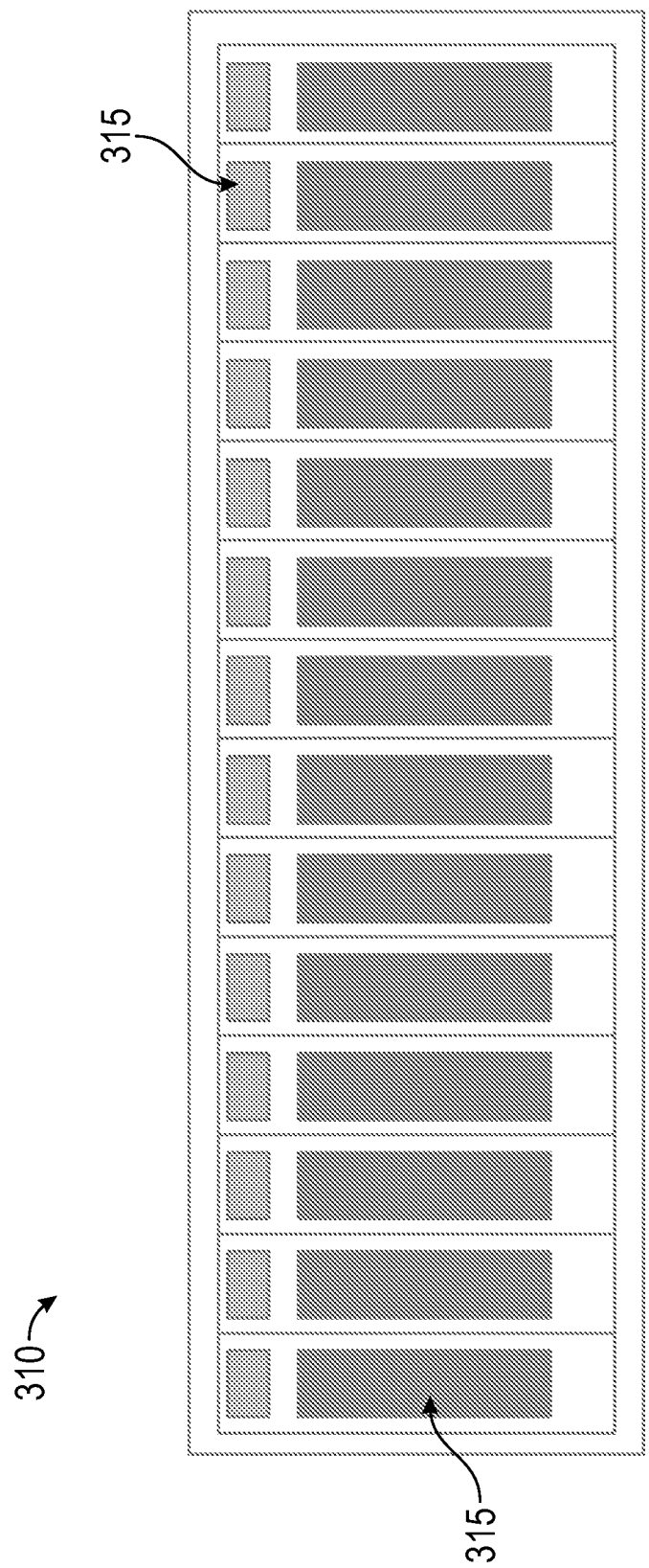
FIG. 11C is a diagram illustrating the modifications to the container of FIGS. 11A and 11B, to cut out sections of the insulated wall to enable air to flow from the refrigeration unit to the pallets of perishable product and then return over the top of the pallet back to the refrigeration unit.

FIGS. 11A and 11B illustrate an alternative embodiment of a precooling system of the invention in which the refrigeration units (320) and/or pressure air equipment (320) are clipped onto the sides (310) of the container (300). The refrigeration units (320) and/or pressure air equipment (320) includes, for example, fans (322) and cooling coils (324) to provide the necessary cooling capacity to the container (300). Openings (315) in the sidewalls (310) (see, e.g., FIG. 11C) enable the pallets (350) to be placed at the side of the container (300). Air is forced through the pallets (350) of cartons to the center open column (see horizontal and/or vertical arrows in FIGS. 11A and 11B). The air returns up and over the pallets (350) back to the refrigeration units (320). For relocation to the next seasonal harvest area, the refrigeration units (320) are un-clipped, stored inside the container (300), and then moved to the next site for reassembly. Additionally, according to this embodiment, a treatment system or spray system (340) can be included to provide a gaseous, suspended ultra to small micron substance treatment or vaporized sanitizer to be drawn through the products by the fans of the refrigeration units (320) to be recirculated through the pallets (350).

Again, while not required for the process, a shuttle conveyor system (360) that moves pallets (350) in and then back out of the container (300) offers site flexibility to eliminate forklifts driving into the container (300). In addition, drop off and pickup on the exterior conveyor (360) enables faster loading and discharge.

FIG. 11C illustrates the modifications to the sidewalls (310) of the container (300) of FIGS. 11A and 11B to cut out sections of the insulated sidewall(s) (310) to provide openings (315) to enable air to flow from the refrigeration unit (320) to the pallets (350) of perishable product and then return over the top of the pallet (350) and back to the refrigeration unit (320). The cut-out sections or openings (315) can be further modified with a vent cover design to open and close, and adjust the direction and amount of air flow to the pallets (350).

Figure 12A:
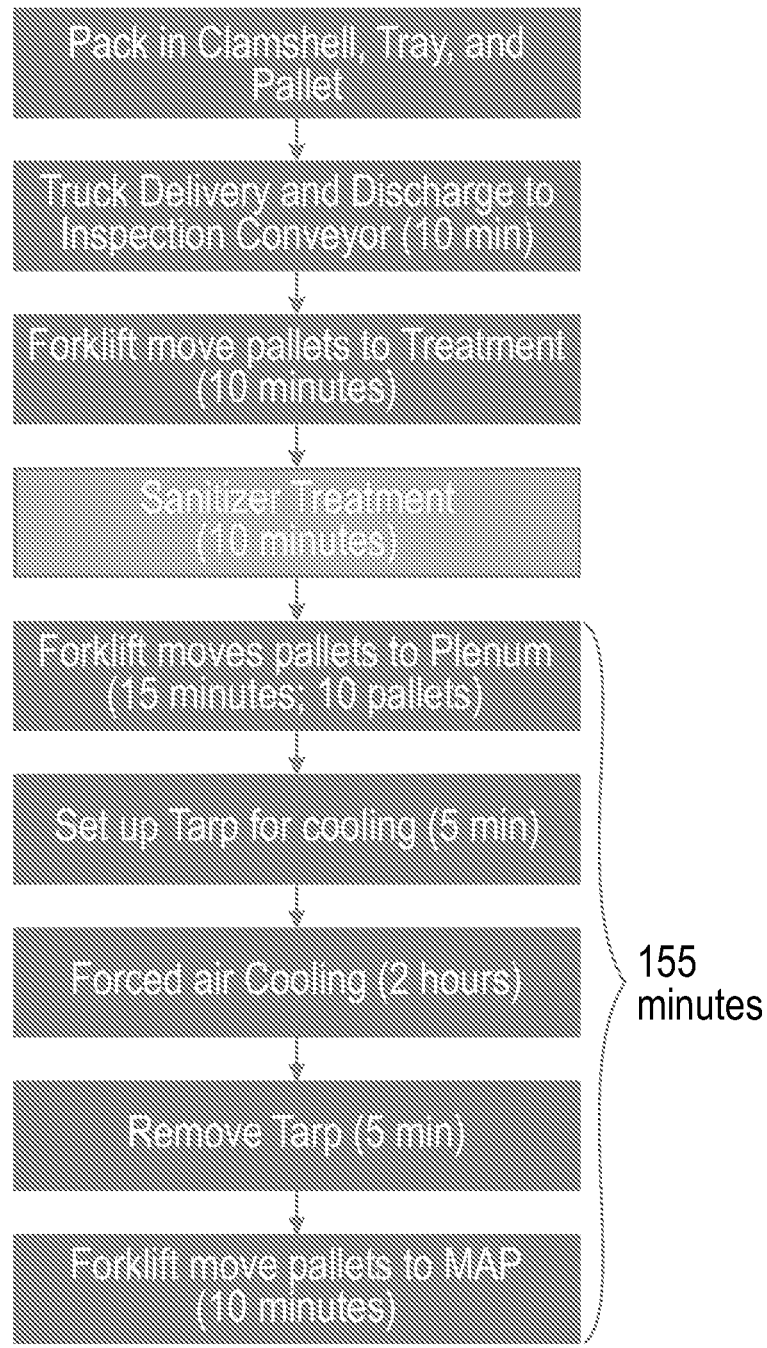
FIG. 12A is a flowchart of an embodiment of the inventive process when the container is used for sanitizing alone, and not cooling.

FIG. 12A illustrates a flowchart of an embodiment of the inventive process in which a modified container is used for sanitizing alone, and not cooling. This process would use one of the designs for the modified containers or semi-trailers described above. As shown, the sanitization can occur before cooling. The sanitization treatment within the container could also occur after cooling.

Figure 12B:
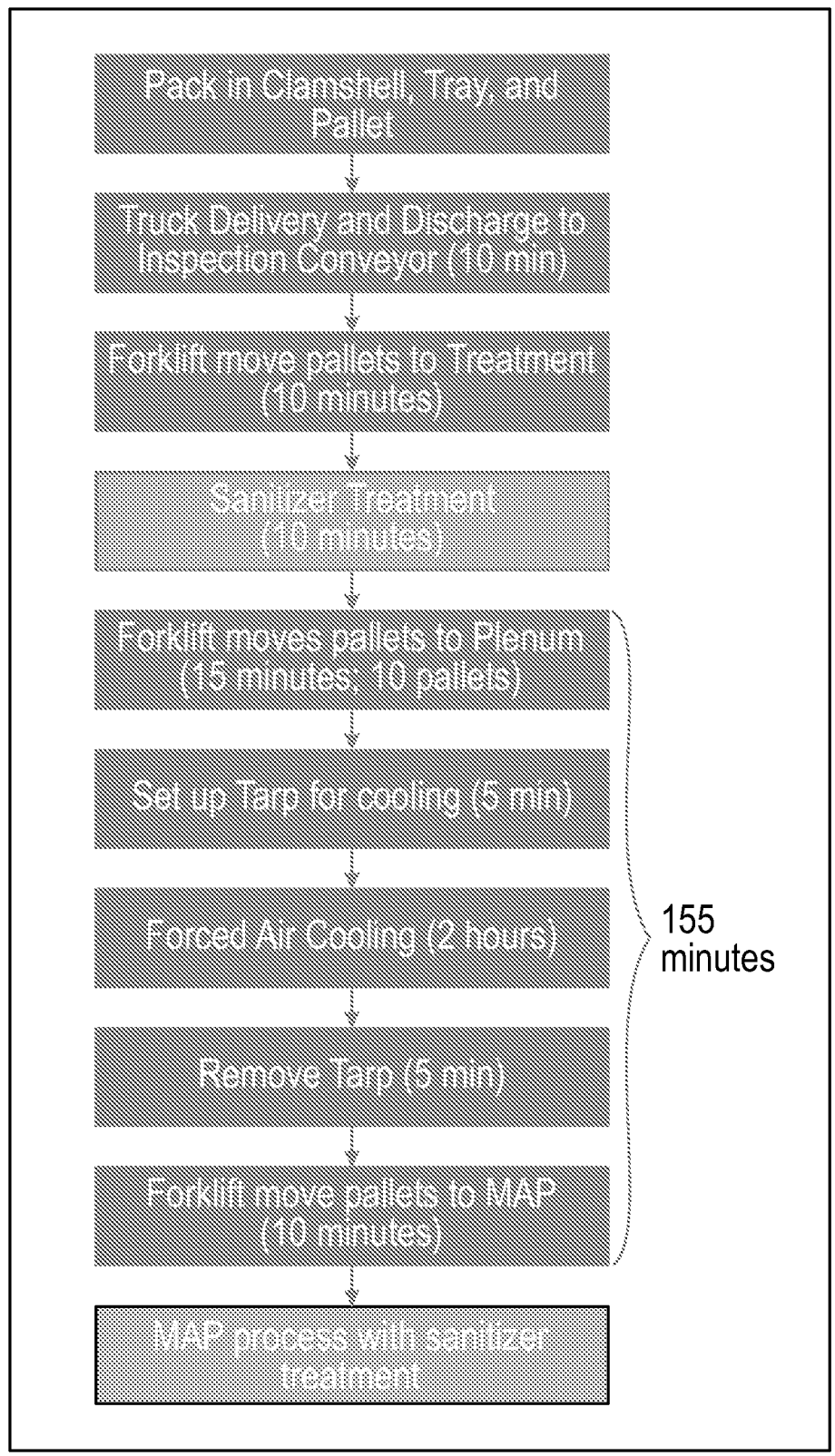
FIG. 12B is a flowchart of an embodiment of the inventive process in which a sanitizing treatment occurs before cooling and then a second sanitizing treatment occurs within the MAP (modified atmosphere pallet) process.
Figure 12C:
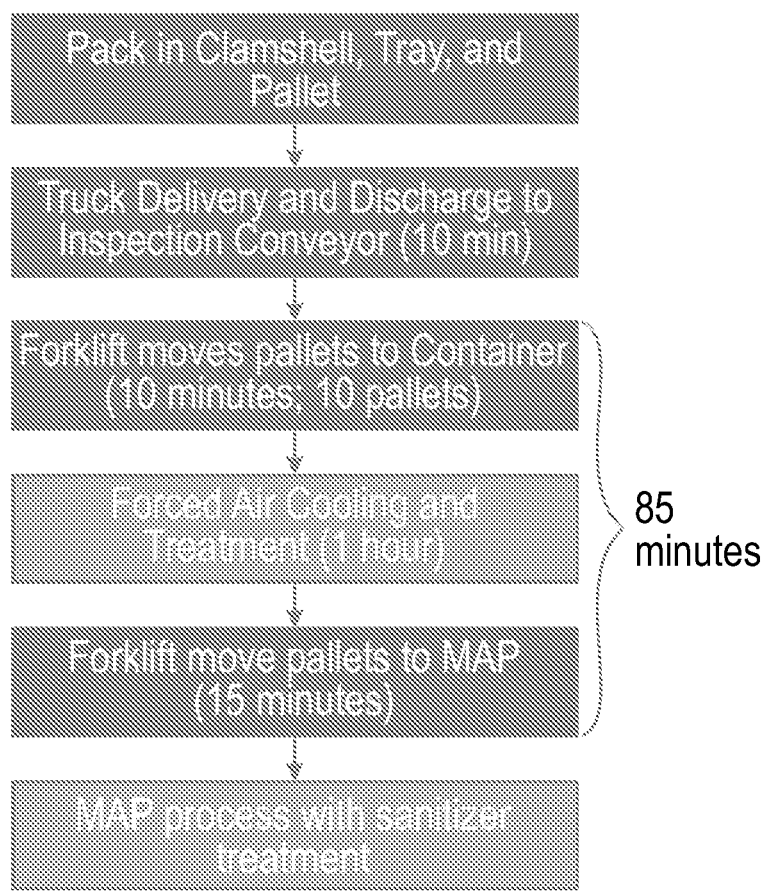
FIG. 12C is a flowchart of an embodiment of the inventive process that includes a combination of multiple sanitizing treatments, with a first sanitizing treatment occurring within a cooling step in a modified container of the invention.

FIG. 12B illustrates a flowchart of an embodiment of the inventive process in which a sanitizing treatment occurs before cooling and then a second sanitizing treatment occurs within the MAP (modified atmosphere pallet) process. FIG. 12C illustrates a flowchart of an embodiment of the inventive process having a combination of multiple sanitizing treatments, with the first sanitizing treatment occurring within a cooling step in a modified container (as described above). According to this embodiment, a cooling step ("forced air cooling") in a modified container occurs for one-hour (60-minutes), which is followed by or in combination with a MAP process with sanitizer treatment. Because of the 60-minute residence time for cooling and receiving the sanitizing treatment, this combination process that includes a MAP sanitizer step should yield the best overall results. In particular, the 60-minute treatment during cooling enables a milder but longer exposure time for the sanitizer application. Additionally, the MAP sanitizer treatment adds a sanitizer that could be synergistic or that can impact any residual spoilage or pathogenic organisms present. For example, some sanitizing materials, such as essential oils, can provide sanitizing effects and impact over the days that it takes to deliver the sealed pallet to a customer. As further shown in FIG. 12C, this overall process is achieved with an 85-minute process time.

FIG. 13 illustrates a typical or conventional cooling, storage, and shipping facility (400) for perishable produce or product. Note that the space (450) allocated for pre-cooling and pallet movements associated therewith requires that about 40% of the facility be available for cooling in a refrigerated space. Accordingly, a large amount of the facility space has to be reserved for pre-cooling product in an efficient manner.

Figure 14:
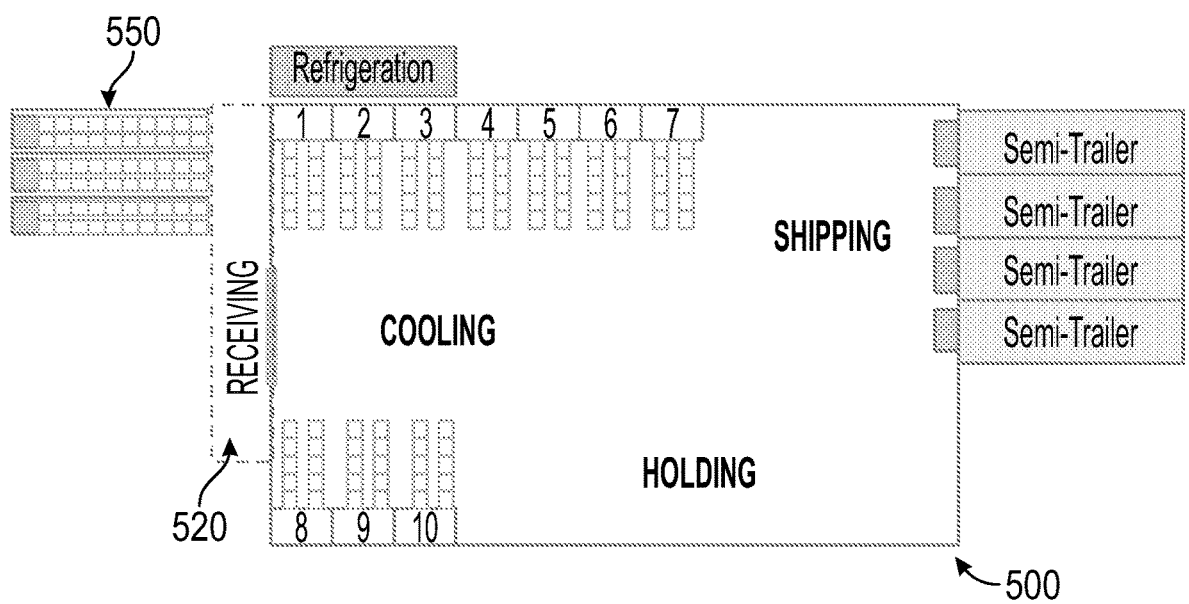
FIG. 14 is a diagram illustrating an embodiment of the invention in which containers are positioned for implementing a sanitizing treatment and/or cooling before entry into the warehouse.

FIG. 14 illustrates an embodiment of the invention using mobile containers (550) to apply the sanitizing treatment before cooling and storage in the warehouse (500). Note that three containers (550) easily match with ten tarp plenums that require two hours to cool product. In the event of peak production requirements, the facility can add more mobile containers (550) staged adjacent the receiving dock (520).

Figure 15A:
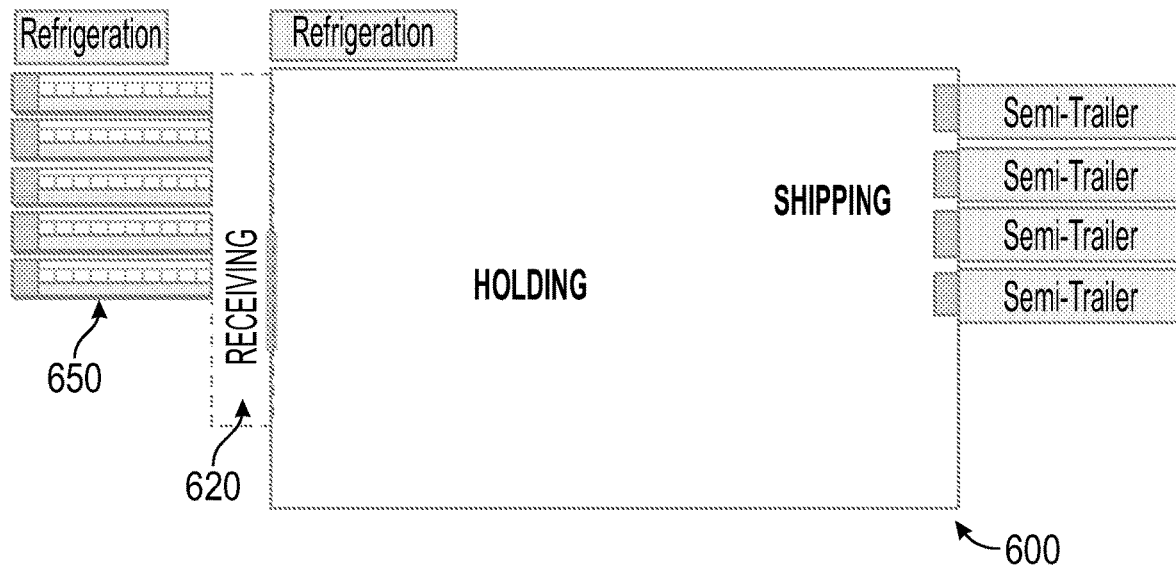
FIG. 15A is a diagram illustrating an embodiment of the invention in which the modified containers are used to cool and to apply the sanitizing treatment before storage in the warehouse, thereby eliminating the warehouse's current tarp cooling systems.

FIG. 15A illustrates an embodiment of the invention using modified containers (650) to cool and to apply the sanitizing treatment before storage in the warehouse (600), eliminating the warehouse's current tarp cooling systems. Note that five containers (650) cooling at least nine pallets in one hour are able to approximately replace the ten tarp plenums that require two hours to cool the same amount of product. This modification opens up about 40% of the warehouse (600) for additional storage. This enables avoiding the use of racking, which slows pallet movement and turnover in the warehouse (600). The perishable product has been cooled as intended and received a sanitizing treatment. The warehouse storage temperature will not be impacted by production surges. In the event of peak production requirements, the facility can add more mobile containers (650) staged adjacent to the receiving dock (620). If the containers (650), modified to contain at least 40 pallets (see, e.g., FIGS. 10A, 10B, 11A, and 11B), were used, then the number of containers (650) could be reduced, or the capacity of the warehouse operation could be significantly increased.

Figure 15B:
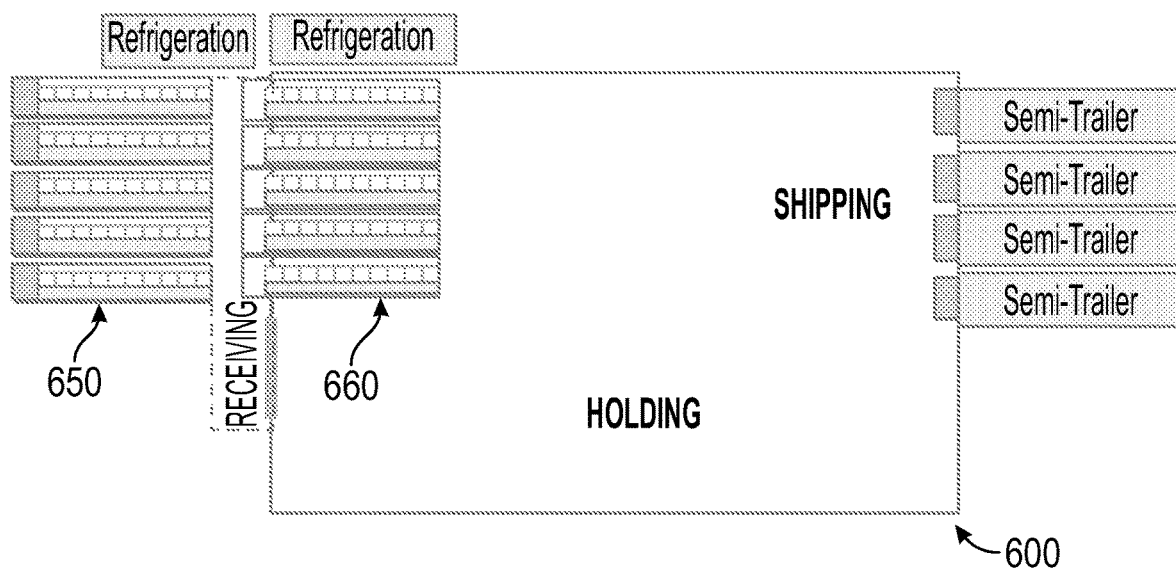
FIG. 15B is a diagram illustrating an embodiment of the invention in which two separate system designs are provided.

FIG. 15B illustrates an embodiment for two separate system designs. According to one embodiment, there are five exterior precooling and treatment systems (650) and five pass-thru precooling and treatment systems (660) that are located within the warehouse (600). In another embodiment, the exterior systems (650) are used for precooling or treatment, and then the pass-thru systems (660) are used for the other complementary step, e.g., treatment or precooling. This sequential or tandem use of the mobile systems would allow for separation of the cooling and sanitizing treatments for situations where the sanitizers cause undesirable amounts of freezing on the refrigeration coils and/or corrosion on the coils or other sensitive components within the container.

As discussed above, in the embodiments of FIGS. 10A, 10B, 11A and 11B, a shuttle conveyor is illustrated for the purpose of easily moving pallets into and out of the modified container. This shuttle conveyor could also be included with the embodiments of FIGS. 15A and 15B (as well as FIGS. 16A-16C, as described below), as this enables pallet movement and positioning without the need and time expense to physically drive the pallets into and out of the container. The shuttle conveyor can be either an "in-and-out" design from one end, or a pass-thru design where the pallets are loaded at one end and removed from the other end. This design has advantages from other more continuous conveying and cooling systems in use today that have complicated materials and components for continuously moving and sealing plenums to pallets. Those components lead to expensive construction and maintenance expenses and have some limitations in the use of sanitizing materials for product treatment. This design is simpler and less costly to construct and maintain. Additionally, a single treatment and/or cooling zone can be utilized for either one continuous treatment or stages/cycles of treatment that can accomplish different functional benefits.

Figure 16A:
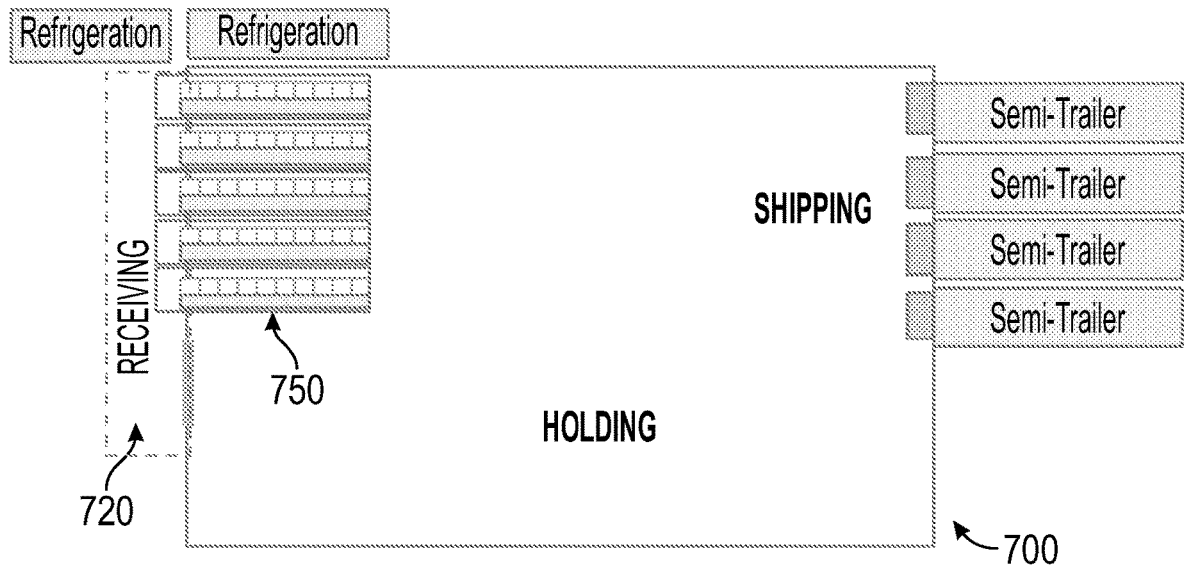
FIG. 16A is a diagram illustrating an embodiment of the invention in which the modified containers receive the warm product on the receiving dock, cool and sanitize the product, and then remove the product from within the warehouse (e.g., a "pass-thru" system).

FIG. 16A illustrates an embodiment of the invention using modified containers (750) receiving the warm product on the receiving dock (720), cooling and sanitizing the product, and then the product is removed from within the warehouse (700). By keeping the warehouse (700) closed during the receiving steps, the warehouse (700) is able to control its temperature more accurately and efficiently. The receiving door is not opened for forklifts to enter and leave, thus eliminating this intrusion of warm outside air and the escape of cold air. Storage space in the cold warehouse (700) is still increased over the current base design.

Figure 16B:
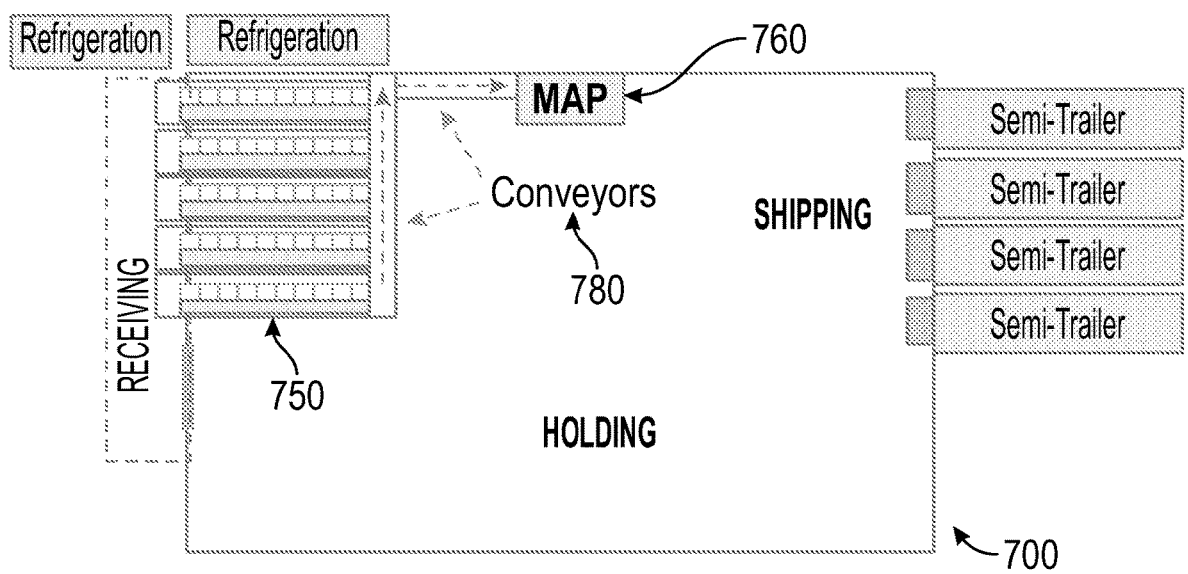
FIG. 16B is a diagram illustrating an embodiment of the invention in which an MAP application system is connected via a set of conveyors to complete the preparation of the cooled and ready for shipment pallet.
Figures 19, 20:
FIG. 19 illustrates an embodiment of the invention that uses connecting automated conveyors to physically move pallets from one location to the next, including through doors, such as described in the various embodiments for the invention.
FIG. 20 is a table of information from the University of California at Davis illustrating the dramatic impact of product temperature on rate of respiration.

FIG. 16B illustrates an embodiment of the invention in which a MAP application system (760) is connected via a set of conveyors (780) to the modified containers (750) to complete the preparation of the cooled and ready for shipment pallet (see, e.g., FIG. 19). Through this embodiment and set-up, a pallet handling step from the mobile cooler to the MAP system is eliminated. This further reduces the storage space required for pallets to be staged during the processing steps. Pallets move to the MAP process immediately after cooling and can then be loaded directly to transportation trucks in a semi-automatic process.

Figure 16C:
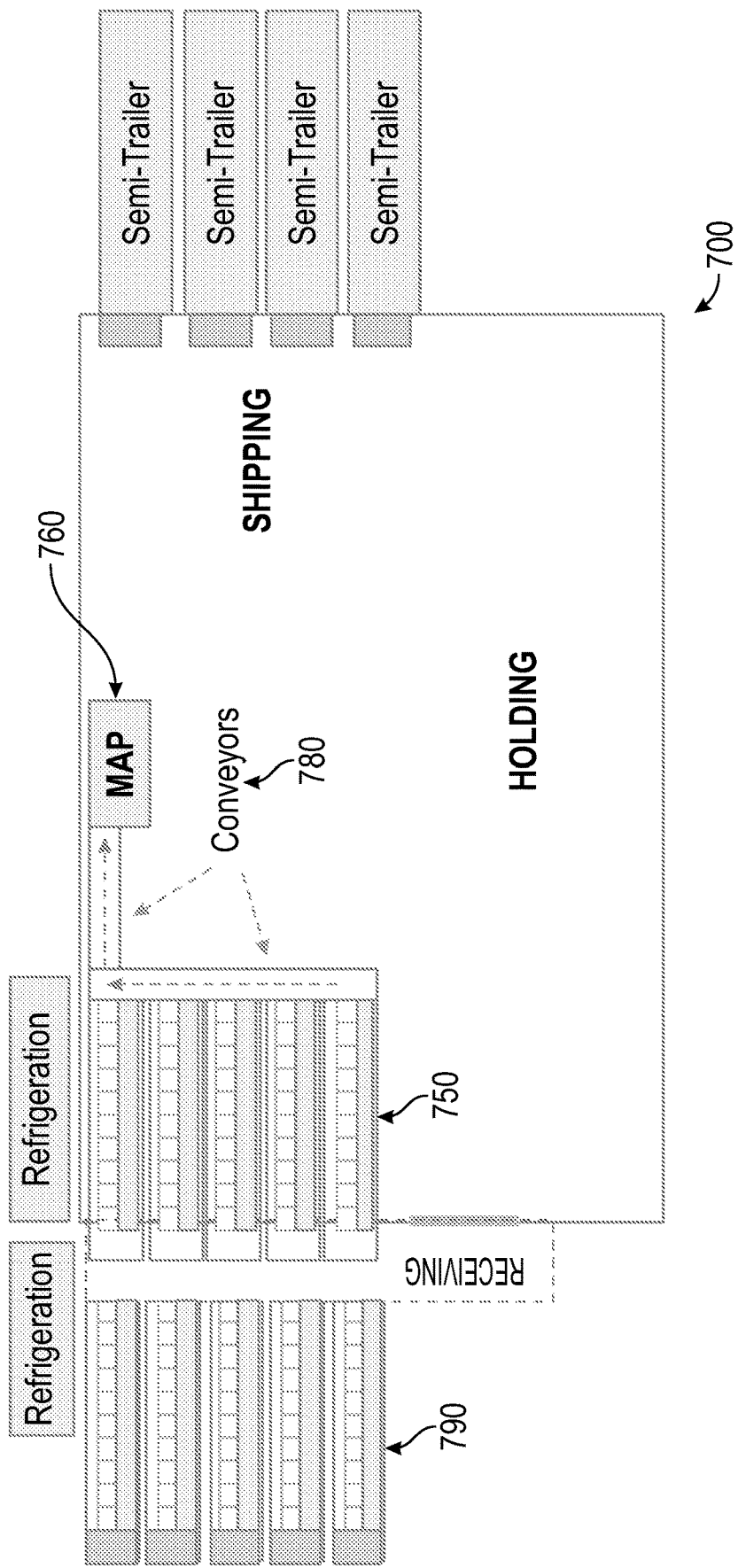
FIG. 16C is a diagram illustrating an embodiment of the invention in which a combination of exterior and pass-thru systems are used for tandem cooling, sanitizing treatment, and then MAP.

FIG. 16C illustrates an embodiment of the invention in which a combination of exterior systems (790) and pass-thru systems (750) are used for tandem cooling and sanitizing treatment, and then connected to an MAP system (760). By coupling mobile systems (750 and 790), conveyors (780), and an MAP process (760) in this way, maximum cold storage space is provided, while eliminating an operational handling step requiring a forklift and labor, and minimizing any contamination that could occur within the cold warehouse (700). Moreover, the sealed MAP pallet is ready for shipment or short term cold storage.

With the cooling and handling steps minimized in the use of the mobile containers and conveyors, it can be conceived that the cooling and treatment operation can be set up at simple packing houses and enable the product to completely by-pass the need to go to the cooling warehouses, saving important process time and expense.

Figure 17:
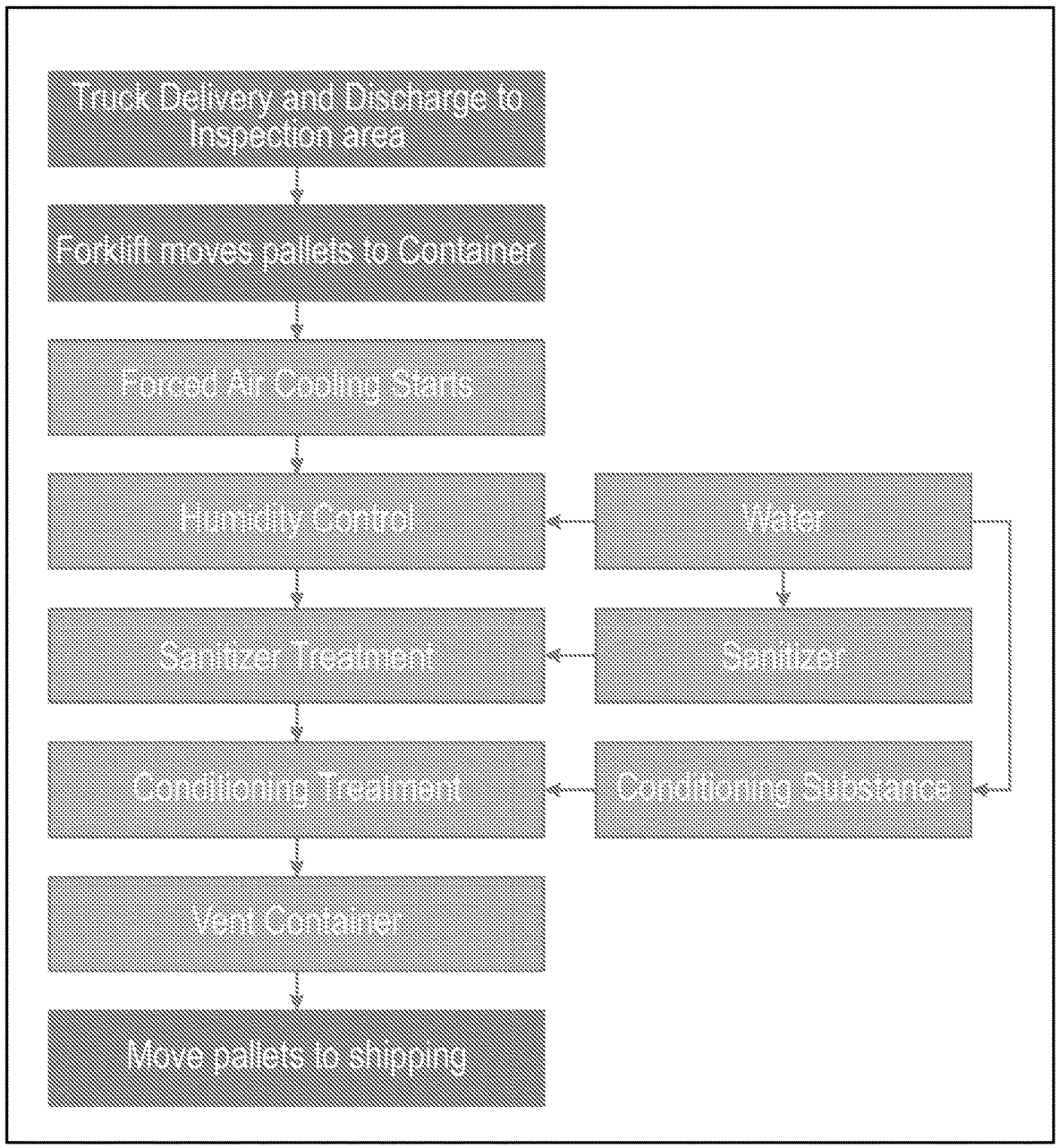
FIG. 17 is a flowchart of an embodiment of the inventive process using the mobile container system with exceptional refrigeration and air flow to more accurately and efficiently control the quality conditioning and ripening of high climacteric perishable produce items.

FIG. 17 illustrates a flow chart of an embodiment of the invention process using the mobile container with exceptional refrigeration and air flow to add a conditioning or ripeness management substance to improve the organoleptic properties of the perishable. Importantly, the refrigeration and air flow capacity will exceed that of the standard container, enabling it to control the heat generated by the ripening of climacteric perishable items.

Figure 18:
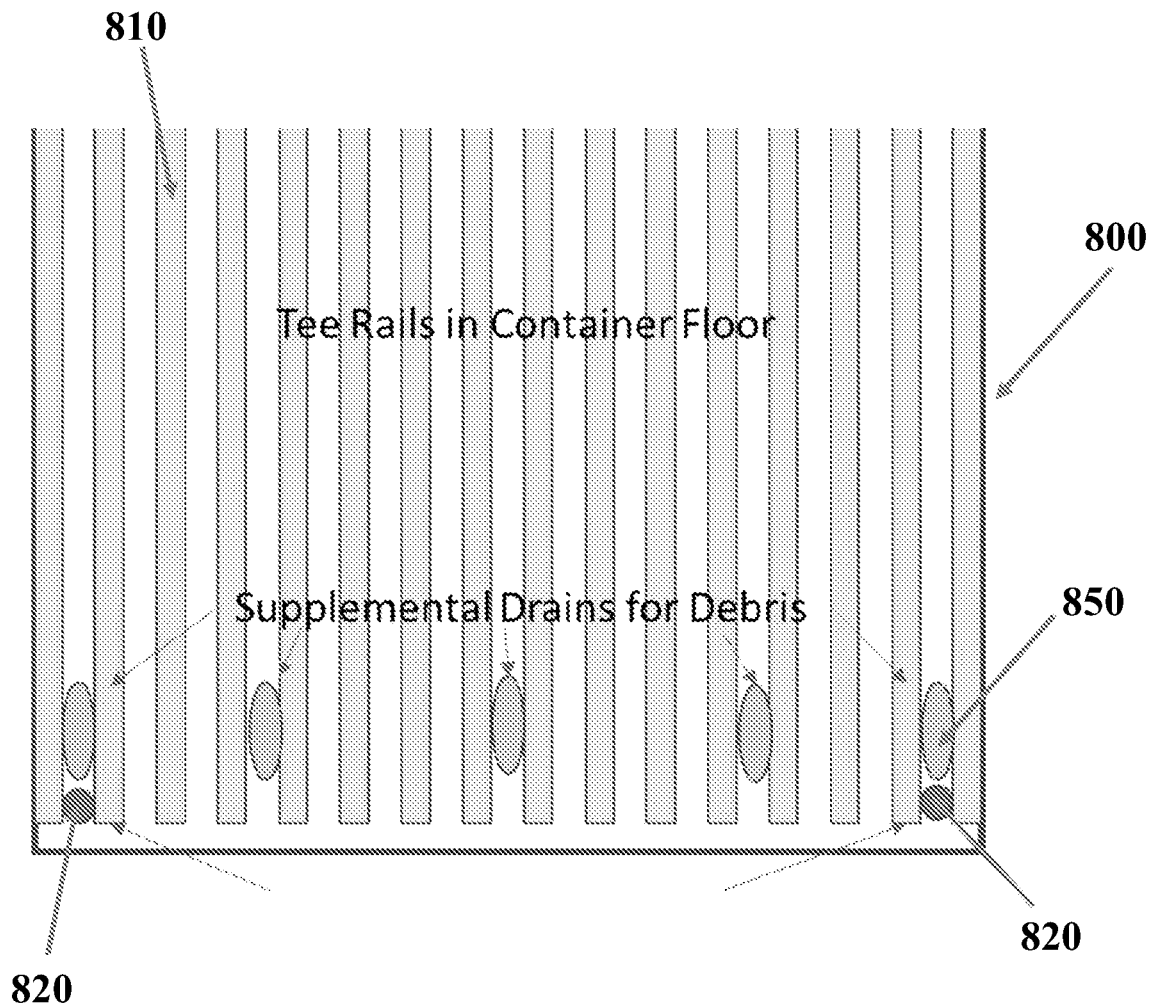
FIG. 18 is a diagram illustrating an embodiment of the invention in which supplemental drains are included within the floor of the precooling system or container for removal of debris remaining in the container from field packed product.

FIG. 18 illustrates an embodiment of a modified container according to the invention in which a portion of the floor (800) of the container includes tee rails (810), as well as container floor drains (820) and supplemental drains (850).

The supplemental drains (850) are included for removal of debris remaining in the container from field packed product. These drains (850) are able to be sealed, but also opened up to aid in the cleaning of pieces of dirt and wood. As discussed above, these supplemental drains (850) are provided in addition to the container floor drains (820) that are included with the system (see also, e.g., container drains (180, 280, 380) provided with the containers (100, 200, and 300) of the embodiments illustrated in FIGS. 4A, 4B, 10A, 10B, 11A and 11B).

Figure 23:
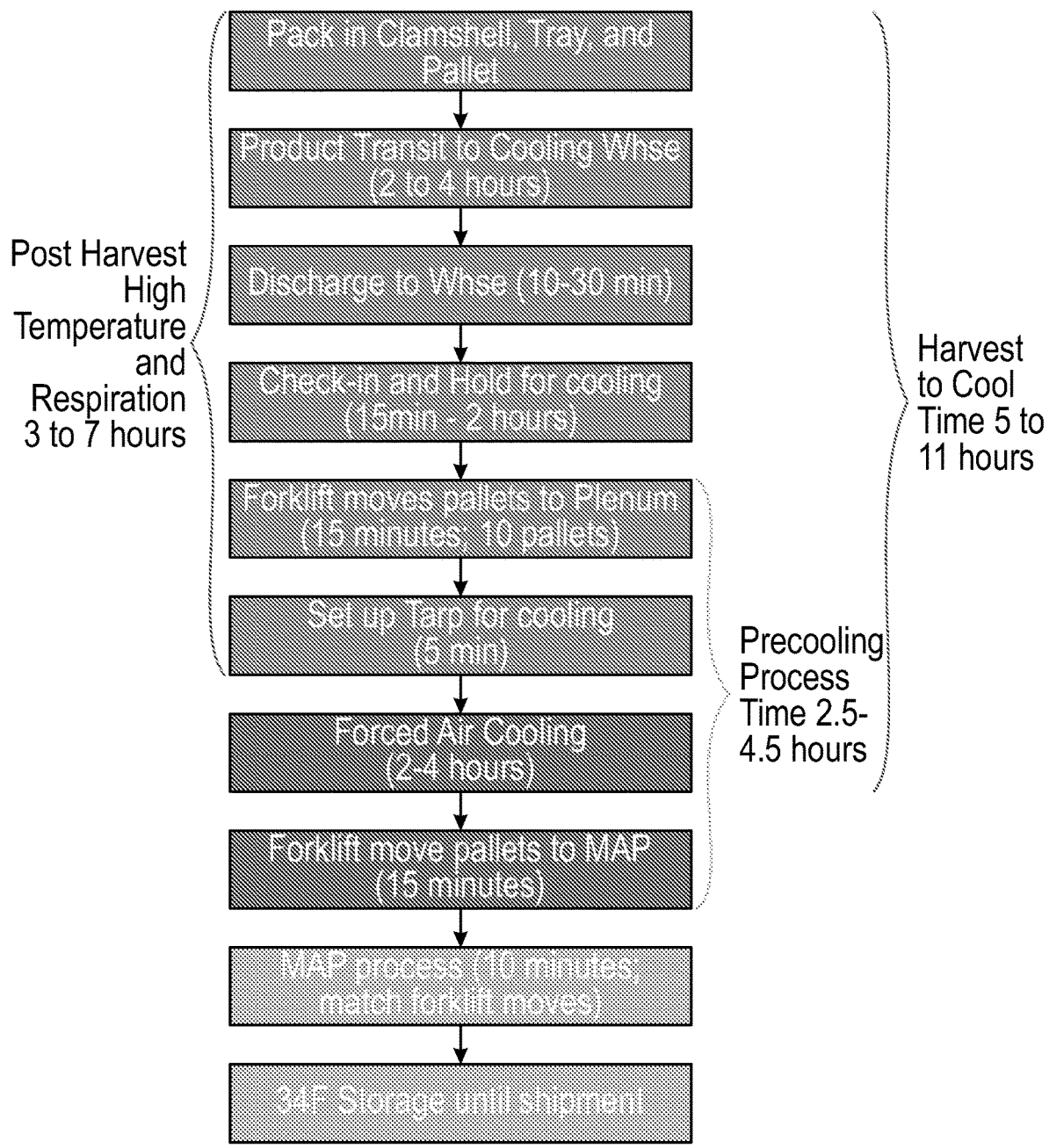
FIG. 23 is a flowchart of the current process to pack and transfer palletized containers of perishable product to a warehouse, cool the product to an intended temperature, moving the pallets to add a modified atmosphere (MAP), and then moving the pallets to storage where the pallets are maintained at 32° F. to 34° F. or another prescribed temperature until shipment.

FIG. 23 is a flowchart of a yet another typical or conventional berry cooling process. In this process, a perishable product (e.g., berries) is packed at the harvesting field and then must be moved or transported to a warehouse (which generally takes about two (2) to four (4) hours). The pallets of product are usually held before cooling, until a forklift can move the pallets to the area of cooling. As in the process of FIG. 1, this process uses tarps for vacuum plenums within a cold storage facility. The plenum fan sucks air through cartons or pallets of product staged at the plenums ("forced air cooling"). Cooling continues until the product reaches the intended temperature (usually 32-34° F.). The two (2) hours to four (4) hours generally required to cool the pallets of product ("forced air cooling"), along with the pallet movements and tarp plenum setup, results in a total time until delivery to and staging for a MAP (modified atmosphere pallet) of 2.5 to 4.5 hours. As further shown in FIG. 23, the time between harvesting the product to the time the product even begins the cooling process via "forced air cooling" is about 3 to 7 hours. Moreover, as shown in FIG. 23, the overall "harvest to cool time" is about 5 to 11 hours.

Figure 24:
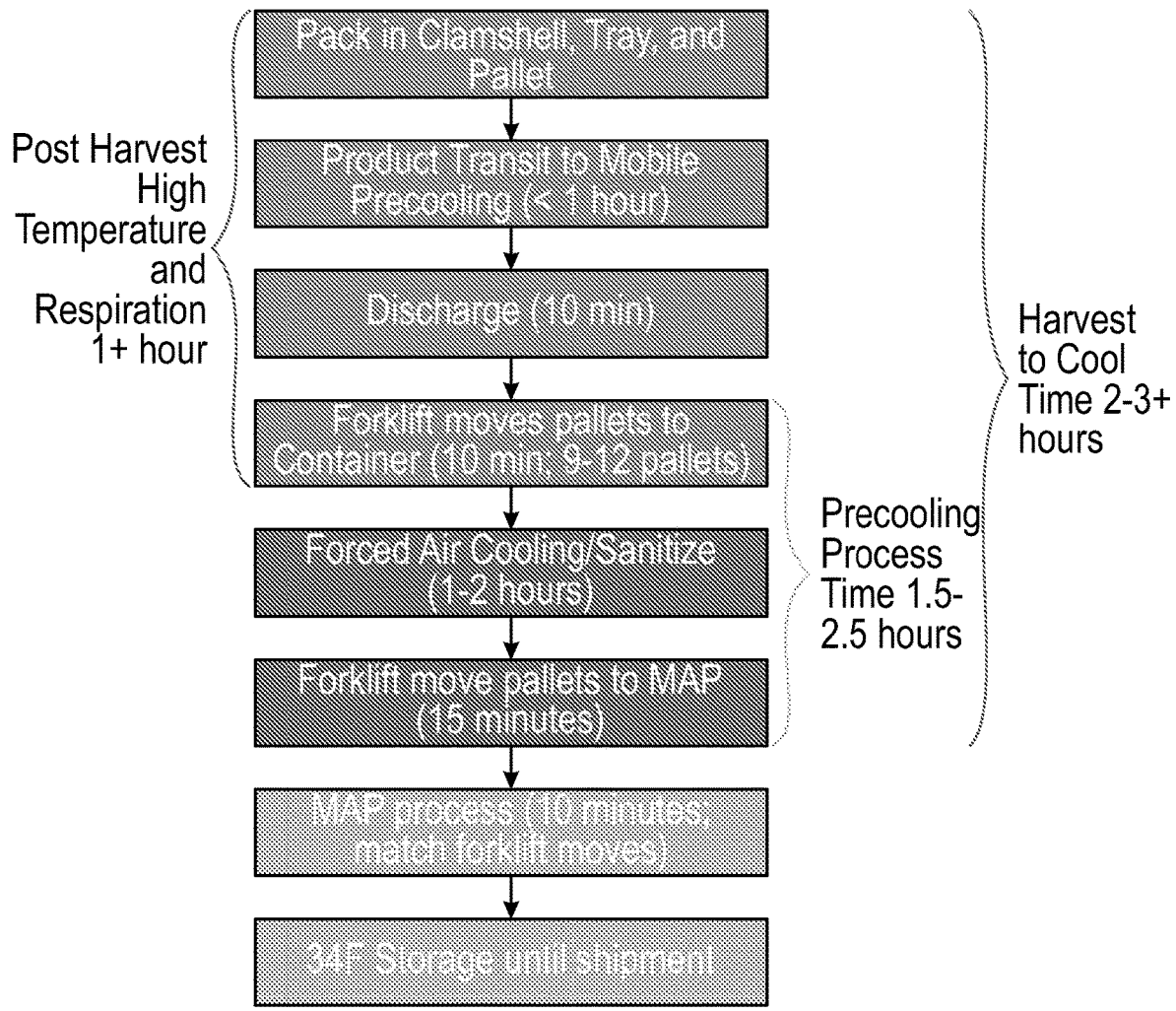
FIG. 24 is a flowchart of an embodiment of the inventive process using mobile precooling at a harvest site, moving the pallets to add a modified atmosphere (MAP), and then moving the pallets to storage where the pallets are maintained at 32° F. to 34° F. until shipment.

FIG. 24 is a flowchart of an embodiment of the inventive process using a mobile container designed to cool the berries to an intended temperature within one (1) hour to two (2) hours, while also being able to provide a sanitizing treatment during that time period. In this process, a perishable product (e.g., berries) is packed at the harvesting field and then must be moved or transported to the mobile container that is positioned near the harvesting field (which generally takes less than one (1) hour). The pallets of product are then moved into the mobile container by, for example, a forklift. As in the process of FIG. 2, the pallets are cooled and sanitized/treated within the mobile container ("forced air cooling/sanitize"). Cooling continues until the product reaches the intended temperature (usually 32-34° F.), which generally takes around one (1) hour to two (2) hours. The one (1) hour to two (2) hours generally required to cool the pallets of product ("forced air cooling/sanitize"), along with the pallet movements, results in a total time until delivery to and staging for a MAP (modified atmosphere pallet) of 1.5 to 2.5 hours. As further shown in FIG. 24, the time between harvesting the product to the time the product begins the cooling process via "forced air cooling" is a little over one (1) hour, which is significantly less than the 3 to 7 hours for the time between harvesting the product to the time the product begins the cooling process of the typical cooling process shown in FIG. 23. Moreover, as shown in FIG. 24, the overall "harvest to cool time" is about 2 to 3 hours, which, again, is much faster than the 5 to 11 hours of the typical cooling process shown in FIG. 23.

Figure 25:
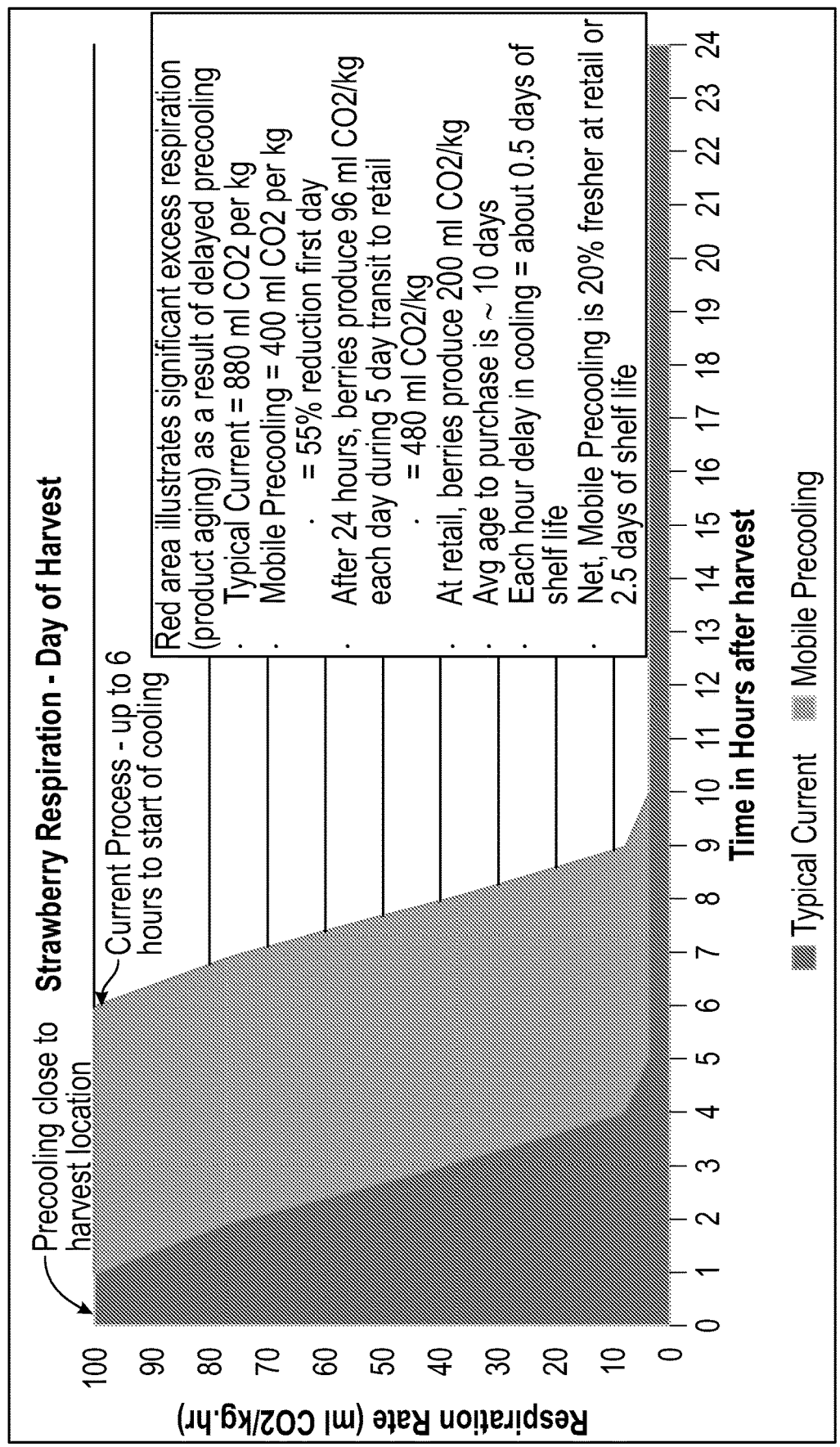
FIG. 25 is a graph illustrating the differences in the time to cool a perishable product (e.g., strawberries) from the day of harvesting, between current cooling processes and the inventive precooling process according to an embodiment of the invention.

Further benefits of the inventive system and process are illustrated in FIGS. 25 and 26. For example, FIGS. 25 and 26 illustrate the differences in product respiration with respect to the "harvest to cool time" of the precooling process of the inventive system compared to the typical cooling process shown in, for example, FIG. 23. In particular, as shown in FIG. 25, the significant excess respiration of the product (also known as, e.g., "product aging") as a result of delayed precooling, which occurs with the typical cooling process shown in, for example, FIG. 23, results in less shelf life for the product (i.e., each hour of delay in cooling results in about 0.5 days of shelf life). Thus, as shown in FIG. 25, the precooling process of the inventive system provides a product that is at least 20% fresher or has 2.5 additional days of shelf life. Moreover, as shown in FIG. 26, depending on the time of day for the harvest, even more shelf life is preserved using the precooling process of the inventive system, as compared to the typical cooling process shown in, for example, FIG. 23, due to at least the significant decreases in the "harvest to cool time" of the precooling process of the inventive system. As further shown in FIG. 26, the precooling process of the inventive system further provides for decreases in mold spores and/or spoilage organisms present on the product, as compared to the typical cooling process shown in, for example, FIG. 23.

Figure 27:
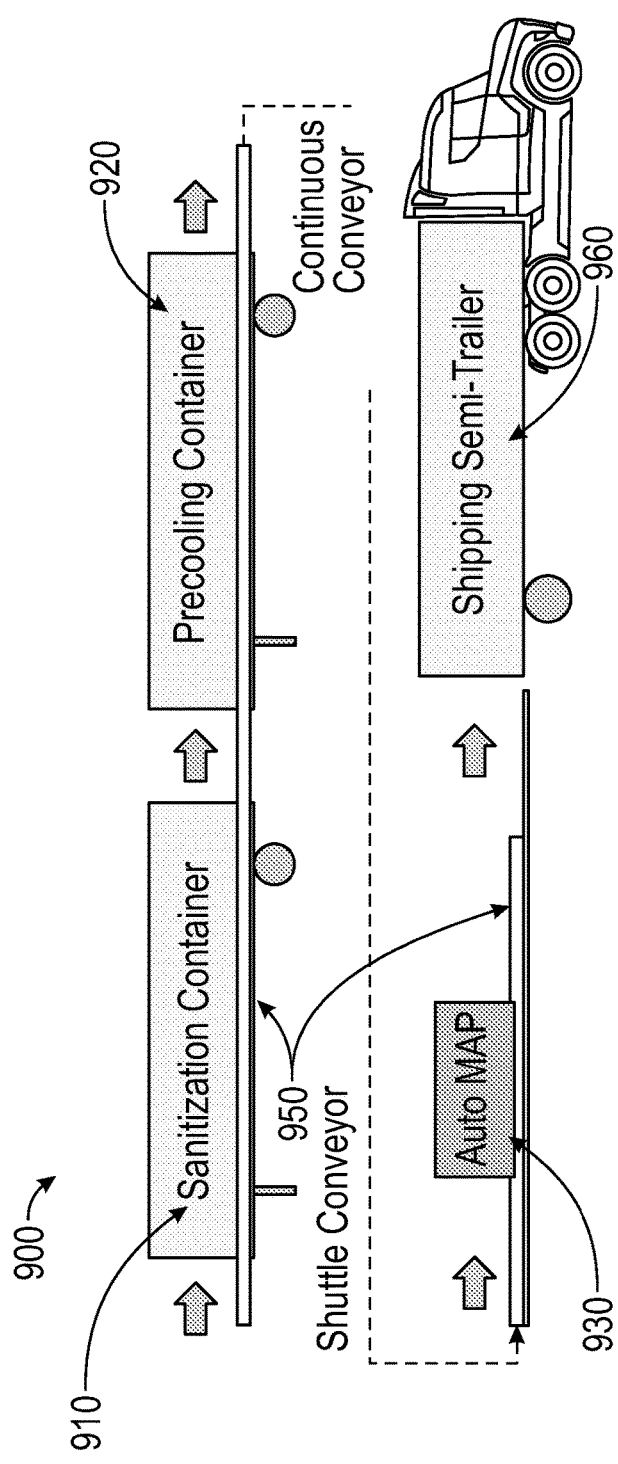
FIG. 27 is a diagram illustrating an embodiment of the invention in which a separate sanitization container, a separate precooling container, and a modified atmosphere pallet (MAP) application system are integrated into an overall system and process.

FIG. 27 illustrates an embodiment of an overall system (900) of the invention that includes an integrated sanitization, precooling and MAP process. In particular, the system (900) of FIG. 27 includes a separate sanitization container or unit (910), a separate precooling container or unit (920), and an automated, modified atmosphere pallet (MAP) application system (930). In this embodiment, pallets of perishable product are first placed within the separate sanitization container (910) for treatment with a sanitizer to reduce spoilage or pathogenic organisms that may be present on the surface of the product. Thereafter, the treated pallets of perishable product are moved or transported to the separate precooling container (920) to cool the product to a desirable temperature (e.g., 32-34° F.). After cooling, the perishable product is moved or transported to the automated, modified atmosphere pallet (MAP) application system (930) to add an MAP to the product. Although the MAP system (930) in this embodiment is automated, the MAP system (930) could also be semi-automatic. Once the pallets have completed the application in the MAP system (930), the pallets are finally moved or transported to a final shipping semi-trailer (960) for transportation to a storage warehouse or other location. According to this embodiment, pallets of perishable product are moved or transported between each of the separate containers or apparatus via one or more shuttle conveyors (950).

Figure 28:
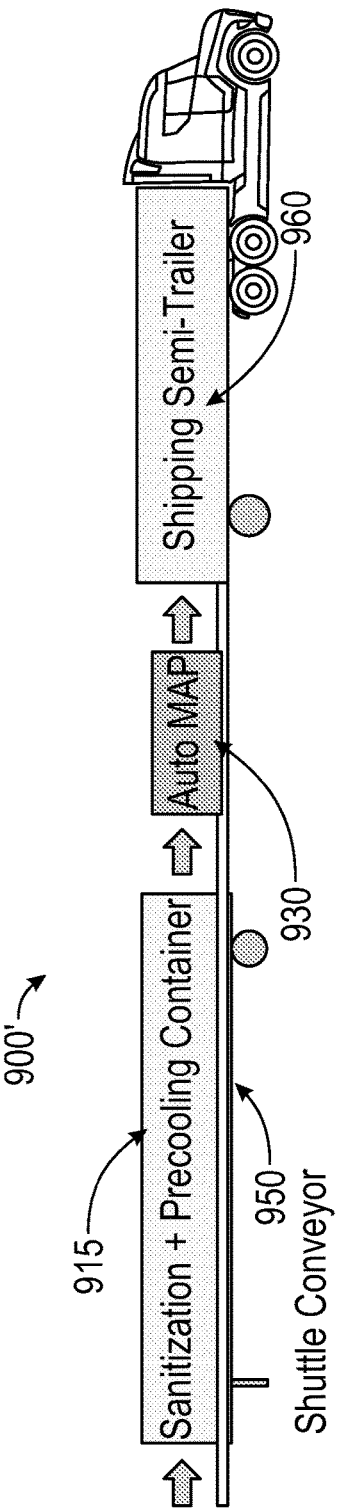
FIG. 28 is a diagram illustrating an embodiment of the invention in which a combined sanitization and precooling container and a modified atmosphere pallet (MAP) application system are integrated into an overall system and process.

FIG. 28 illustrates another embodiment of an overall system (900') of the invention that includes an alternative, integrated sanitization, precooling and MAP process. In this embodiment, the system (900') includes a combination sanitization and precooling container or unit (915) and an automated, modified atmosphere pallet (MAP) application system (930). According to this embodiment, pallets of perishable product are first placed within the combination sanitization and precooling container (915) for treatment with a sanitizer to reduce spoilage or pathogenic organisms that may be present on the surface of the product, while also cooling the product to a desirable temperature (e.g., 32-34° F.). After treatment and cooling, the perishable product is moved or transported to the automated, modified atmosphere pallet (MAP) application system (930) to add an MAP to the product. Although the MAP system (930) in this embodiment is automated, the MAP system (930) could also be semi-automatic. Once the pallets have completed the application in the MAP system (930), the pallets are finally moved or transported to a final shipping semi-trailer (960) for transportation to a storage warehouse or other location. According to this embodiment, pallets of perishable product are moved or transported between each of the containers or apparatus via one or more shuttle conveyors (950).

Figure 29:
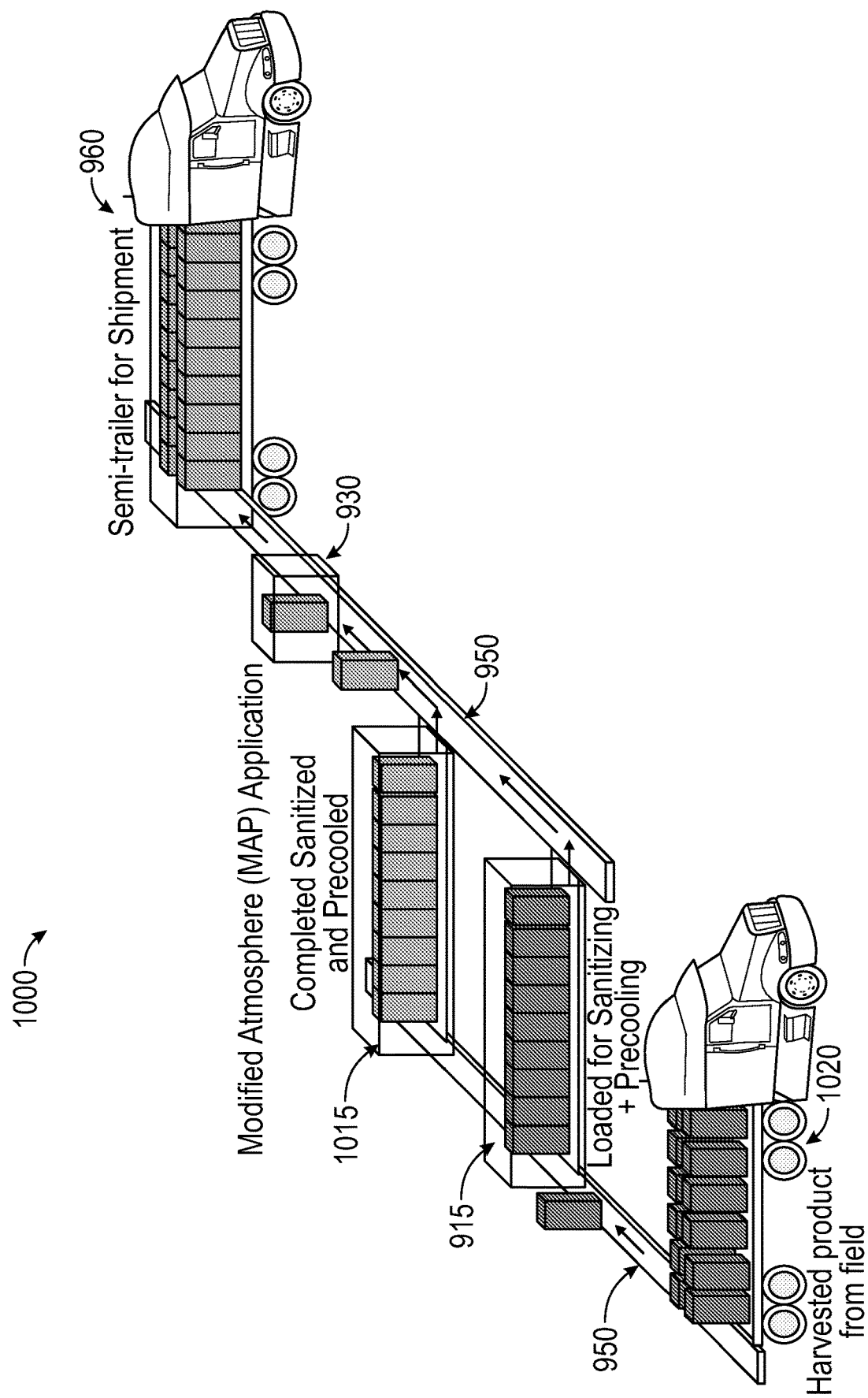
FIG. 29 is a diagram illustrating an embodiment of the invention in which a combined sanitization and precooling container and a modified atmosphere pallet (MAP) application system are integrated into an overall system and process, using cross-docking sanitization and cooling, for palletized product harvested from a field.

FIG. 29 illustrates an embodiment of an overall system (1000) of the invention that includes an integrated sanitization, precooling and MAP process with a cross dock arrangement. In this embodiment, the system (1000) includes a combination sanitization and precooling container or unit (915) just loaded, a completed sanitized and precooled container or unit (1015), and an automated, modified atmosphere pallet (MAP) application system (930). In this embodiment, pallets of harvested, perishable product are first transported to the system (1000) via a truck or semi-trailer (1020) from the field after harvesting of the product. The pallets of product are thereafter moved or transported to the combination sanitization and precooling container (915) for treatment with a sanitizer to reduce spoilage or pathogenic organisms that may be present on the surface of the product, while also cooling the product to a desirable temperature (e.g., 32-34° F.). After treatment and cooling is completed, the perishable product, as demonstrated in unit (1015), is moved to the automated, modified atmosphere pallet (MAP) application system (930) to add an MAP to the product. Although the MAP system (930) in this embodiment is automated, the MAP system (930) could also be semi-automatic. Once the pallets have completed the application in the MAP system (930), the pallets are finally moved or transported to a final shipping semi-trailer (960) for transportation to a storage warehouse or other location. According to this embodiment, pallets of perishable product are moved or transported between each of the containers or apparatus via one or more shuttle conveyors (950).

Figure 30:
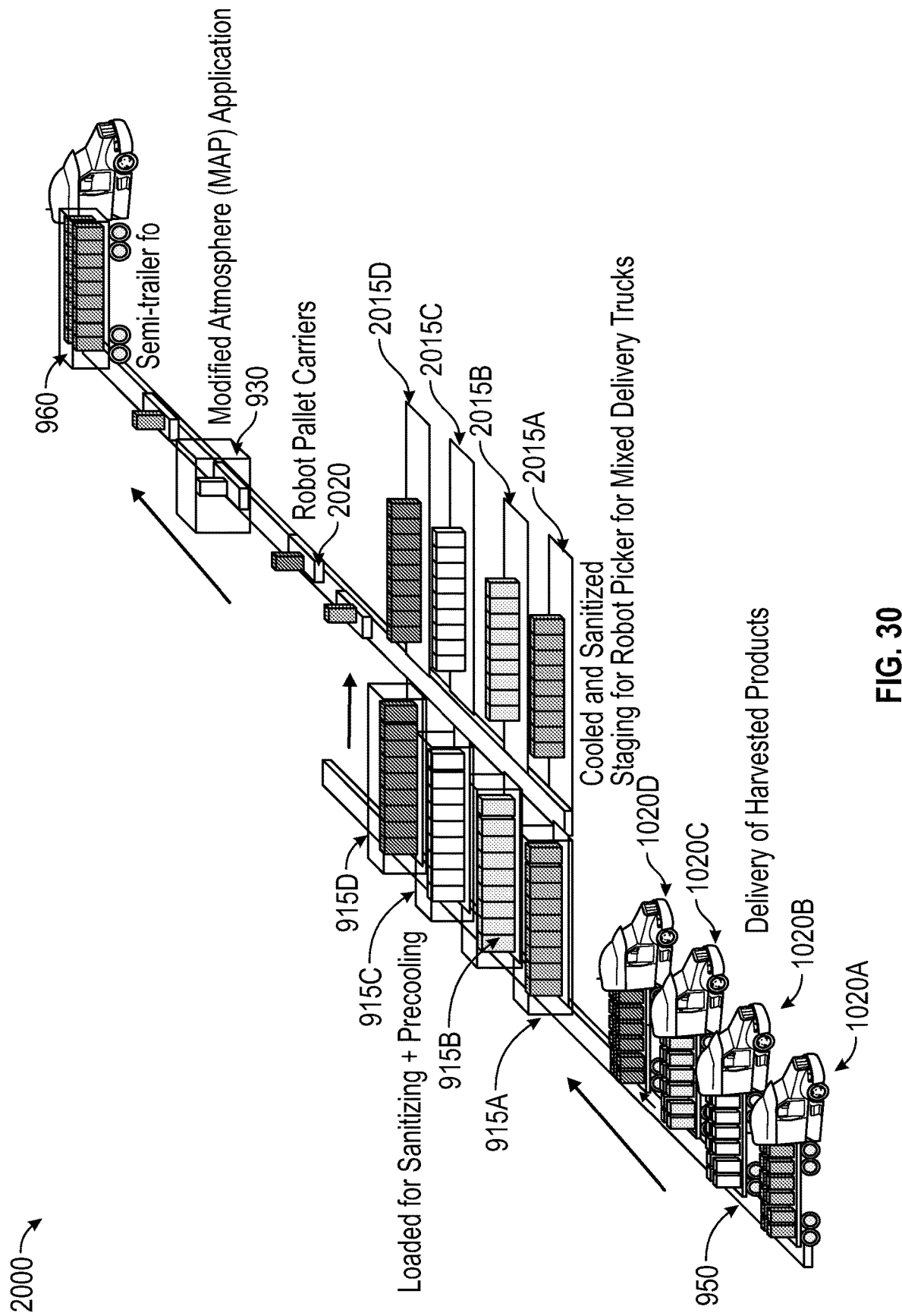
FIG. 30 is a diagram illustrating an embodiment of the invention in which a plurality of combined sanitization and precooling containers and a modified atmosphere pallet (MAP) application system are integrated into an overall system and process, using cross-docking sanitization and precooling, along with staging and robot carriers, for palletized product harvested from a field.

FIG. 30 illustrates an embodiment of an overall system (2000) of the invention that includes an integrated sanitization, precooling and MAP process with a cross dock arrangement. In this embodiment, the system (2000) includes a plurality of combination sanitization and precooling containers or units (915A, 915B, 915C, and 915D) just loaded and an automated, modified atmosphere pallet (MAP) application system (930). The system (2000) further includes a plurality of staging areas (2015A, 2015B, 2015C, and 2015D) in which completed cooled and sanitized products are held after the cooling and sanitization treatment. Additionally, this system (2000) includes one or more robot pallet carriers (2020) for delivering the completed cooled and sanitized products from the staging areas (2015A, 2015B, 2015C, and 2015D) to the automated, modified atmosphere pallet (MAP) application system (930). In this embodiment, pallets of harvested, perishable product are first transported to the system (2000) via a plurality of trucks or semi-trailers (1020A, 1020B, 1020C, and 1020D) from the field after harvesting of the product(s). The pallets of product are thereafter moved or transported to the combination sanitization and precooling containers (915A, 915B, 915C, and 915D) for treatment with a sanitizer to reduce spoilage or pathogenic organisms that may be present on the surface of the product, while also cooling the product to a desirable temperature (e.g., 32-34° F.). After treatment and cooling is completed, the cooled and sanitized perishable product is positioned in the one or more staging areas (2015A, 2015B, 2015C, and 2015D), and thereafter, the cooled and sanitized perishable product is moved, via the one or more robot pallet carriers (2020), to the automated, modified atmosphere pallet (MAP) application system (930) to add an MAP to the product. Although the MAP system (930) in this embodiment is automated, the MAP system (930) could also be semi-automatic. Once the pallets have completed the application in the MAP system (930), the pallets are finally moved or transported to a final shipping semi-trailer (960) for transportation to a storage warehouse or other location. According to this embodiment, pallets of perishable product are moved or transported between each of the containers or apparatus via one or more shuttle conveyors (950) and/or one or more robot pallet carriers (2020).

Figure 31:
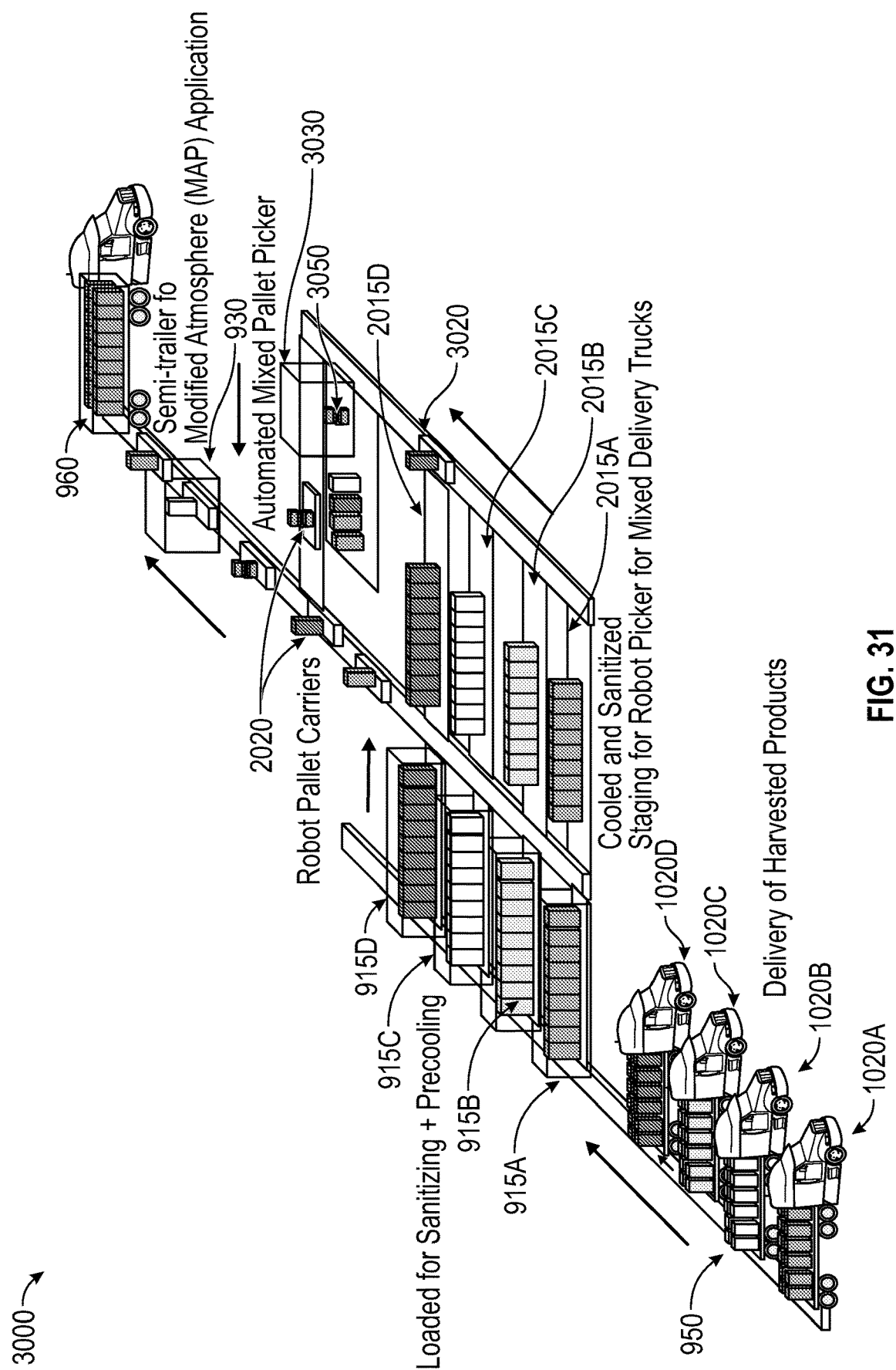
FIG. 31 is a diagram illustrating an embodiment of the invention in which a plurality of combined sanitization and precooling containers and a modified atmosphere pallet (MAP) application system are integrated into an overall system and process, using cross-docking sanitization and precooling, along with staging and robot carriers, for mixed load palletized product harvested from a field (or multiple production sources).

FIG. 31 illustrates another embodiment of an overall system (3000) of the invention that includes an integrated sanitization, precooling and MAP process with a cross dock arrangement. In this embodiment, the system (3000) includes a plurality of combination sanitization and precooling containers or units (915A, 915B, 915C, and 915D) just loaded and an automated, modified atmosphere pallet (MAP) application system (930). The system (3000) further includes a plurality of staging areas (2015A, 2015B, 2015C, and 2015D) in which completed cooled and sanitized products are held after the cooling and sanitization treatment. Additionally, this system (3000) includes one or more robot pallet carriers (2020) for delivering the completed cooled and sanitized products from the staging areas (2015A, 2015B, 2015C, and 2015D) to the automated, modified atmosphere pallet (MAP) application system (930). Moreover, this system (3000) includes an automated mixed pallet picker (3030) in which completed cooled and sanitized products are delivered, via, e.g., one or more robot pallet carriers (2020), from the staging areas (2015A, 2015B, 2015C, and 2015D), in order to provide a mixed pallet of perishable product (3050) to the automated, modified atmosphere pallet (MAP) application system (930) and thereafter, to a semi-trailer (960) for transportation to a storage warehouse or other location. In this embodiment, pallets of harvested, perishable product are first transported to the system (3000) via a plurality of trucks or semi-trailers (1020A, 1020B, 1020C, and 1020D) from the field after harvesting of the product(s). The pallets of product are thereafter moved or transported to the combination sanitization and precooling containers (915A, 915B, 915C, and 915D) for treatment with a sanitizer to reduce spoilage or pathogenic organisms that may be present on the surface of the product, while also cooling the product to a desirable temperature (e.g., 32-34° F.). After treatment and cooling is completed, the cooled and sanitized perishable product is positioned in the one or more staging areas (2015A, 2015B, 2015C, and 2015D). Thereafter, the cooled and sanitized perishable product is moved, via the one or more robot pallet carriers (2020), to (i) the automated, modified atmosphere pallet (MAP) application system (930) to add an MAP to the product or (ii) the automated mixed pallet picker (3030) and then to the automated, modified atmosphere pallet (MAP) application system (930) to add an MAP to the mixed pallet of perishable product (3050). Although the MAP system (930) and the mixed pallet picker (3030) in this embodiment are automated, either or both of the MAP system (930) and the mixed pallet picker (3030) could also be semi-automatic. Once the pallets have completed the application in the MAP system (930), the pallets are finally moved or transported to a final shipping semi-trailer (960) for transportation to a storage warehouse or other location. According to this embodiment, pallets of perishable product are moved or transported between each of the containers or apparatus via one or more shuttle conveyors (950) and/or one or more robot pallet carriers (2020).

Figure 32:
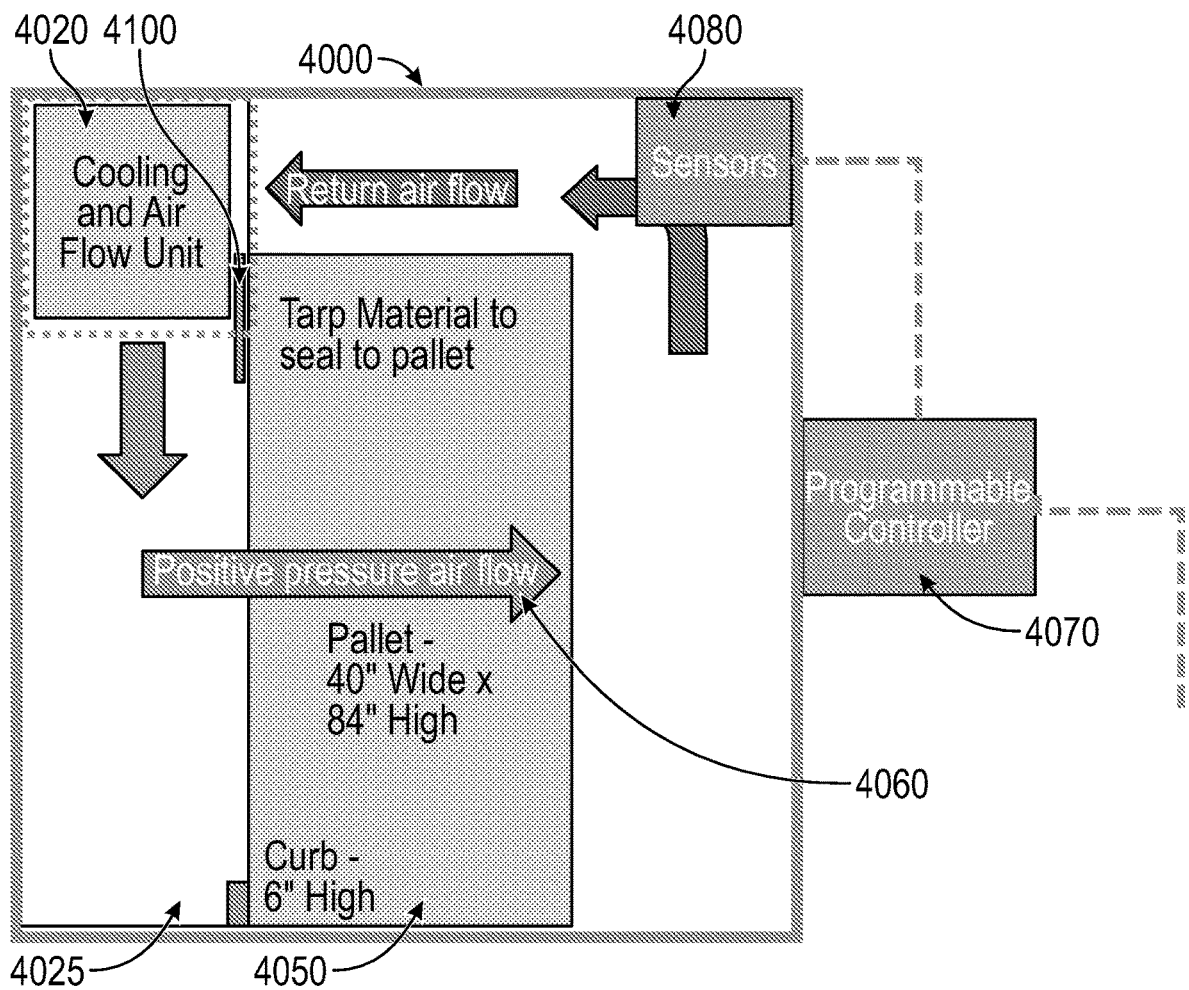
FIG. 32 is a diagram illustrating an embodiment of a precooling system of the invention using a container (or a semi-trailer) in which at least one sensor and a programmable controller are included with the system.

FIG. 32 illustrates another embodiment of a precooling container (4000) of the invention in which a refrigeration/cooling and pressure air flow unit (4020) is included within a portion (4025) of the container (4000). The refrigeration/cooling and pressure air flow unit (4020) includes, for example, fans and/or cooling coils to provide the necessary cooling capacity to the container (4000). Air (i.e., positive pressure air flow (4060)) is forced through a pallet(s) (4050) of cartons of product (see horizontal and/or vertical arrows in FIG. 32). The air returns up and over the pallets (4050) back to the refrigeration/cooling and pressure air flow unit (4020). A tarp material (4100) is also provided between the refrigeration/cooling and pressure air flow unit (4020) and the pallet(s) (4050) in order to seal the pallet(s) (4050) and effectively force the positive pressure air flow (4060) through the pallet(s) (4050). Additionally, according to this embodiment, a programmable controller (4070) and one or more sensors (4080) are included with the container (4000). The one or more sensors (4080) measure various parameters within the container (4000) including, e.g., a concentration of sanitizing substances in the air to achieve a prescribed treatment, a presence of at least one airborne microorganism to determine when to conclude a sanitizing treatment cycle, a pulp temperature of the perishable product to determine when to conclude a precooling cycle, the environment to determine when to conclude a venting and scrubbing of container gasses to enable removal of the product, and/or liquid condensate to determine treatment for wastewater removal. The one or more sensors (4080) is configured to supply the collected data relating to the various parameters to the programmable controller (4070) in which a control program having a prescribed recipe is saved, which allows for the controller (4070) to adjust one or more parameters of the process by sending a control signal to one or more of the refrigeration/cooling and pressure air flow unit (4020), a humidity system (not shown), an ozone feed system (not shown), a venting system (not shown), and/or a substance spraying system (see, e.g., treatment sprayer 5040 of FIGS. 33A and 33B), to achieve a target cooling rate, relative humidity, atmosphere level, substance treatment level, and/or microorganism count reduction.

Figures 33A, 33B:
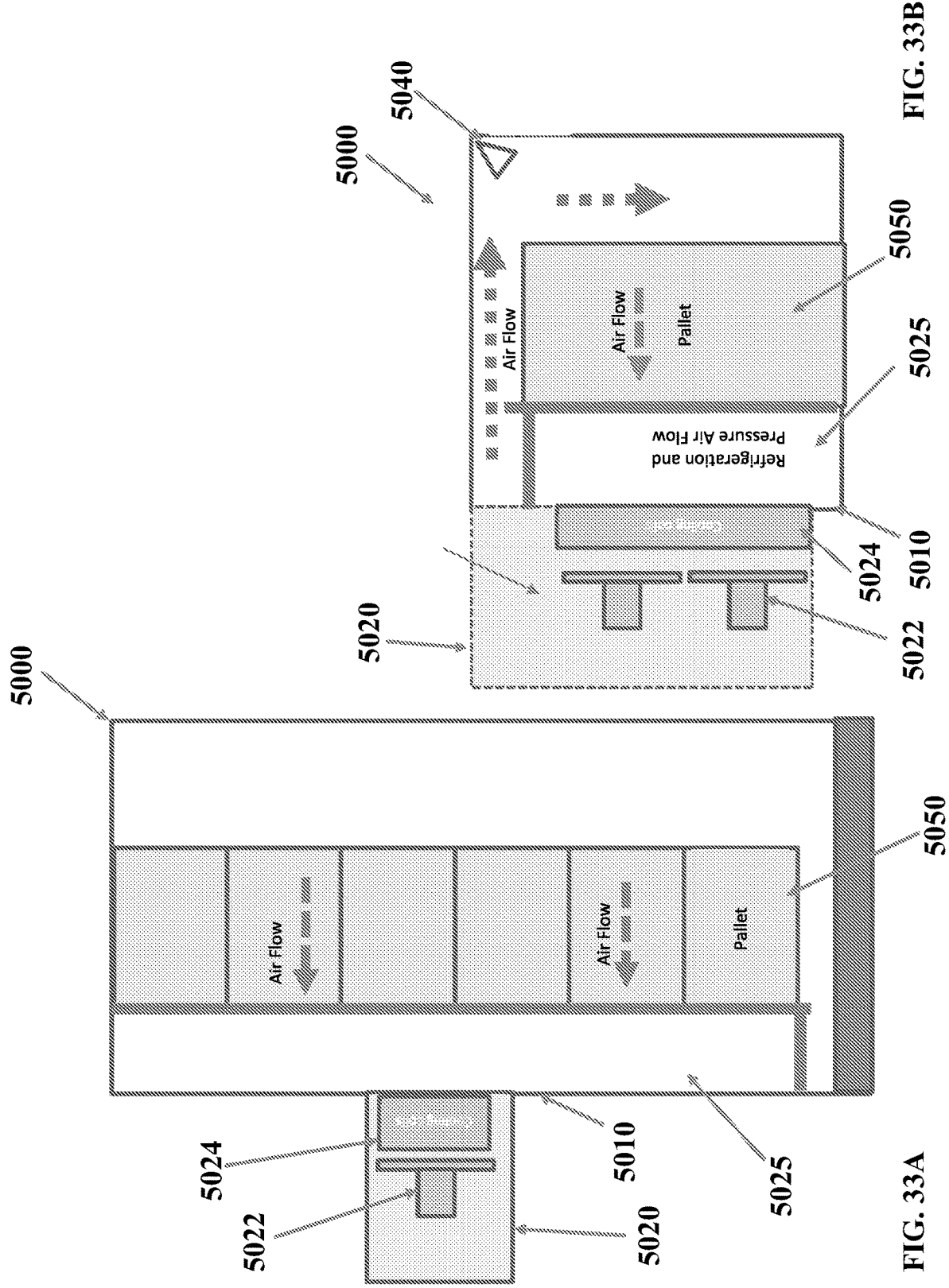
FIG. 33A is a diagram illustrating a top view of an embodiment of a combined precooling and treatment unit or container of the invention that allows for clipping on the refrigeration equipment onto the side(s) of the unit or container.
FIG. 33B is a diagram illustrating a side or end view of the container of FIG. 33A.

FIGS. 33A and 33B illustrate an embodiment of a combined precooling and treatment unit or container of the invention in which a 40' container (5000) (or, alternatively, a 53' semi-trailer) is modified by attaching or clipping at least one cooling system (5020) onto at least one side (5010) of the container (5000). The at least one cooling system (5020) is attached to the at least one side (5010) of the container (5000), with the at least one side (5010) being modified to enable (i) a prescribed refrigeration and pressure air flow (5025) and (ii) air recirculation (horizontal and/or vertical arrows) across pallets (5050) of perishable product, as depicted in FIGS. 33A and 33B. The at least one cooling system (5020) includes fans (5022) and cooling coils (5024) to provide the necessary cooling capacity to the container (5000). Additionally, according to this embodiment, a treatment sprayer (5040) can be included to provide a gaseous or vaporized sanitizer to the container (5000) and/or air flow plenum to be recirculated through the pallets (5050) of perishable product. Moreover, according to this embodiment, a single row of pallets (5050) of perishable product is provided within the container (5000).

Figure 34A:
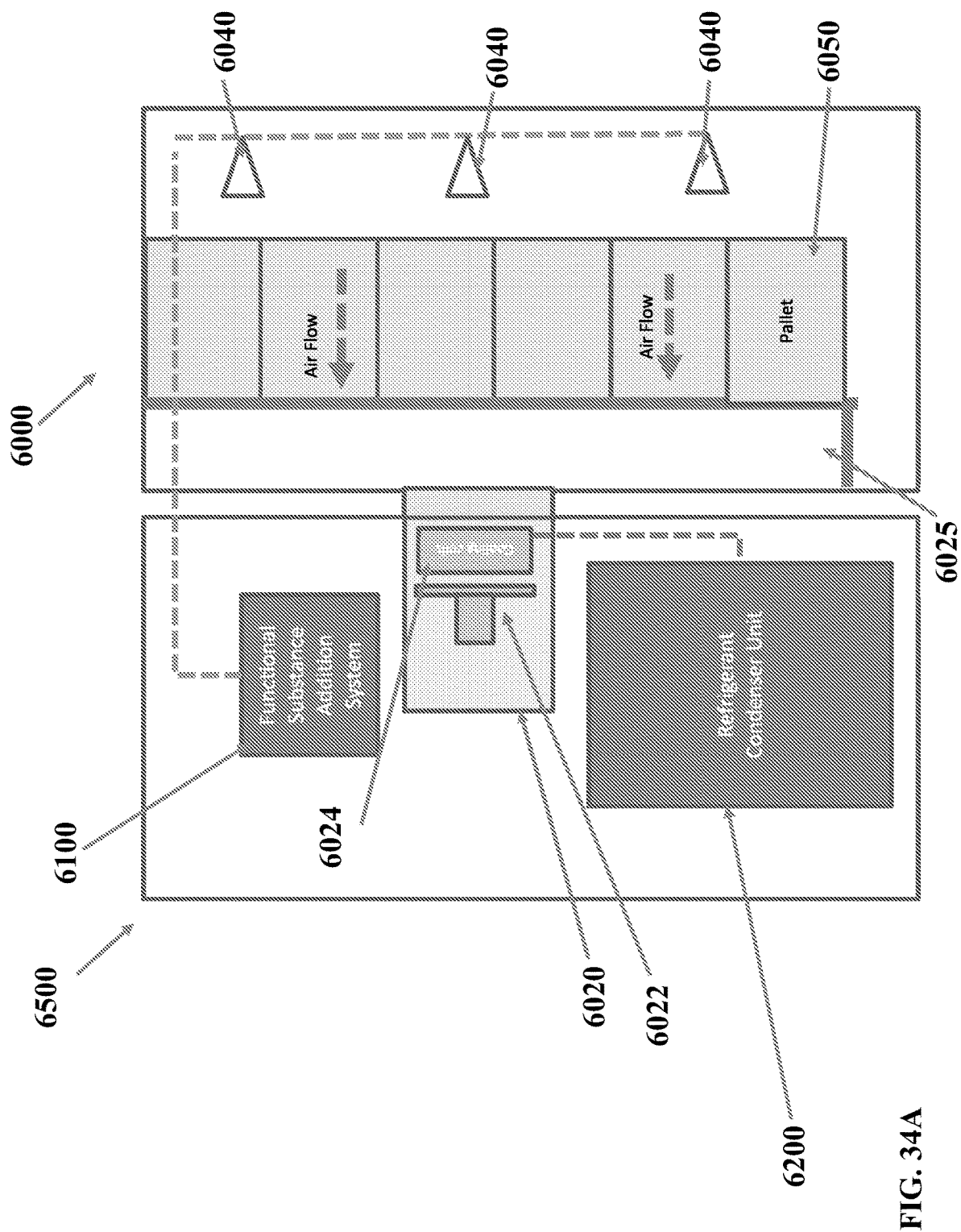
FIG. 34A is a diagram illustrating a top view of another embodiment of a combined precooling and treatment unit or container of the invention that allows for attaching the refrigeration equipment onto the side(s) of the unit or container with the inclusion of a trailer to hold the refrigeration equipment.
Figure 34B:
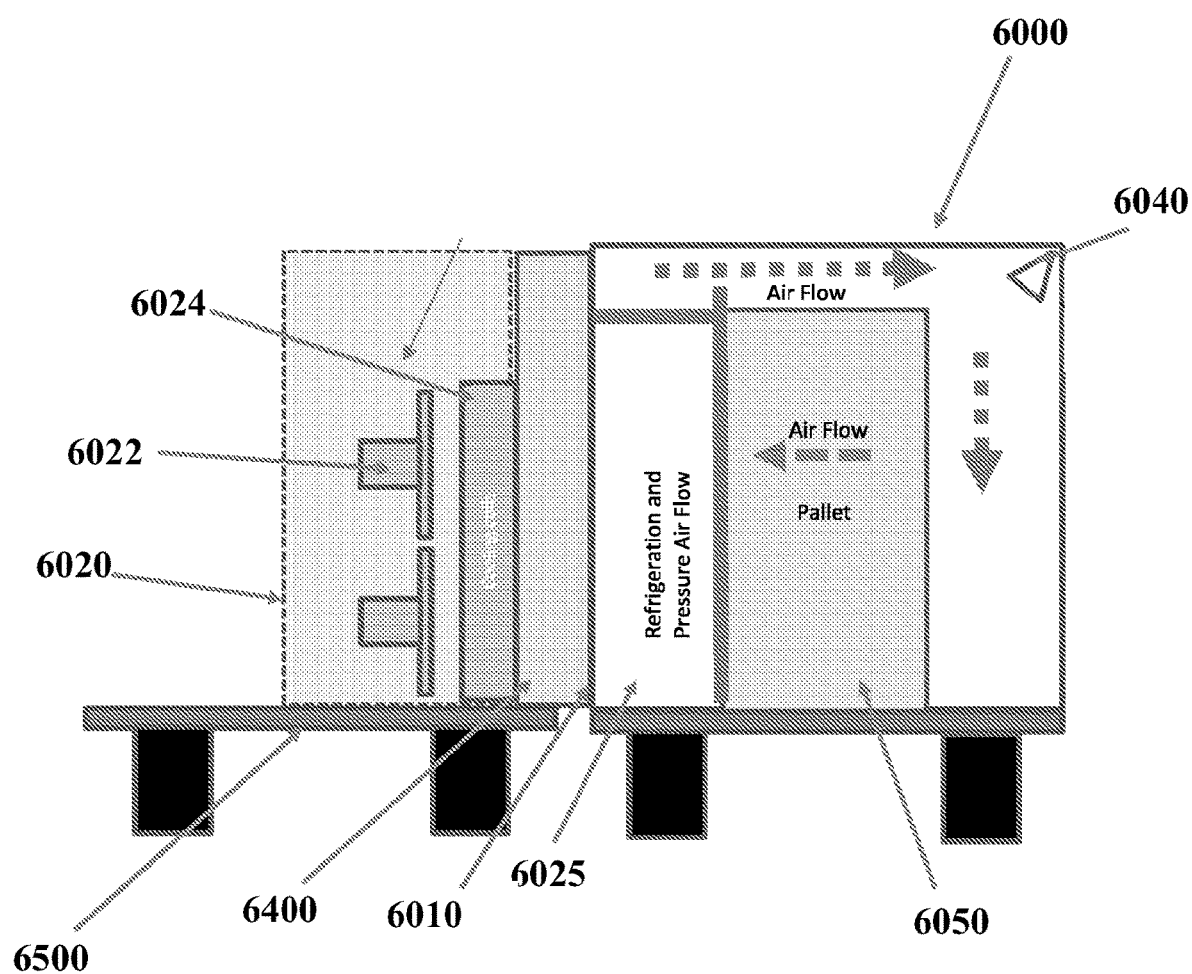
FIG. 34B is a diagram illustrating a side or end view of the container of FIG. 34A.

FIGS. 34A and 34B illustrate an embodiment of a combined precooling and treatment unit or container of the invention in which a 40' container (6000) (or, alternatively, a 53' semi-trailer) is modified by attaching or clipping at least one cooling system or "reefer" (6020) onto at least one side (6010) of the container (6000). The at least one cooling system or "reefer" (6020) is held by a flatbed trailer (6500) and attached to the at least one side (6010) of the container (6000), with the at least one side (6010) being modified to enable (i) a prescribed refrigeration and pressure air flow (6025) and (ii) air recirculation (horizontal and/or vertical arrows) across pallets (6050) of perishable product, as depicted in FIGS. 34A and 34B. The at least one cooling system or "reefer" (6020), which is held by the flatbed trailer (6500), is generally attached to the at least one side (6010) of the container (6000) via a pop-out side and/or attachment member (6400). The at least one cooling system or "reefer" (6020) includes fans (6022) and cooling coils (6024) to provide the necessary cooling capacity to the container (6000). The flatbed trailer (6500) can further hold (i) a refrigerant condenser unit (6200) to provide necessary cooling capacity to the at least one cooling system or "reefer" (6020) and (ii) a functional substance addition system (6100) to provide gaseous or vaporized sanitizer substances to the container (6000). In particular, according to this embodiment, a plurality of treatment sprayers (6040) are included to provide a gaseous or vaporized sanitizer from the functional substance addition system (6100) to the container (6000) and/or air flow plenum to be recirculated through the pallets (6050) of perishable product. Moreover, according to this embodiment, a single row of pallets (6050) of perishable product is provided within the container (6000).

Figure 35A:
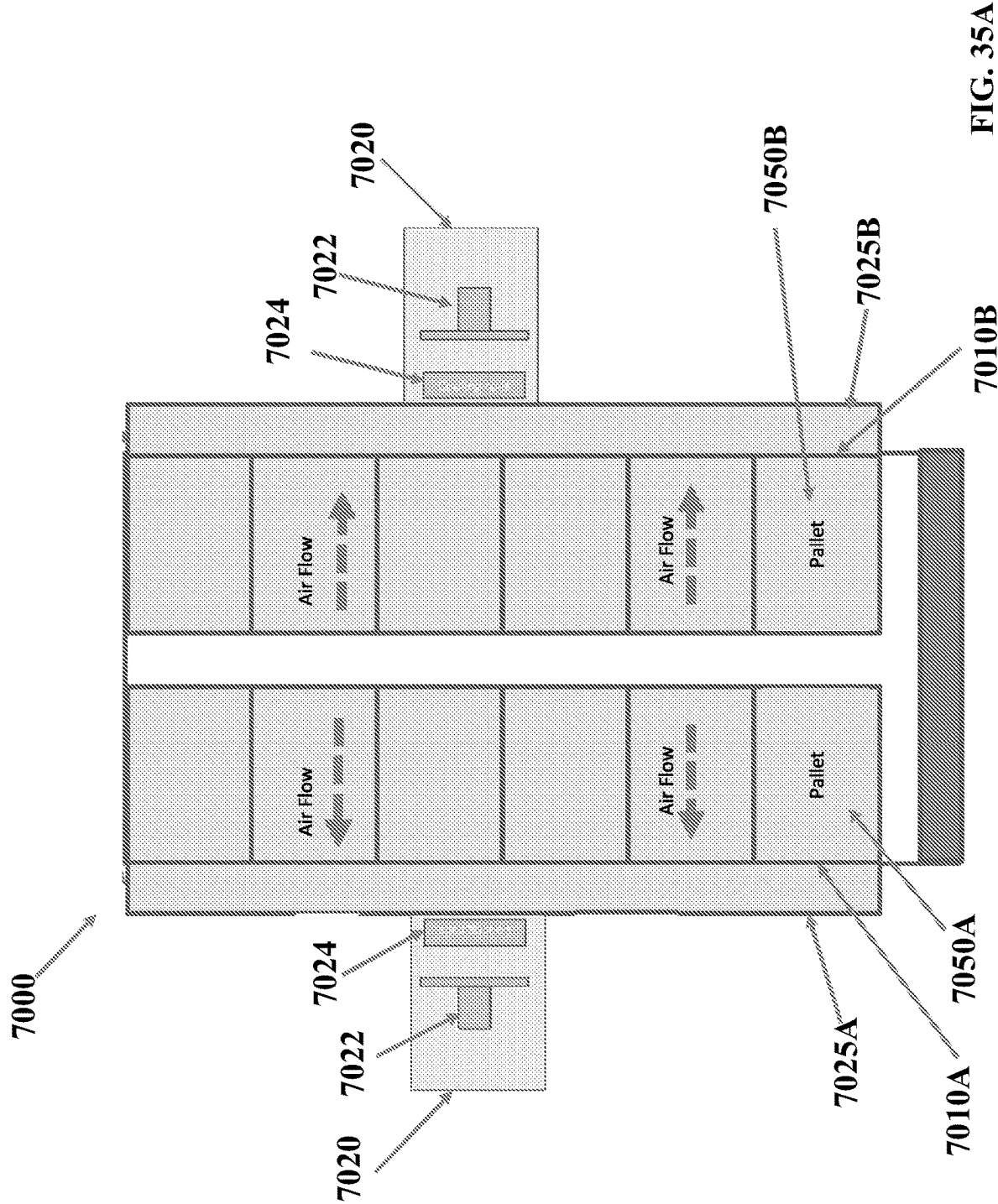
FIG. 35A is a diagram illustrating a top view of another embodiment of a combined precooling and treatment unit or container of the invention that allows for clipping on the refrigeration equipment onto both sides of the unit or container.
Figure 35B:
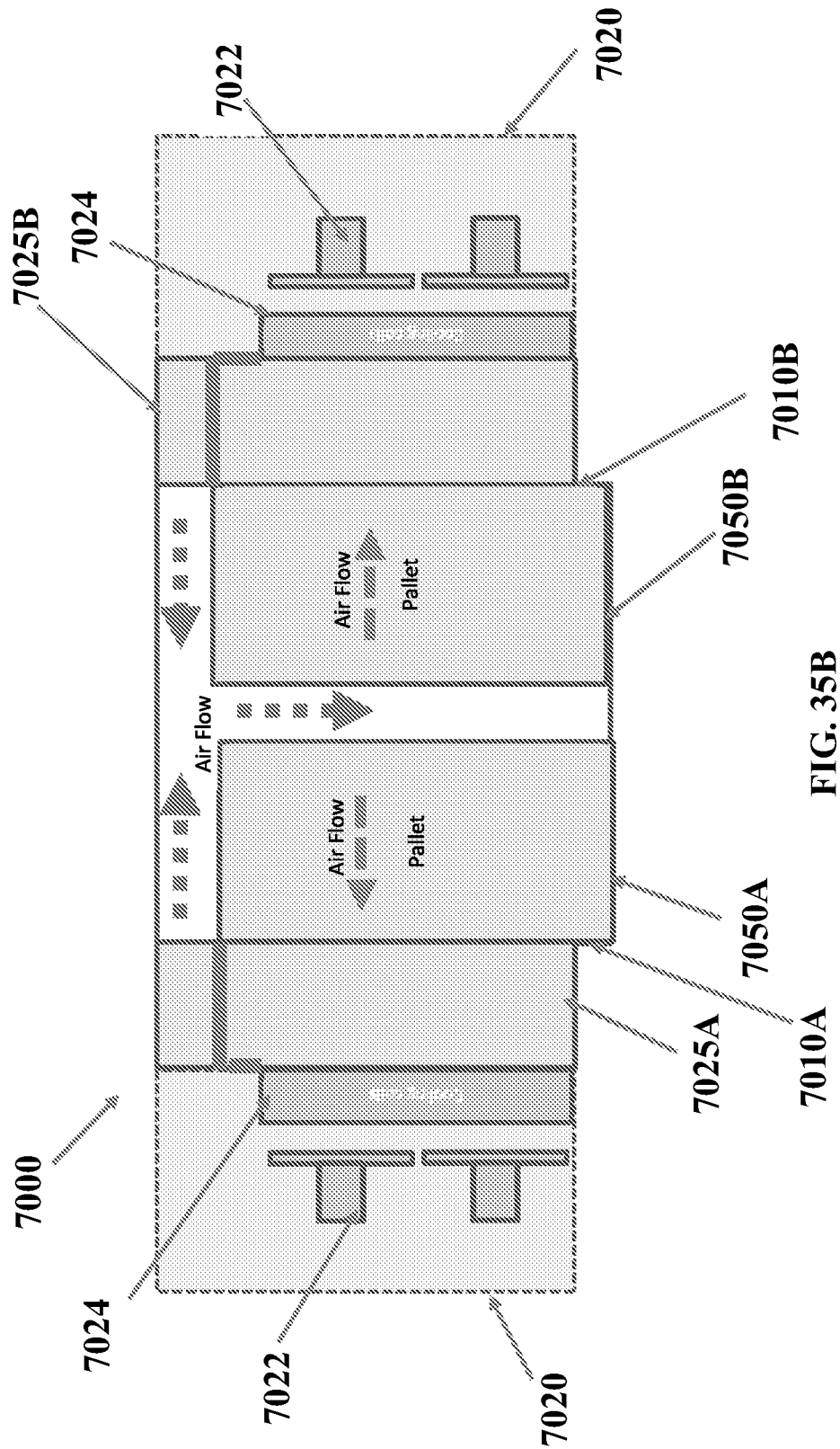
FIG. 35B is a diagram illustrating a side or end view of the container of FIG. 35A.

FIGS. 35A and 35B illustrate an embodiment of a combined precooling and treatment unit or container of the invention in which a 40' container (7000) (or, alternatively, a 53' semi-trailer) is modified by attaching or clipping a cooling system (7020) onto each side (7010A and 7010B) of the container (7000). Each cooling system (7020) is attached to the respective side (7010A and 7010B) of the container (7000) via a "pop out" side (7025A and 7025B) (see also, e.g., embodiment described above with respect to FIGS. 9, 10A, and 10B), with each side (7010A and 7010B) of the container (7000) being modified to enable (i) a prescribed refrigeration and pressure air flow and (ii) air recirculation (horizontal and/or vertical arrows) across two rows of pallets (7050A and 7050B) of perishable product, as depicted in FIGS. 35A and 35B. Each cooling system (7020) includes fans (7022) and cooling coils (7024) to provide the necessary cooling capacity to the container (7000). Moreover, according to this embodiment, as described above, two rows of pallets (7050A and 7050B) of perishable product are provided within the container (7000).

FIGS. 36A and 36B illustrate another embodiment of a combined precooling and treatment unit or container of the invention in which a 40' container (8000) (or, alternatively, a 53' semi-trailer) is modified by attaching or clipping at least one cooling system (8020) onto at least one side (8010) of the container (8000). The at least one cooling system (8020) is attached to the at least one side (8010) of the container (8000), with the at least one side (8010) being modified to enable (i) a prescribed refrigeration and pressure air flow and (ii) air recirculation across pallets of perishable product (not shown). The at least one cooling system (8020) includes fans (8022) and cooling coils (8024) to provide the necessary cooling capacity to the container (8000). Additionally, according to this embodiment, a track system (8100) is included on which the at least one cooling system (8020) is positioned. This track system (8100) allows for the at least one cooling system (8020) to be slid into and out of the container (8000). As shown in the embodiment of FIGS. 36A and 36B, the at least one cooling system (8020) is provided along the side (8010) of the container (8000) or the at least one cooling system (8020') is positioned within the container (8000), with the track system (8100) allowing for this movement of the at least one cooling system (8020/8020').

Figure 37A:
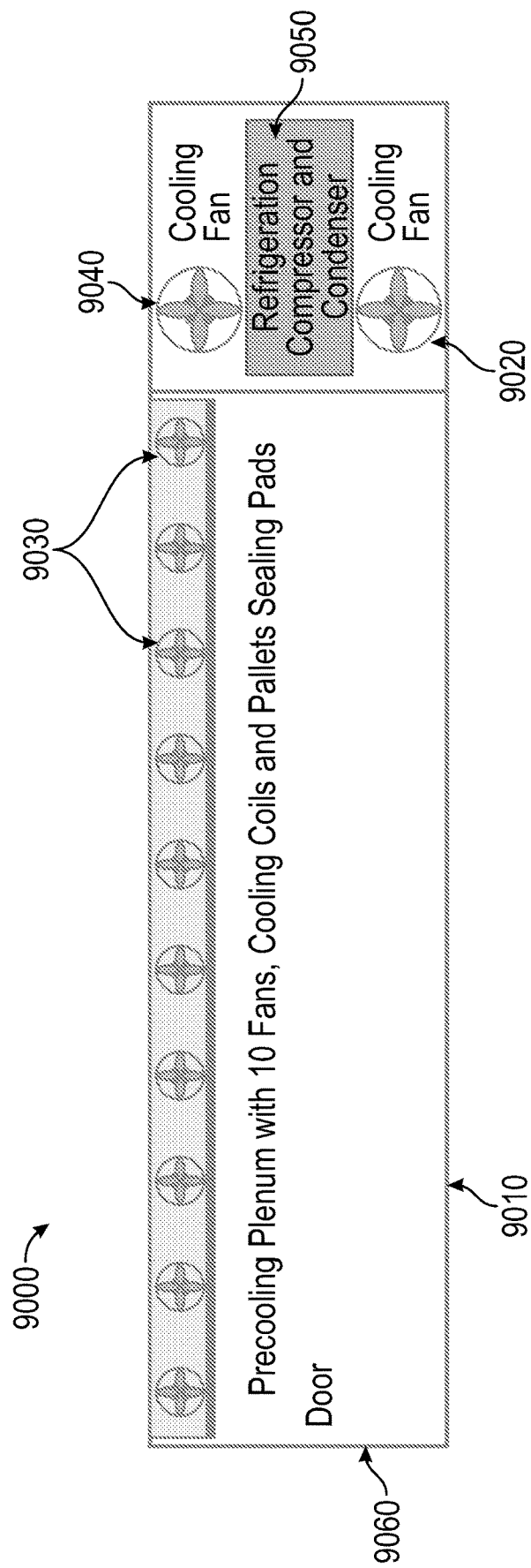
FIG. 37A is a diagram illustrating a top view of an alternative embodiment of a precooling system of the invention that allows for a cooling plenum and refrigeration components to be built into a single unit.
Figure 37B:
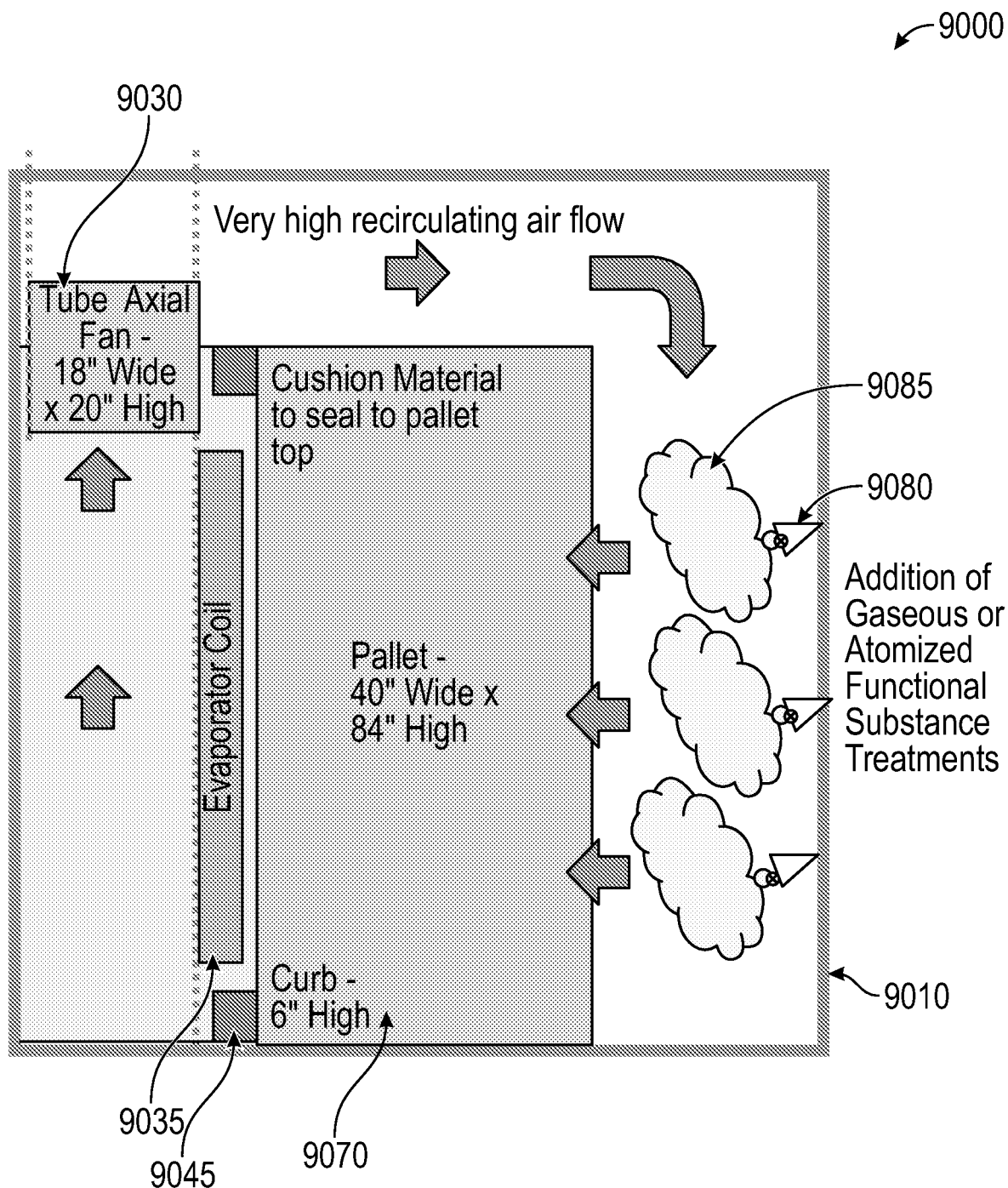
FIG. 37B is a diagram illustrating a side or end view of the precooling system of FIG. 37A.

FIGS. 37A and 37B illustrate an alternative embodiment of a precooling system of the invention in which a pre-cooling plenum (9010) is combined with a refrigeration zone (9020) in a single mobile unit (9000), such as, e.g., a 53-foot mobile trailer. The pre-cooling plenum (9010), in which a plurality of pallets of perishable product can be placed into the unit (9000) via a door (9060) (see, e.g., pallet 9070 of FIG. 37B), includes a plurality of cooling fans (9030) and/or cooling coils (9035) and/or pallet sealing pads (9045), such as, e.g., a cushion material to seal the top of a pallet (see, e.g., pallet 9070 of FIG. 37B). According to one embodiment, the pre-cooling plenum (9010) includes at least ten cooling fans (9030) for forced air recirculation and an evaporation coil (9035). The refrigeration zone (9020) includes one or more cooling fans (9040) and a refrigeration unit (9050) having a refrigeration compressor and condenser. The one or more cooling fans (9040) keep the air cool in the refrigeration zone (9020), which can be in a nose (or front end) of the single mobile unit (9000) (e.g., trailer), according to one embodiment. The refrigeration zone (9020), which includes the cooling fans (9040) and the refrigeration unit (9050), is configured to provide the necessary cooling capacity to the pre-cooling plenum (9010) of the single mobile unit (9000). It does this by cooling the refrigerant used in the evaporator coil (9035). For example, the cooling fans (9030) cause cool air to be recirculated through the one or more pallets (9070) of product and across the evaporator coil (9035) (see, e.g., horizontal and/or vertical arrows in FIG. 37B). Additionally, according to this embodiment, one or more treatment sprayers (9080) can be included to provide a gaseous, vaporized, and/or atomized functional substance treatment (e.g., sanitizer) to the one or more pallets (9070) of product.

According to the embodiment of FIGS. 37A and 37B, in the case in which a 53-foot mobile trailer is used as the single mobile unit (9000), the unit (9000) can have inside dimensions of, e.g., over 8 feet wide and 8 feet high. In addition, according to one embodiment, a plurality of pallets (9070) can be placed within this single mobile unit (9000), with each pallet (9070) having dimensions of, for example, 40 inches in width by 84 inches in height.

Figure 38:
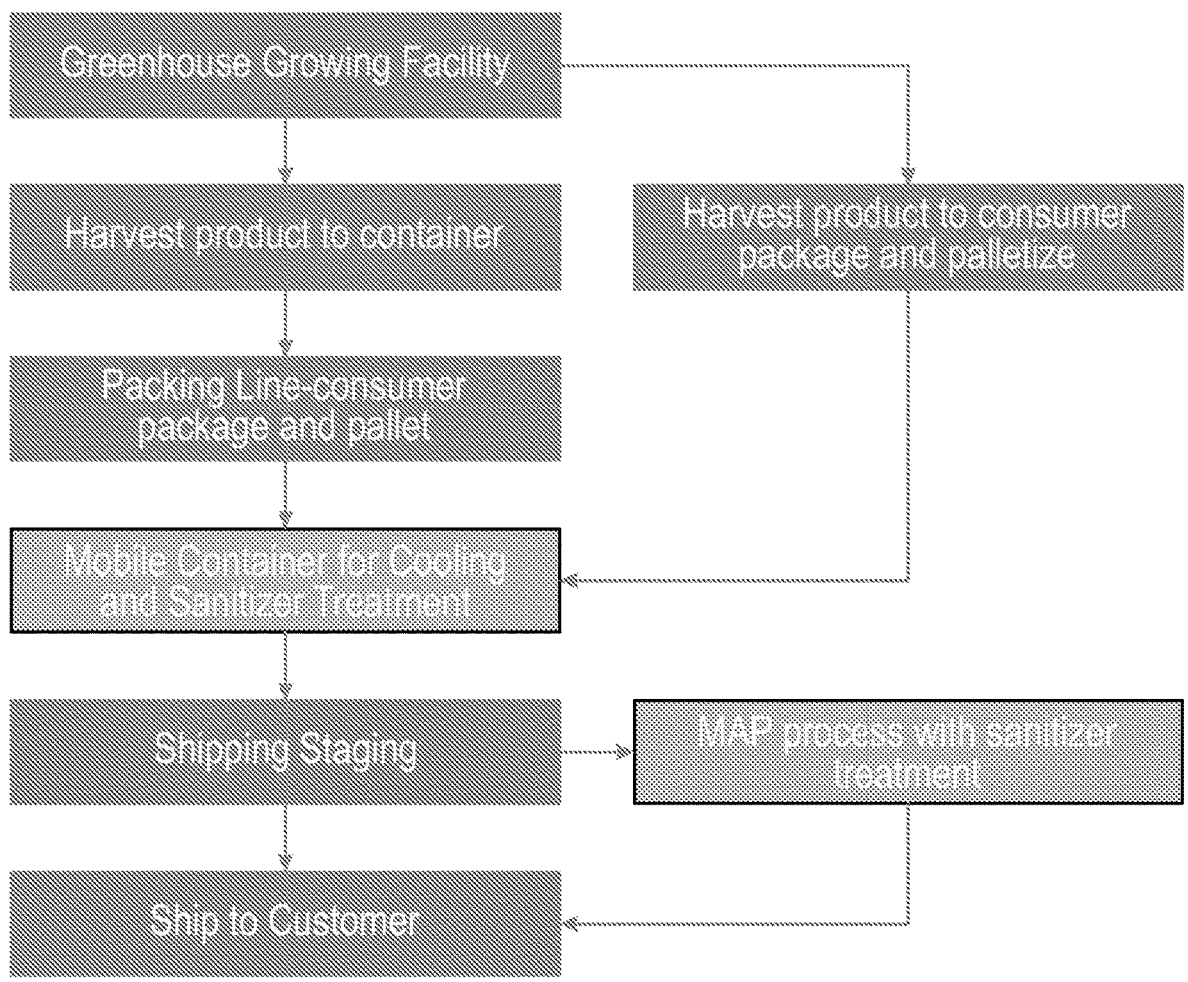
FIG. 38 is a flowchart of an embodiment of the inventive process using a mobile container with a greenhouse growing facility for cooling and sanitizing perishable product.

FIG. 38 is a flowchart of an embodiment of the inventive process using a mobile container designed to cool and to sanitize product that is grown in a greenhouse growing facility, while also being able to provide an optional MAP process (with a sanitizer treatment). In this process, a perishable product is grown and harvested within a greenhouse growing facility. According to one embodiment, the harvested product is then packed within a container and placed on a packing line to be packaged and palleted for a consumer. According to another embodiment, after harvesting the product from the greenhouse growing facility, the harvested product is directly packed into a consumer/retail package and palletized. The pallets of product are then cooled and sanitized/treated within a mobile container (as discussed in one or more of the embodiments above). After cooling and sanitizing the pallets of product, the pallets are staged for shipping. At this point, the cooled and sanitized pallets of product can optionally be treated with an MAP process with (or without) an additional sanitizer treatment. After the pallets are staged for shipping (or finish with the optional MAP process) via, e.g., a cross-docking configuration, which is further discussed below, the pallets are shipped to a customer(s).

Figure 39:
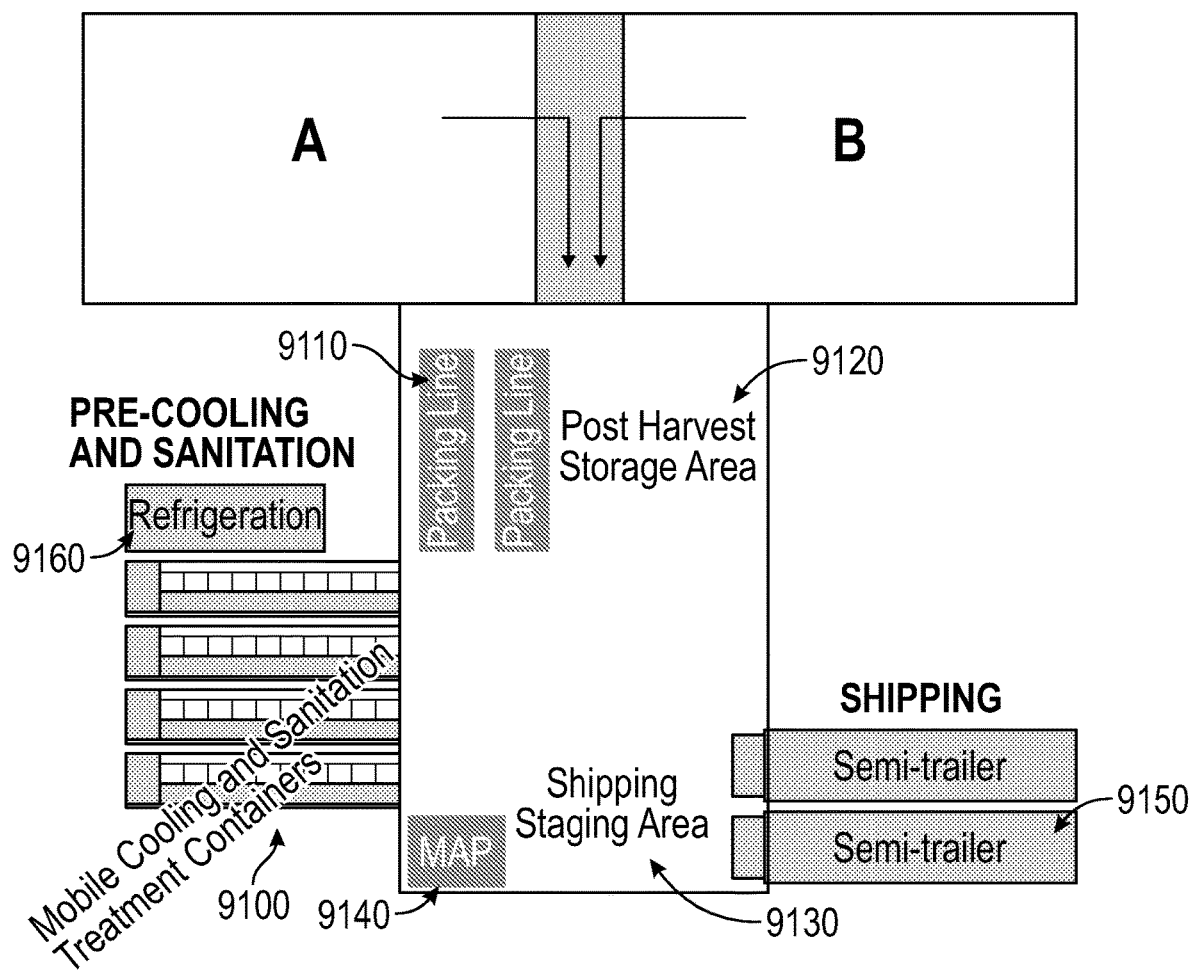
FIG. 39 is a diagram illustrating an embodiment of the invention in which a plurality of combined sanitization and precooling containers are integrated into an overall system and process, using cross-docking sanitization and precooling, for palletized product harvested from a greenhouse operation.

FIG. 39 illustrates an embodiment of the inventive process illustrated in FIG. 38 that uses one or more mobile containers designed to cool and to sanitize product that is grown in a greenhouse growing facility. As shown in FIG. 39, at least two greenhouse facilities (A and B) are used to grow and harvest one or more types of perishable product. The harvested product from each of the greenhouse facilities (A and B) is placed within containers (e.g., consumer packages/pallets and/or containers to be further packaged/palletized on packing lines (9110)) to be stored within a post harvest storage area (9120). The pallets of product are then placed within one or more modified, mobile containers (9100) to cool and to apply the sanitizing treatment before shipment. According to one embodiment, an additional refrigeration unit (9160) can be positioned next to the one or more modified, mobile containers (9100) for providing additional cooling capacity to the one or more modified, mobile containers (9100). The cooled and sanitized pallets of product are staged for shipping in a shipping staging area (9130). At this point, the cooled and sanitized pallets of product can optionally be treated with an MAP process (9140) with (or without) an additional sanitizer treatment. After the pallets are staged for shipping (or finish with the optional MAP process (9140)), the pallets are placed within semi-trailers (9150) to ship the pallets to one or more customers. The embodiment of FIG. 39 is considered a "cross-dock" arrangement because the greenhouse facilities (A and B) are integrated with a post harvest storage area (9120) having (i) one or more modified, mobile containers (9100) to cool and to apply the sanitizing treatment to pallets of product on one side of the post harvest storage area (9120), and (ii) shipping area having semi-trailers (9150) on an opposite side of the post harvest storage area (9120). Thus, the one or more modified, mobile containers (9100) to cool and to apply the sanitizing treatment to pallets of product are "cross-docked" from a shipping area having semi-trailers (9150).

Figure 40:
FIG. 40 is a flowchart of another embodiment of the inventive process using a mobile container with a greenhouse growing facility for cooling and sanitizing perishable product.

FIG. 40 is a flowchart of another embodiment of the inventive process using a mobile container designed to cool and to sanitize product that is grown in a greenhouse growing facility, while also being able to provide an optional MAP process (with a sanitizer treatment). In this process, a perishable product is grown and harvested within a greenhouse growing facility. According to this embodiment, after harvesting the product from the greenhouse growing facility, the harvested product is directly packed into a consumer/retail package and palletized using, e.g., a packing line. The pallets of product are then cooled and sanitized/treated within a mobile container (as discussed in one or more of the embodiments above). After cooling and sanitizing the pallets of product, the pallets are staged for shipping. At this point, the cooled and sanitized pallets of product can optionally be treated with an MAP process with (or without) an additional sanitizer treatment. After the pallets are staged for shipping (or finish with the optional MAP process) via, e.g., a cross-docking configuration, which is further discussed below, the pallets are shipped to a customer(s).

Figure 41:
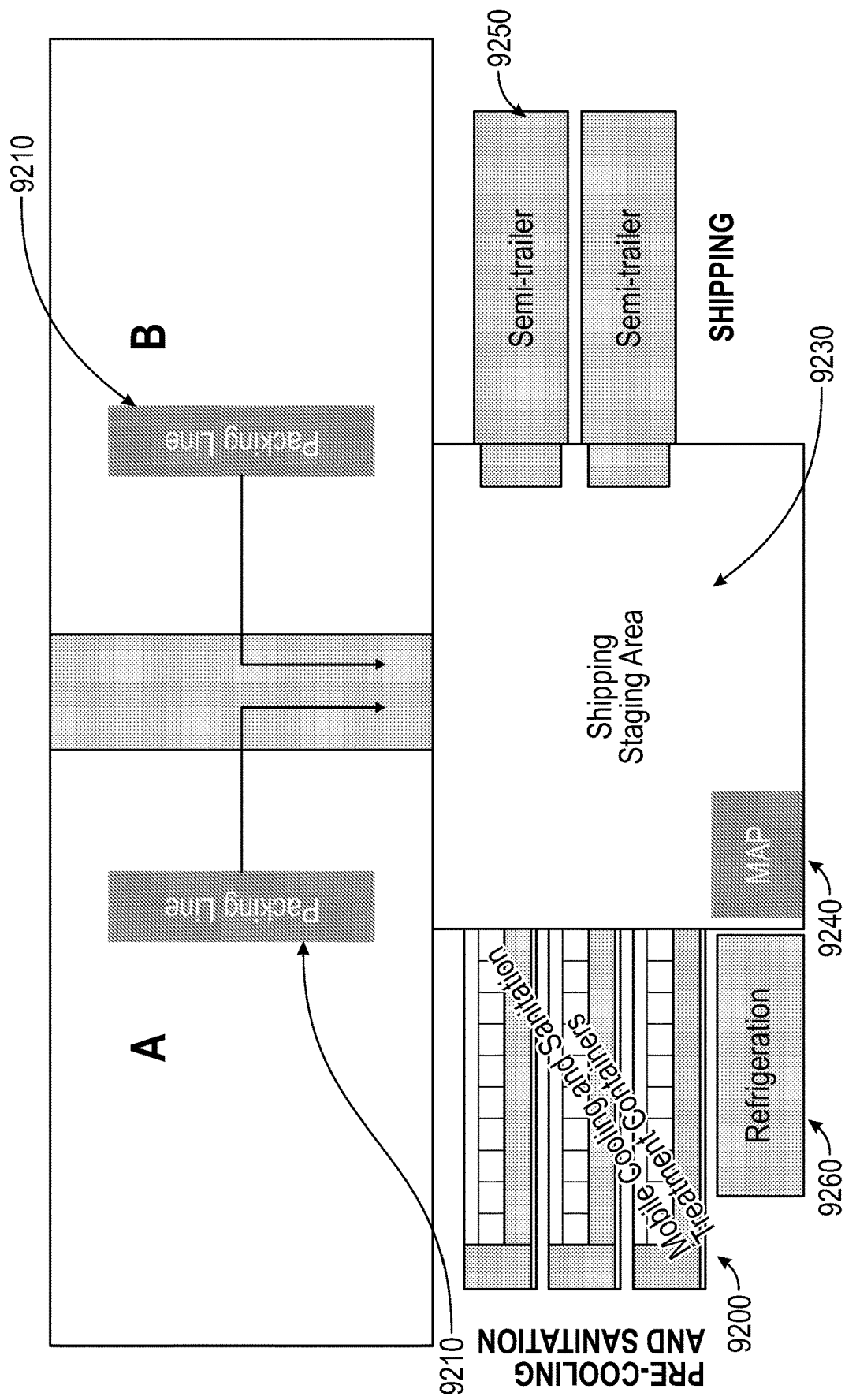
FIG. 41 is a diagram illustrating another embodiment of the invention in which a plurality of combined sanitization and precooling containers are integrated into an overall system and process, using cross-docking sanitization and precooling, for palletized product harvested from a greenhouse operation.

FIG. 41 illustrates an embodiment of the inventive process illustrated in FIG. 40 that uses one or more mobile containers designed to cool and to sanitize product that is grown in a greenhouse growing facility. As shown in FIG. 41, at least two greenhouse facilities (A and B) are used to grow and harvest one or more types of perishable product. The harvested product from each of the greenhouse facilities (A and B) is placed within consumer/retail packages and palletized via packing lines (9210) that are positioned within each of the greenhouse facilities (A and B). The pallets of product are then positioned within a shipping staging area (9230) where the pallets of product can then be placed within one or more modified, mobile containers (9200) to cool and to apply the sanitizing treatment before shipment. According to one embodiment, an additional refrigeration unit (9260) can be positioned next to the one or more modified, mobile containers (9200) for providing additional cooling capacity to the one or more modified, mobile containers (9200). The cooled and sanitized pallets of product are staged for shipping in the shipping staging area (9230). At this point, the cooled and sanitized pallets of product can optionally be treated with an MAP process (9240) with (or without) an additional sanitizer treatment. After the pallets are staged for shipping (or finish with the optional MAP process (9240)), the pallets are placed within semi-trailers (9250) to ship the pallets to one or more customers. The embodiment of FIG. 41 is also considered a "cross-dock" arrangement because the greenhouse facilities (A and B) are integrated with a shipping staging area (9230) having (i) one or more modified, mobile containers (9200) to cool and to apply the sanitizing treatment to pallets of product on one side of the shipping staging area (9230), and (ii) semi-trailers (9250) on an opposite side of the shipping staging area (9230). Thus, the one or more modified, mobile containers (9200) to cool and to apply the sanitizing treatment to pallets of product are "cross-docked" from a shipping area having semi-trailers (9150).

Figure 42:
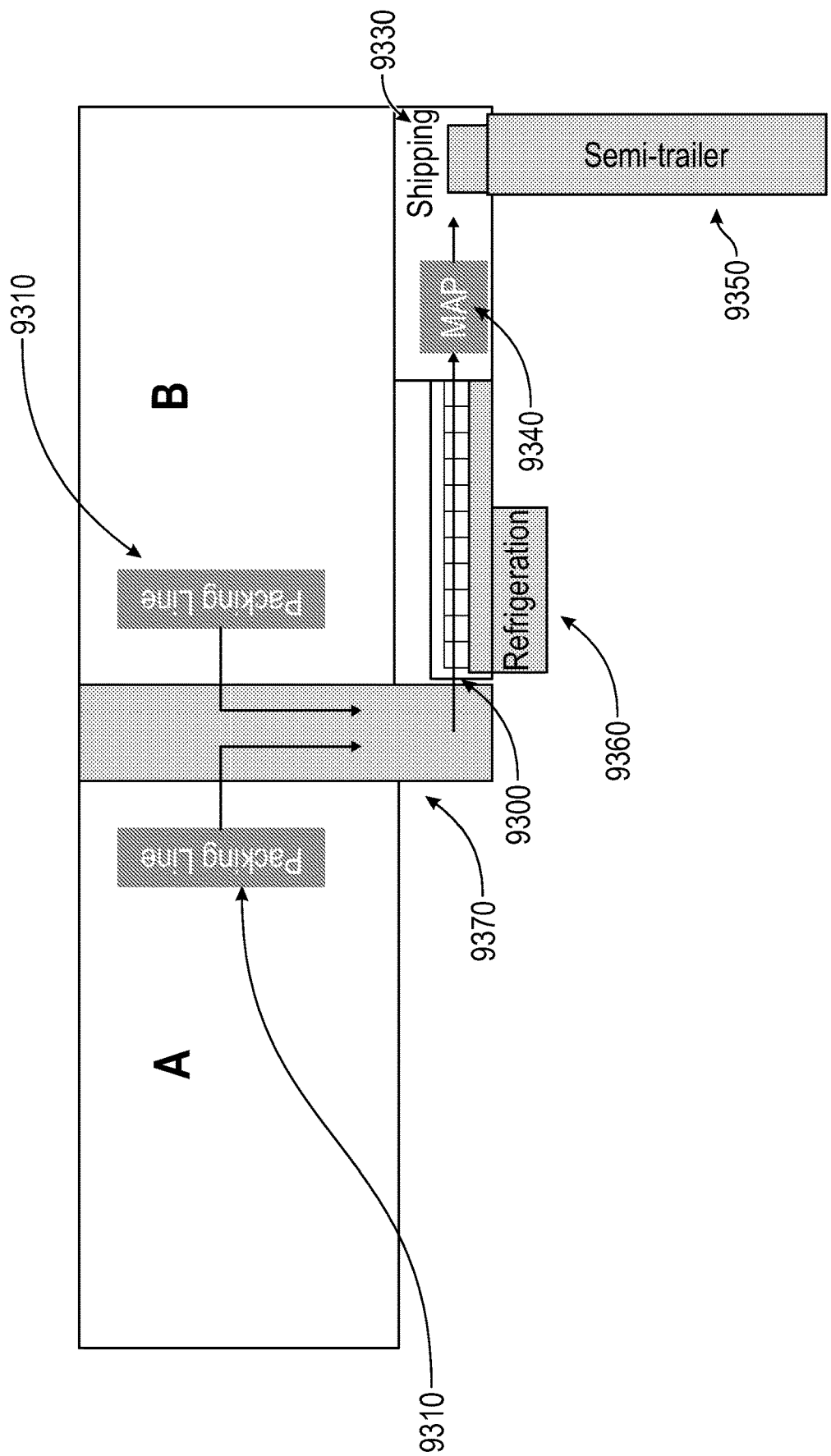
FIG. 42 is a diagram illustrating an embodiment of the invention in which a combined sanitization and precooling container comprises a pass-thru system for palletized product harvested from a greenhouse operation.

According to another embodiment, one or more mobile containers can be designed as a pass-thru unit or container to cool and to sanitize product that is grown in a greenhouse growing facility. For example, as shown in the embodiment of FIG. 42, at least two greenhouse facilities (A and B) are used to grow and harvest one or more types of perishable product. The harvested product from each of the greenhouse facilities (A and B) is placed within consumer/retail packages and palletized via packing lines (9310) that are positioned within each of the greenhouse facilities (A and B). The pallets of product are placed within one or more modified, mobile containers (9300) to cool and to apply the sanitizing treatment before shipment. The one or more modified, mobile containers (9300) of FIG. 42 are designed as "pass-thru" units or containers, as the pallets of product pass directly into the one or more modified, mobile containers (9300) from the greenhouse facilities (A and B) via, e.g., a conveyor or pallet shuttle (9370). According to one embodiment, an additional refrigeration unit (9360) can be positioned next to the one or more modified, mobile containers (9300) for providing additional cooling capacity to the one or more modified, mobile containers (9300). At this point, the cooled and sanitized pallets of product can optionally be treated with an MAP process (9340) with (or without) an additional sanitizer treatment. Thereafter, the pallets of product are staged for shipping within a shipping area (9330) and then the pallets are placed within semi-trailers (9350) to ship the pallets to one or more customers. In the embodiment of FIG. 42, the one or more modified, mobile containers (9300) that are positioned as a "pass-thru" unit or container for cooling and applying the sanitizing treatment to pallets of product are "cross-docked" from the shipping area (9330) having the semi-trailers (9350).

Figure 43:
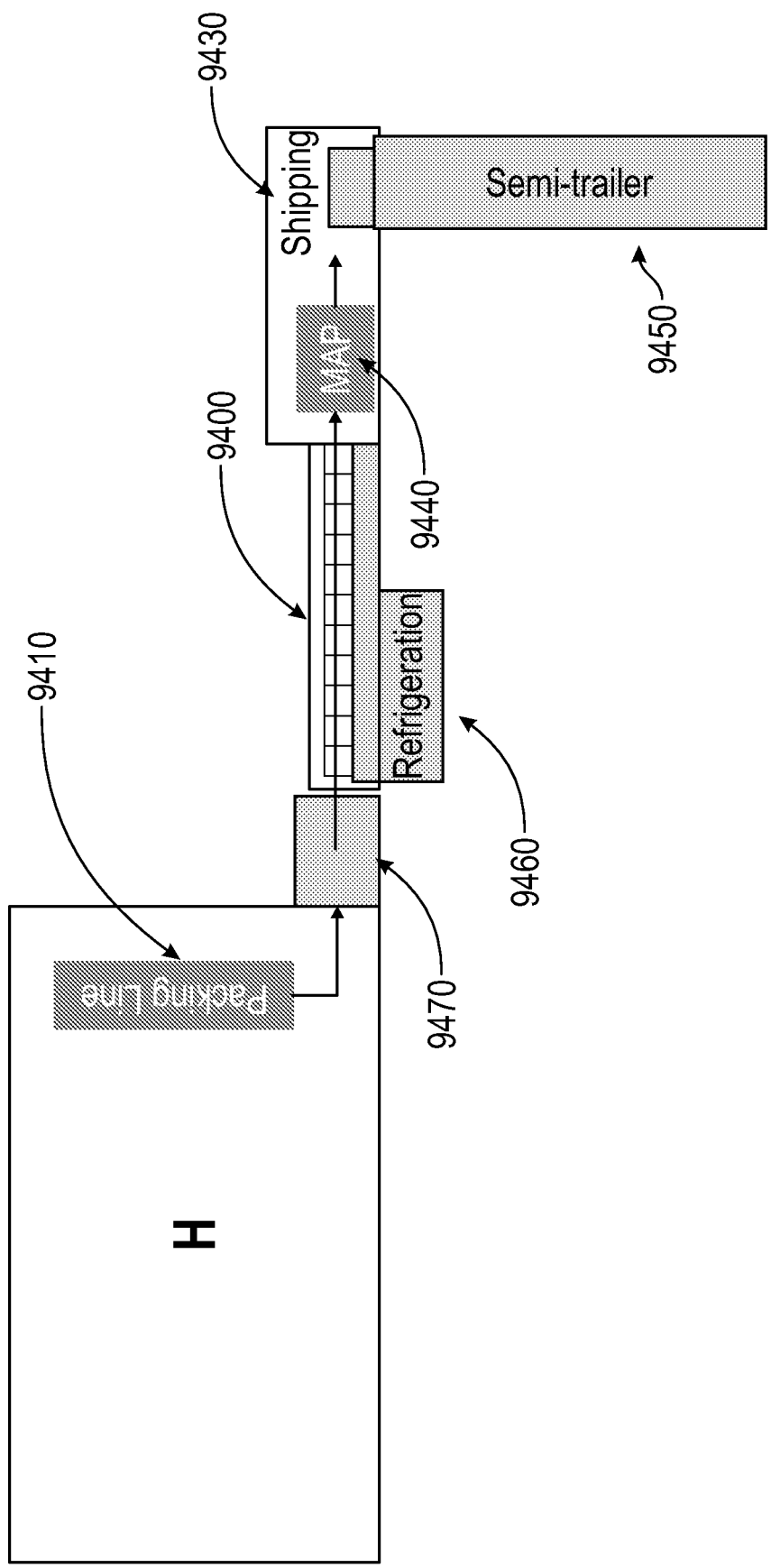
FIG. 43 is a diagram illustrating an embodiment of the invention in which a combined sanitization and precooling container comprises a pass-thru system for palletized product harvested from a meat processing facility.

According to yet another embodiment, one or more mobile containers can be designed as a pass-thru unit or container to cool and to sanitize product that is prepared and/or harvested in a meat processing facility. For example, as shown in the embodiment of FIG. 43, at least one meat processing facility or packing house (H) is used process meat or other protein(s). The processed, prepared, and/or harvested product from the meat processing facility or packing house (H) is placed within consumer/retail packages and palletized via a packing line (9410) that is positioned within the meat processing facility or packing house (H). The pallets of product are placed within one or more modified, mobile containers (9400) to cool and to apply the sanitizing treatment before shipment. The one or more modified, mobile containers (9400) of FIG. 43 are designed as "pass-thru" units or containers, as the pallets of product pass directly into the one or more modified, mobile containers (9400) from the meat processing facility or packing house (H) via, e.g., a conveyor or pallet shuttle (9470). According to one embodiment, an additional refrigeration unit (9460) can be positioned next to the one or more modified, mobile containers (9400) for providing additional cooling capacity to the one or more modified, mobile containers (9400). At this point, the cooled and sanitized pallets of product can optionally be treated with an MAP process (9440) with (or without) an additional sanitizer treatment. Thereafter, the pallets of product are staged for shipping within a shipping area (9430) and then the pallets are placed within semi-trailers (9450) to ship the pallets to one or more customers. In the embodiment of FIG. 43, the one or more modified, mobile containers (9400) that are positioned as a "pass-thru" unit or container for cooling and applying the sanitizing treatment to pallets of product are "cross-docked" from the shipping area (9430) having the semi-trailers (9450).

Although embodiments of the invention described herein include a mobile container or a semi-trailer, other types of mobile or movable containers and/or units are contemplated in accordance with the principles of the invention. For example, portions of the container, including, e.g., the walls and/or shell of the unit, and/or refrigeration components can be picked up and/or disassembled and placed on a truck for movement to also be mobile.

Although embodiments of the invention described herein include perishable products, such as berries, bananas, avocado, etc., various other perishable products are able to be cooled by the modified container and/or semi-trailer of the invention. For example, perishable products include, but are not limited to, lettuce products, basil, broccoli, beans, cucumbers, eggplants, squash and other herbs and vegetables, tomatoes, berries, cherries, grapes, peaches, melons and other fruit, or highly perishable produce. According to embodiments, the perishable product is a protein including but not limited to meat, fish, fowl, and vegetable protein products. According to embodiments, the perishable product is cannabis and hemp or medicinal products. According to embodiments, the perishable product is a floral product including roses and cut flowers.

According to an embodiment of the invention, baffles to seal in contact with the pallets to cause the air flow to be forced through the pallets are intended. These baffles may be fixed in place or can be rotated or shifted to seal the pallets during operation using manual or automated components.

According to an embodiment of the invention, protective coatings can be applied to the walls of the container and/or semi-trailer, refrigeration equipment, shuttle conveyor, and/or any other materials that will come into contact with the sanitizing ingredients.

According to an embodiment of the invention, the modifications to the container or semi-trailer can also include special venting of the gas from the unit prior to entry for removing the pallets. This venting could incorporate a catalytic converter in the case of ozone, or a scrubber that would neutralize any corrosive mists or fog.

Similarly, according to an embodiment of the invention, the modifications to the container or semi-trailer can also include special treatment of the condensate and washout drains for proper neutralization and liquid transmission to the facility drains.

According to an embodiment, the methods and apparatus of the invention can include (a) moving each of the pallets into position and at the plenum within the modified mobile containers and semi-trailers, and (b) after properly positioning each pallet adjacent to the plenum (within the modified container or semi-trailer), creating a seal that matches the edge dimension of the goods/vented boxes/packaging stacked on the pallets in order to optimize the airflow across the goods and through the vented boxes/packaging for efficient and effective cooling, sanitizing and/or ripening.

According to an embodiment, a mechanism is further provided to move pallet closure pads to meet the pallets that have been loaded into the one of (i) a mobile container or (ii) a semi-trailer, to create a seal to create a positive air flow plenum and thus force air through the pallets instead of around. According to one embodiment, the mechanism to move the pallet closure pads may be operated by at least one of hydraulic means (cylinders), at least one mechanical device or drive (such as a pulley or servo motor), or air pressure (inflatable pads or cushions). When loading or unloading the container, the mechanism releases the pads and backs away from the pallets.

Another embodiment of the invention relates to using unconventional materials to treat and cool the perishable product. For treatment, solutions of materials that include organic liquids such as alcohols have excellent sanitizing properties. The electrical system for the mobile container could require specifications for flammable components or modified atmosphere. Additionally, industrial gas such as nitrogen could be used to provide an inert atmosphere inside the container and also be a component to aid the cooling process.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. An apparatus for cooling a perishable product to an intended temperature, the apparatus comprising:
    one of a mobile container or a semi-trailer that is modified to provide refrigeration and airflow that is forced through pallets of cartons of the perishable product and/or vented packages of the perishable product; and
    a mechanism to move plenum opening and pallet closure pads to meet the pallets that have been loaded into the one of a mobile container or a semi-trailer, to create a seal and to create a positive air flow plenum and thus force air through the pallets instead of around,
    wherein the one of a mobile container or a semi-trailer includes at least one refrigeration source that is configured to supply a cooled airflow to the one of a mobile container or a semi-trailer that is directed across the pallets of cartons of the perishable product and/or vented packages of the perishable product contained within the one of a mobile container or a semi-trailer, and
    wherein the one of a mobile container or a semi-trailer is configured to be relocated to a production facility or a seasonal growing area for increased or year-round utilization.

2. An apparatus for sanitizing a perishable product in which sanitizing substances are recirculated within air that flows across a surface of the perishable product to reduce at least one of pathogenic organisms or spoilage organisms that occur on the surface of the perishable product, the apparatus comprising one of a mobile container or a semi-trailer that is modified to supply the sanitizing substances to the perishable product,
    wherein the one of a mobile container or a semi-trailer includes at least one treatment system or spraying system that is configured to supply a gaseous material, ultra-fine to small micron sized suspended substances, or a vaporized substance for sanitizing or treating the surface of the perishable product contained within the one of a mobile container or a semi-trailer,
    wherein the sanitizing substances are mixed with a carrier that includes one of air, industrial gas, water, or alcohol,
    wherein airflow is regulated to aid in reducing droplet size of the substances and distribution of the substances throughout and across pallets holding the perishable product, and
    wherein microbubbles of the substances released into the airflow via recirculated fans uniformly distributes the substances using at least one of pressured $N_2$, $CO_2$, and pressurized air to the surface of the perishable product being held by the pallets.

3. A system for sanitizing and cooling a perishable product, the system comprising:
    at least one sanitization apparatus for a sanitization process; and
    at least one cooling apparatus for a cooling process,
    wherein airflow and cooling capacity is established to achieve a selected sanitizer recirculation and cooling rate,
    wherein the sanitizer process and the cooling process are controlled for designed purposes and cycles, and
    wherein venting of gases and discharge of liquid condensate and substances from the sanitizer process and the cooling process is controlled for environmental concerns.

4. The apparatus according to claim 1, wherein the mechanism is configured to slide up and down to adjust to different heights of pallets, and
    wherein the pallet closure pads are configured to adjust and contact the pallets to create the seal for creating a positive pressure air flow through the pallets.

5. The apparatus according to claim 1, wherein the mechanism to move the plenum opening and pallet closure pads is operated by at least one of hydraulic means, at least one mechanical device or drive, or air pressure.

6. An overall system for automated postharvest handling, treatment, precooling, conditioning, and preparation for distribution of palletized products supporting production facilities, the system comprising:
    at least one of one or more mobile, portable modified containers or one or more refrigeration sources; and
    one or more conveyors or pallet shuttle apparatus interconnecting the at least one of one or more mobile, portable modified containers or one or more refrigeration sources, wherein the system uses prescribed methods and programmed apparatus to provide palletized product sanitizing, precooling, treating, and handling of the palletized products from receiving to loading and shipping.

7. The overall system according to claim 6, wherein the at least one of one or more mobile, portable modified containers or one or more refrigeration sources includes at least one pallet shuttle apparatus and comprises a pass-thru design to receive product directly from a processing or packing line and to deliver the product from a discharge end directly to one of a modified atmosphere pallet (MAP) system or loading and shipping.

8. An apparatus for sanitizing a perishable product in which sanitizing substances are recirculated within air that flows across a surface of the perishable product to reduce at least one of pathogenic organisms or spoilage organisms that occur on the surface of the perishable product, the apparatus comprising one of a mobile container or a semi-trailer that is modified to supply the sanitizing substances to the perishable product,
    wherein the one of a mobile container or a semi-trailer includes at least one treatment system or spraying system that is configured to supply a gaseous material, ultra-fine to small micron sized suspended substances, or a vaporized substance for sanitizing or treating the surface of the perishable product contained within the one of a mobile container or a semi-trailer, and
    wherein an environment inside the one of a mobile container or a semi-trailer is controlled to add nitrogen or carbon dioxide to create an atmosphere in which alcohols, ethers or other flammable or hazardous substances can be safely used as part of a sanitizing process.

9. An apparatus for cooling a perishable product to an intended temperature, the apparatus comprising one of a mobile container or a semi-trailer that is modified to provide refrigeration and airflow that is forced through pallets of cartons of the perishable product and/or vented packages of the perishable product,
    wherein the one of a mobile container or a semi-trailer includes at least one refrigeration source that is configured to supply a cooled airflow to the one of a mobile container or a semi-trailer that is directed across the pallets of cartons of the perishable product and/or the vented packages of the perishable product contained within the one of a mobile container or a semi-trailer,
    wherein the one of a mobile container or a semi-trailer is configured to be relocated to a production facility or a seasonal growing area for increased or year-round utilization,
    wherein modifications to the one of a mobile container or a semi-trailer include one or more of:
        adding at least one refrigeration unit and air flow components along one or more sidewalls on an inside of the one of a mobile container or a semi-trailer for the cooling of at least a single row of pallets of the perishable product;
        creating pop-out sidewalls and adding a roof mounted refrigeration unit, to enable horizontal cooling and treatment air for the one of a mobile container or a semi-trailer filled with at least two rows of pallets of the perishable product;
        creating at least one pop-out sidewall and adding a wall mounted refrigeration unit, to enable horizontal cooling and treatment air for the one of a mobile container or a semi-trailer filled with at least two rows of pallets of the perishable product;
        creating pop-out sidewalls and adding a corner mounted refrigeration unit, to enable horizontal cooling and treatment air for the one of a mobile container or a semi-trailer filled with at least two rows of pallets of the perishable product; and
        attaching a plurality of refrigeration units to one or more sidewalls of the one of a mobile container or a semi-trailer, wherein the one or more sidewalls have openings to enable horizontal air to cool and to treat at least one row of pallets of the perishable product and to return the air to the plurality of refrigeration units; and
    wherein the openings in the one or more sidewalls have a vent or shutter design that enables them to be opened and closed, and to adjust and direct the airflow to the pallets.

10. An apparatus for cooling a perishable product to an intended temperature, the apparatus comprising one of a mobile container or a semi-trailer that is modified to provide refrigeration and airflow that is forced through pallets of cartons of the perishable product and/or vented packages of the perishable product,
    wherein the one of a mobile container or a semi-trailer includes at least one refrigeration source that is configured to supply a cooled airflow to the one of a mobile container or a semi-trailer that is directed across the pallets of cartons of the perishable product and/or the vented packages of the perishable product contained within the one of a mobile container or a semi-trailer,
    wherein the one of a mobile container or a semi-trailer is configured to be relocated to a production facility or a seasonal growing area for increased or year-round utilization, and
    wherein the one of a mobile container or a semi-trailer includes slot or expanded floor drains that are configured to be sealed during cooling and/or sanitizing treatments and/or conditioning or ripeness management treatments and opened to enable removal of any physical debris, water and/or cleaning solutions from daily cleaning and sanitation of the one of a mobile container or a semi-trailer.

11. An apparatus for cooling a perishable product to an intended temperature, the apparatus comprising one of a mobile container or a semi-trailer that is modified to provide refrigeration and airflow that is forced through pallets of cartons of the perishable product and/or vented packages of the perishable product,
    wherein the one of a mobile container or a semi-trailer includes at least one refrigeration source that is configured to supply a cooled airflow to the one of a mobile container or a semi-trailer that is directed across the pallets of cartons of the perishable product and/or the vented packages of the perishable product contained within the one of a mobile container or a semi-trailer,
    wherein the one of a mobile container or a semi-trailer is configured to be relocated to a production facility or a seasonal growing area for increased or year-round utilization, and
    wherein a first sanitizing treatment occurs before, during, or after cooling of the perishable product, and then a second sanitizing treatment occurs within a modified atmosphere pallet (MAP) process.

12. An apparatus for cooling a perishable product to an intended temperature, the apparatus comprising one of a mobile container or a semi-trailer that is modified to provide refrigeration and airflow that is forced through pallets of cartons of the perishable product and/or vented packages of the perishable product,
- wherein the one of a mobile container or a semi-trailer includes at least one refrigeration source that is configured to supply a cooled airflow to the one of a mobile container or a semi-trailer that is directed across the pallets of cartons of the perishable product and/or vented packages of the perishable product contained within the one of a mobile container or a semi-trailer,
- wherein the one of a mobile container or a semi-trailer is configured to be relocated to a production facility or a seasonal growing area for increased or year-round utilization, and
- wherein gases from an inside of the one of a mobile container or a semi-trailer are vented to an outside of the one of a mobile container or a semi-trailer using one of a catalytic converter for ozone or a scrubber to neutralize any acidic or alkaline mists or fog.

13. An apparatus for cooling a perishable product to an intended temperature, the apparatus comprising one of a mobile container or a semi-trailer that is modified to provide refrigeration and airflow that is forced through pallets of cartons of the perishable product and/or vented packages of the perishable product,
- wherein the one of a mobile container or a semi-trailer includes at least one refrigeration source that is configured to supply a cooled airflow to the one of a mobile container or a semi-trailer that is directed across the pallets of cartons of the perishable product and/or vented packages of the perishable product contained within the one of a mobile container or a semi-trailer,
- wherein the one of a mobile container or a semi-trailer is configured to be relocated to a production facility or a seasonal growing area for increased or year-round utilization, and
- wherein condensate and washout drains are closed during use of the apparatus, in order to collect and to neutralize waste for transmission and disposal to facility drains.

14. An apparatus for cooling a perishable product to an intended temperature, the apparatus comprising one of a mobile container or a semi-trailer that is modified to provide refrigeration and airflow that is forced through pallets of cartons of the perishable product and/or vented packages of the perishable product,
- wherein the one of a mobile container or a semi-trailer includes at least one refrigeration source that is configured to supply a cooled airflow to the one of a mobile container or a semi-trailer that is directed across the pallets of cartons of the perishable product and/or vented packages of the perishable product contained within the one of a mobile container or a semi-trailer,
- wherein the one of a mobile container or a semi-trailer is configured to be relocated to a production facility or a seasonal growing area for increased or year-round utilization, and
- wherein a first modified container or semi-trailer first cools the perishable product and a second modified container or semi-trailer sanitizes the perishable product, or a first modified container or semi-trailer first sanitizes the perishable product and a second modified container or semi-trailer cools the perishable product.

15. The system according to claim 3, further comprising a modified atmosphere pallet (MAP) application system.

16. The system according to claim 15, further comprising at least one conveyor system to transport the perishable product between one or more of (i) the at least one sanitization apparatus, (ii) the at least one cooling apparatus, and (iii) the modified atmosphere pallet (MAP) application system.

\* \* \* \* \*